United States Patent
Metcalf, III et al.

(10) Patent No.: US 7,091,213 B2
(45) Date of Patent: Aug. 15, 2006

(54) PHOSPHORUS-CONTAINING COMPOUNDS AND USES THEREOF

(75) Inventors: Chester A. Metcalf, III, Needham, MA (US); Leonard W. Rozamus, Bedford, MA (US); Yihan Wang, Newton, MA (US); David L. Berstein, Waban, MA (US)

(73) Assignee: ARIAD Gene Therapeutics, Inc., Cambridge, MA (US)

( * ) Notice: Subject to any disclaimer, the term of this patent is extended or adjusted under 35 U.S.C. 154(b) by 0 days.

(21) Appl. No.: 10/862,149

(22) Filed: Jun. 4, 2004

(65) Prior Publication Data

US 2005/0032825 A1    Feb. 10, 2005

Related U.S. Application Data

(63) Continuation-in-part of application No. 10/635,054, filed on Aug. 6, 2003, now abandoned, and a continuation-in-part of application No. 10/357,152, filed on Feb. 3, 2003, now abandoned.

(60) Provisional application No. 60/433,930, filed on Dec. 17, 2002, provisional application No. 60/428,383, filed on Nov. 22, 2002, provisional application No. 60/426,928, filed on Nov. 15, 2002, provisional application No. 60/353,252, filed on Feb. 1, 2002.

(51) Int. Cl.

| C07D 491/06 | (2006.01) |
|---|---|
| A61K 31/395 | (2006.01) |
| A61P 35/00 | (2006.01) |
| A61P 35/02 | (2006.01) |

(52) U.S. Cl. .................. 514/291; 540/456
(58) Field of Classification Search ........... 540/456; 514/291

See application file for complete search history.

(56) References Cited

U.S. PATENT DOCUMENTS

| 5,206,018 A | 4/1993 | Sehgal et al. |
|---|---|---|
| 5,234,456 A | 8/1993 | Silvestrini |
| 5,310,903 A | 5/1994 | Goulet et al. |
| 5,385,910 A | 1/1995 | Ocain et al. |
| 5,391,730 A | 2/1995 | Skotnicki et al. |
| 5,434,260 A | 7/1995 | Skotnicki et al. |
| 5,489,680 A | 2/1996 | Failli et al. |
| 5,491,231 A | 2/1996 | Nelson et al. |
| 5,516,781 A | 5/1996 | Morris et al. |
| 5,665,591 A | 9/1997 | Sonenshein et al. |
| 5,851,217 A | 12/1998 | Wolff et al. |
| 5,968,091 A | 10/1999 | Pinchuk et al. |
| 6,146,358 A | 11/2000 | Rowe |
| 6,152,141 A | 11/2000 | Stevens et al. |
| 6,585,764 B1 | 7/2003 | Wright et al. |
| 2001/0010920 A1 | 8/2001 | Molnar-Kimber et al. |

FOREIGN PATENT DOCUMENTS

| WO | WO 90/13332 | 11/1990 |
|---|---|---|
| WO | WO 92/06992 | 4/1992 |
| WO | WO 2003/064383 A3 | 8/2003 |

*Primary Examiner*—Bruck Kifle
(74) *Attorney, Agent, or Firm*—David L. Berstein

(57) ABSTRACT

This invention concerns a new family of phosphorus-containing compounds containing a moiety JQA- in which:
A is absent or is —O—, —S— or —NR$^2$—;
Q is absent or (if A is —O—, —S— or —NR$^2$—) Q may be —V—, —OV—, —SV—, or —NR$^2$V—, where V is an aliphatic, heteroaliphatic, aryl, or heteroaryl moiety, such that J is linked to the cyclohexyl ring directly, through A or through VA, OVA, SVA or NR$^2$VA;

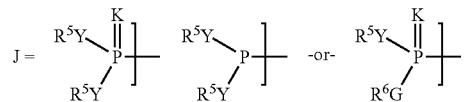

K is O or S;
each occurrence of Y is independently —O—, —S—, —NR$^2$—, or a bond linking a R$^5$ moiety to P;
each occurrence of R$^2$ and R$^5$ is independently an aliphatic, heteroaliphatic, aryl, or heteroaryl moiety, or H; and
each occurrence of R$^6$ is independently —PK(YR$^5$)(YR$^5$), —SO$_2$(YR$^5$) or —C(O)(YR$^5$); so long as any R$^2$, or R$^5$ moiety linked directly to P is not H;
wherein two R$^2$, R$^5$ and/or R$^6$ moieties may be chemically linked to one another to form a ring;
each occurrence of G is independently —O—, —S—, —NR$^2$— or (M)$_x$;
each occurrence of M is independently a substituted or unsubstituted methylene moiety, and any M-M' moiety may be saturated or unsaturated;
each occurrence of x is independently an integer from 1–6; and the other variables are as defined herein.

36 Claims, No Drawings

PHOSPHORUS-CONTAINING COMPOUNDS AND USES THEREOF

RELATED APPLICATIONS

The present application is a continuation-in-part of U.S. patent application Ser. No. 10/635,054, filed Aug. 6, 2003 now abandoned and U.S. patent application Ser. No. 10/357,152, filed Feb. 3, 2003 now abandoned and claims priority thereto and under 35 U.S.C. § 119(e) to U.S. Provisional Patent Application No. 60/353,252, filed Feb. 1, 2002, U.S. Provisional Patent Application No. 60/426,928, filed Nov. 15, 2002, U.S. Provisional Patent Application No. 60/428,383, filed Nov. 22, 2002, and U.S. Provisional Patent Application No. 60/433,930, filed Dec. 17, 2002, the entire contents of each of these applications are hereby incorporated by reference.

BACKGROUND OF THE INVENTION

Rapamycin is a macrolide antibiotic produced by *Streptomyces hygroscopicus*. It binds to a FK506-binding protein, FKBP12, with high affinity to form a rapamycin:FKBP complex. Reported Kd values for that interaction are as low as 200 pM. The rapamycin:FKBP complex binds with high affinity to the large cellular protein, FRAP, to form a tripartite, [FKBP:rapamycin]:[FRAP], complex. In that complex rapamycin can be viewed as a dimerizer or adapter to join FKBP to FRAP. Formation of the complex is associated with rapamycin's various biological activities.

Rapamycin is a potent immunosuppressive agent and is used clinically to prevent rejection of transplanted organs. Rapamycin and/or its analogs, CCI 779 (Wyeth) and SDZ Rad ("RAD001", Novartis) are promising agents for treating certain cancers, for immune suppression and/or for helping to decrease the incidence of restenosis following interventional cardiology. Rapamycin has also been shown to have activity as an antifungal agent, in the experimental allergic encephalomyelitis model (a model for multiple sclerosis), in the adjuvant arthritis model (for rheumatoid arthritis), in inhibiting the formation of IgE-like antibodies, and for treating or preventing lupus erythematosus, pulmonary inflammation, insulin dependent diabetes mellitus, adult T-cell leukemia/lymphoma, and smooth muscle cell proliferation and intimal thickening following vascular injury. See e.g. U.S. Pat. appln 2001/0010920.

Because it serves as an adapter to complex FKBP with FRAP, rapamycin is also capable of multimerizing appropriately designed chimeric proteins incorporating domains derived from FKBP and FRAP, respectively; Because of that activity, rapamycin and various derivatives or analogs thereof have also been used as multimerizing agents for activating biological switches based on such chimeric proteins. See e.g., WO96/41865; WO 99/36553; WO 01/14387; Rivera et al, Proc Natl Acad Sci USA 96, 8657–8662; and Ye, X. et al (1999) Science 283, 88–91.

Rapamycin's potential for providing relief from such an important swath of cruel diseases has stimulated the search for rapamycin analogs with improved therapeutic index, pharmacokinetics, formulatability, ease or economy of production, etc. The resulting investigation by the pharmaceutical industry and academic researchers has been a sustained one over the past few decades. This has led to the exploration of materials and methods for effecting chemical transformations of rapamycin, including reductions of ketones, demethylations, epimerizations, various acylations and alkylations of hydroxyls, etc.

A large number of structural variants of rapamycin have now been reported, typically arising as alternative fermentation products and/or from synthetic efforts. For example, the extensive literature on analogs, homologs, derivatives and other compounds related structurally to rapamycin ("rapalogs") include, among others, variants of rapamycin having one or more of the following modifications relative to rapamycin: demethylation, elimination or replacement of the methoxy at C7, C42 and/or C29; elimination, derivatization or replacement of the hydroxy at C13, C43 and/or C28; reduction, elimination or derivatization of the ketone at C14, C24 and/or C30; replacement of the 6-membered pipecolate ring with a 5-membered prolyl ring; and alternative substitution on the cyclohexyl ring or replacement of the cyclohexyl ring with a substituted cyclopentyl ring. Additional historical information is presented in the background sections of U.S. Pat. Nos. 5,525,610; 5,310,903 and 5,362,718. See also U.S. Pat. No. 5,527,907. Materials and methods have even been developed for the remarkably effective and selective epimerization of the C-28 hydroxyl group (WO 01/14387).

New rapalogs with reduced immunosuppressive activity and/or interesting pharmacokinetic or bioavailability profiles would be very desirable for use as multimerizing agents or antifungal agents.

New rapalogs with attractive physicochemical or functional characteristics, e.g., in therapeutic index, bioavailability, pharmacokinetics, stability, etc., would also be of interest for a variety of pharmaceutical uses such as are mentioned above, including among others use as immunosuppressants, as anticancer agents and in reducing the incidence of restenosis following interventional cardiology (e.g. on drug-bearing stents).

The only rapalogs thought to be in clinical development as immunosuppressants at present are those with rather modest, conventional structural modifications, i.e., acylation or alkylation at C-43 (CCI 779 and SDZ RAD, respectively; see e.g., Yu, K. et al., Endocrine-Related Cancer (2001) 8, 249–258; Geoerger, B. et al., Cancer Res. (2001) 61 1527–1532) and Dancey, Hematol Oncol Clin N Am 16 (2002):1101–1114. Stents bearing a tetrazole-substituted rapalog, ABT-578, but having only a shortened biological half-life (see e.g. WO 03/022807 and 99/15530) are reportedly being studied too.

The invention described below represents a rather dramatic departure in the design of new rapalogs based on the incorporation of a phosphorus-containing moiety.

SUMMARY OF THE INVENTION

Compounds of this invention include a new family of compounds of Formula (I):

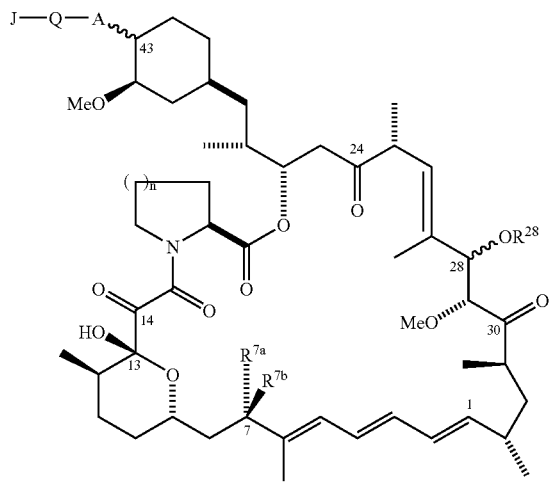

and pharmaceutically acceptable derivatives thereof. Compositions containing such compounds and uses thereof are also provided.

In the compounds of this invention,

A is —O—, —S— or —NR$^2$—, or is absent (i.e., is a covalent bond linking JQ- to carbon 43);

Q is absent (i.e., is a covalent bond linking J to A or to carbon 43) or, if A is —O—, —S— or —NR$^2$—, Q may be —V—, —OV—, —SV—, or —NR$^2$V—, where V is an aliphatic, heteroaliphatic, aryl, or heteroaryl moiety, such that J is linked to the cyclohexyl ring directly, through A or through VA, OVA, SVA or NR$^2$VA (i.e., as JA-, JVA-, JOVA-, JSVA- and JNR$^2$VA-;

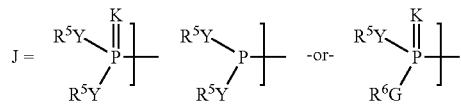

K is O or S;

each occurrence of Y is independently —O—, —S—, —NR$^2$—, or a chemical bond linking a R$^5$ moiety to P;

each occurrence of R$^2$ and R$^5$ is independently an aliphatic, heteroaliphatic, aryl, or heteroaryl moiety, or H; and each occurrence of R$^6$ is independently —PK(YR$^5$)(YR$^5$), —SO$_2$(YR$^5$) or —C(O)(YR$^5$); so long as any R$^2$ or R$^5$ moiety linked directly to P is not H (e.g., —PR$^2$ and —PR$^5$ cannot be —PH);

wherein two R$^2$, R$^5$ and/or R$^6$ moieties may be chemically linked to one another to form a ring;

each occurrence of G is independently —O—, —S—, —NR$^2$— or (M)$_x$;

each occurrence of M is independently a substituted or unsubstituted methylene moiety, and any M-M' moiety may be saturated or unsaturated;

each occurrence of x is independently an integer from 1–6;

one of R$^{7a}$ and R$^{7b}$ is H and the other is H, halo, —R$^A$, —OR$^A$, —SR$^A$, —OC(O)R$^A$, —OC(O)NR$^A$R$^B$, —NR$^A$R$^B$, —NR$^B$C(O)R$^A$, —NR$^B$C(O)OR$^A$, —NR$^B$SO2R$^A$ or —NR$^B$SO2NR$^A$R$^{B\dagger}$; or R$^{7a}$ and R$^{7b}$, taken together, are H in the tetraene moiety:

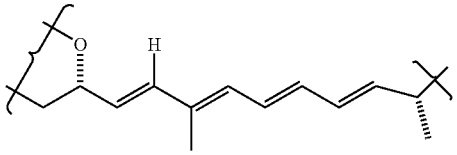

where R$^A$ is R$^2$ and where R$^B$ is OH or R$^2$. In some cases one or both of R$^A$ and R$^B$ is H;

R$^{28}$ is hydrogen; J; or an aliphatic, heteroaliphatic, aryl, heteroaryl, acyl, aroyl or heteroaroyl moiety;

and n is 1 or 2;

wherein each of the foregoing aliphatic and heteroaliphatic moieties is independently linear or branched, or cyclic or acyclic, and substituted or unsubstituted, and each of the aryl, heteroaryl, acyl, aroyl or heteroaroyl moieties is independently substituted or unsubstituted;

with the proviso that (a) if JQA- is (R$^2$Y)(Me)(P=O)O—, then (R$^2$Y) is (i) not an immunogenic carrier material, detector carrier material or a solid matrix, or (ii) R$^2$ contains 15 or fewer carbon atoms, preferably 10 or fewer); and (b) the compound is not

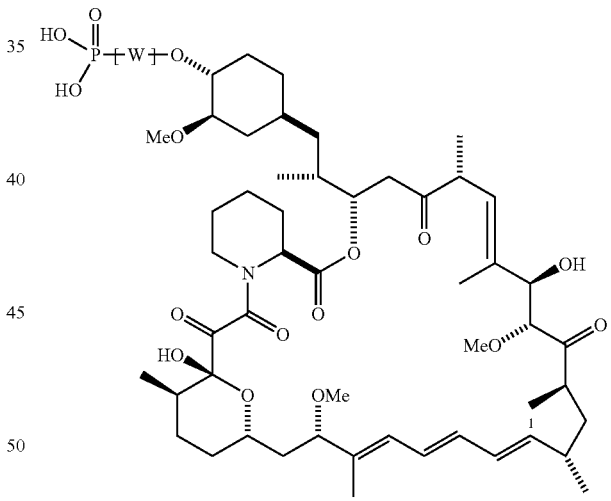

or a desmethyl or reduced analog thereof, or a salt of any of the foregoing, where W comprises a substituted or unsubstituted heterocycle comprising

alone or fused to a six-membered aromatic ring, wherein U is substituted or unsubstituted amino, O, S, SO or SO$_2$; and (c) in compounds of the formula:

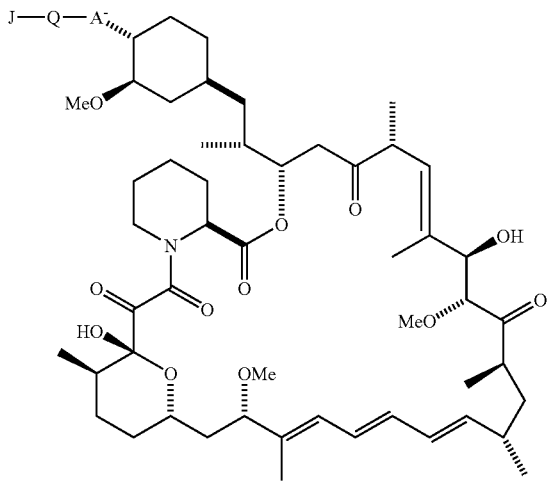

J-Q-A- is not $(HO)_2(PO)$—O— or the dimethyl phosphate ester thereof (and preferably not another di-lower alkyl ester thereof). Wavy bonds, e.g., as shown in FIG. 1 at positions 28 and 43 indicate that the substituent may be in either orientation.

J moieties of special interest in various embodiments of this invention include those shown in Series 1:

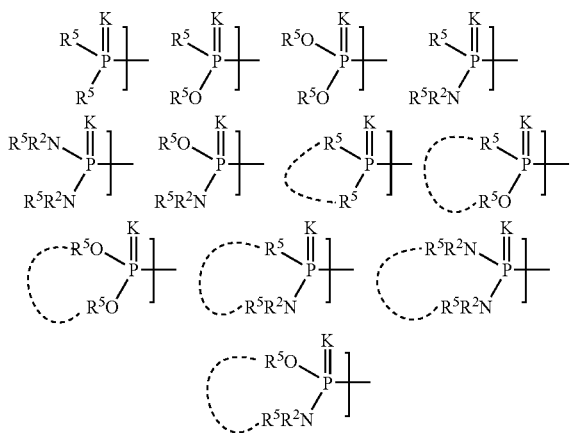

where K, $R^2$, $R^5$ and $R^6$ are as defined above. J moieties currently of special interest are those in which K is oxygen, as are illustrated in numerous exemplary compounds depicted below, including among others, any of the following:

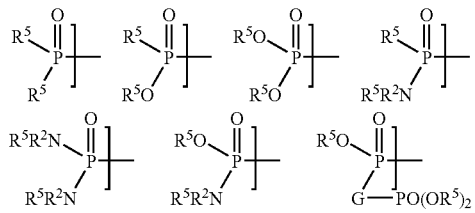

in which each occurrence of $R^5$ is an independently chosen lower aliphatic or aryl moiety, which may be substituted or unsubstituted, or in the case of —$OR^5$ moieties, may alternatively be H. Also of current special interest are embodiments in which -Q-A- is O, especially in cases in which J is one of the currently preferred J moieties noted just above (although preferably not —$PO_3H_2$). Of special interest too are any of the foregoing compounds in which in which JQA- is $(R^2Y)(Me)(P=O)O$— in which $R^2Y$— contains 15 or fewer carbon atoms, preferably 10 or fewer carbon atoms, and in some embodiments 6 or fewer carbon atoms.

This new family of compounds includes a number of classes of compounds of particular interest.

For instance, one such class is illustrated by formula (a):

(a)

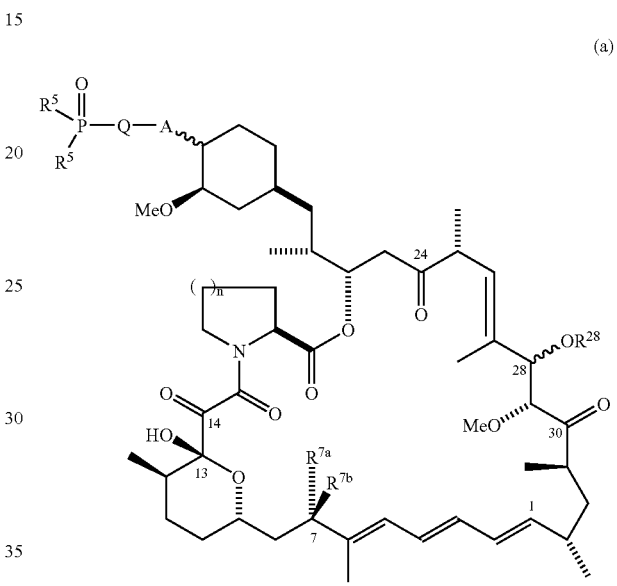

In this class, each $R^5$ is an independently selected, aliphatic, heteroaliphatic, aryl, or heteroaryl moiety (which moiety may be substituted or unsubstituted), especially a lower (i.e. from 1 to 6 carbons) aliphatic moiety, e.g., a lower alkyl, which may be optionally substituted (e.g. with a halo, hydroxyl, —O-acyl (i.e., acyloxy), alkoxyl, haloalkyl-, hydroxyalkoxyl, aryl, or heteroaryl moiety, etc.). In several examples of this class, the compounds of formula (a) comprise a moiety, J, selected from the following:

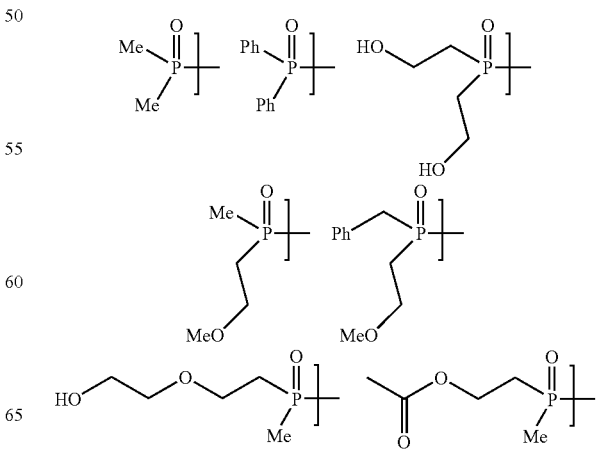

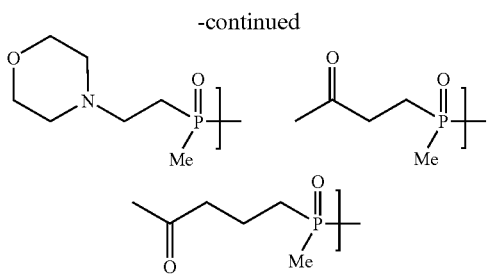

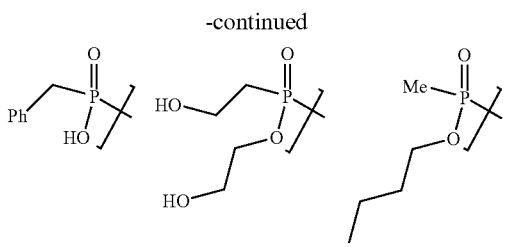

This class is further illustrated in the synthetic examples that follow, through members of its subclass in which J-Q-A- is $(R^5)_2PO—O—$. Furthermore, note that all of the $R^2$, $R^5$, $R^6$ and J moieties disclosed or exemplified herein in connection with a given compound, subclass or class of compounds are equally applicable in other cases unless otherwise specified. Thus, the disclosure of a $R^2$, $R^5$, $R^6$ or J moiety in one case is intended to be extrapolated to all other cases except as otherwise noted.

Another class of compounds of this invention which is also of interest is illustrated by formula (b):

(b)

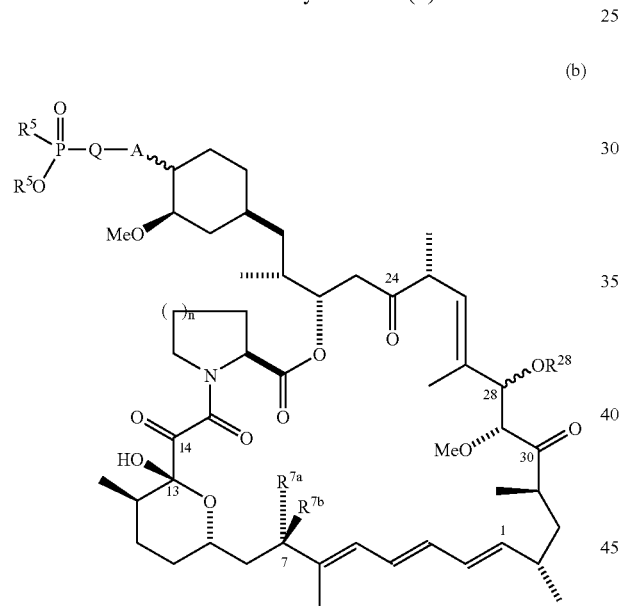

In this class, each $R^5$ is an independently selected, aliphatic, heteroaliphatic, aryl, or heteroaryl moiety (which moiety may be substituted or unsubstituted), especially a lower aliphatic moiety, e.g. a lower alkyl, which may be optionally substituted (e.g. with a hydroxyl, alkoxyl, hydroxyalkoxyl, acyloxy-, aryl, or heteroaryl moiety, etc.). In the case of —$OR^5$, the $R^5$ moiety may additionally be H. Illustrative examples include compounds of formula (b) in which J is selected from the following:

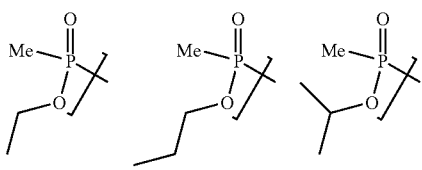

This class is further illustrated in the synthetic examples that follow, through members of its subclass in which J-Q-A- is $(R^5)(R^5O)PO—O—$.

Another class of compounds of this invention which is also of interest is illustrated by formula (c), with the proviso noted at the outset:

(c)

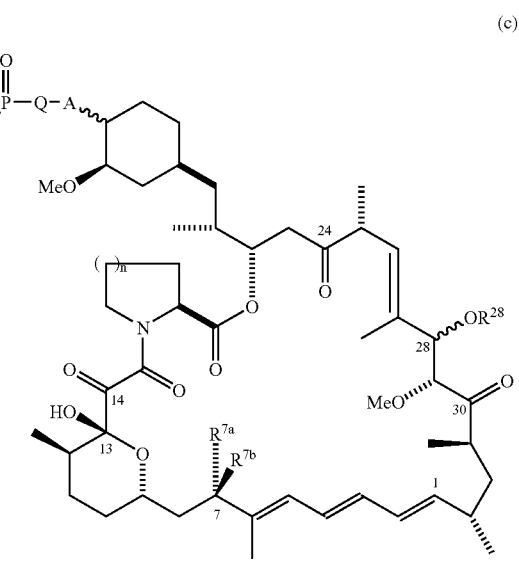

In this class, each $R^5$ is independently selected, and is H or an aliphatic, heteroaliphatic, aryl, or heteroaryl moiety (which moiety may be substituted or unsubstituted), especially lower aliphatic moiety, including lower alkyl, which may be optionally substituted (e.g. with a hydroxyl, alkoxyl, hydroxyalkoxyl, acyloxy-, aryl, or heteroaryl moiety, etc.). Illustrative examples include compounds of formula (c) in which J is selected from the following:

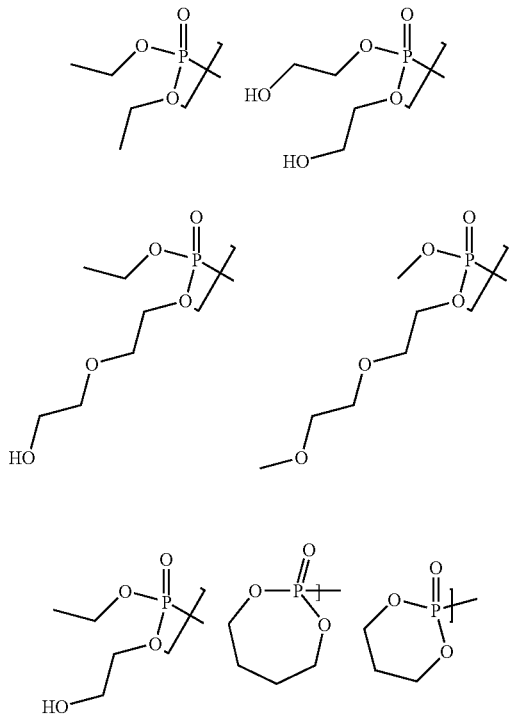

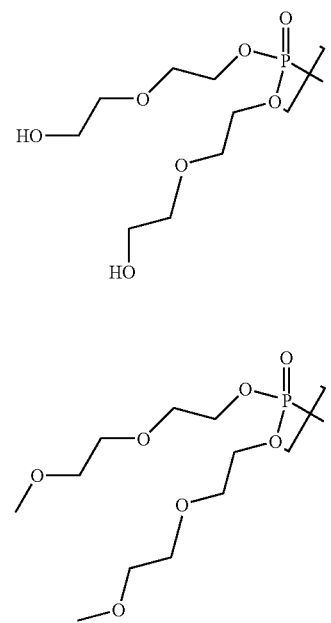

This class is further illustrated in the synthetic examples that follow, including members of its subclass in which J-Q-A- is $(R^5O)(R^5O)PO$—O—.

Another class of compounds of this invention which is also of interest is illustrated by formula (d):

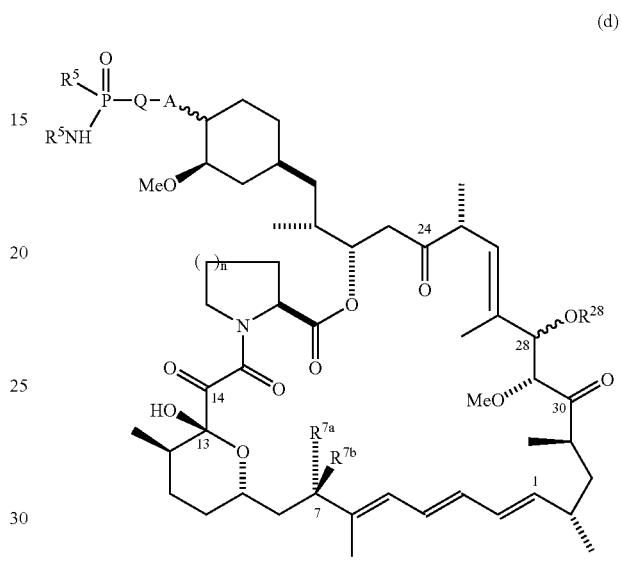

(d)

In this class, each $R^5$ is an independently selected, aliphatic, heteroaliphatic, aryl, or heteroaryl moiety (which moiety may be substituted or unsubstituted), especially lower (i.e. from 1 to 6 carbons) aliphatic moiety including lower alkyl, which may be optionally substituted (e.g. with a hydroxyl, alkoxyl, hydroxyalkoxyl, acyloxy-, aryl, or heteroaryl moiety, etc.). In some embodiments —$NHR^5$ is —$NH_2$. Illustrative examples include compounds of formula (d) in which J is selected from the following:

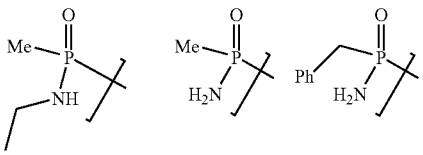

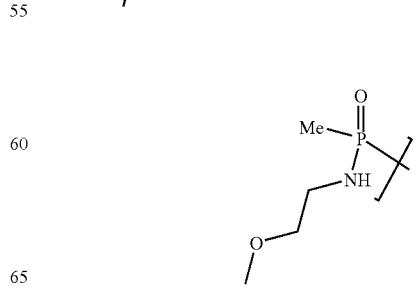

This class is further illustrated by its subclass in which J-Q-A- is $(R^5)(R^5N)PO—O—$.

Another class of compounds of this invention which is also of interest is illustrated by formula (e):

This class is further illustrated in the synthetic examples that follow, through members of its subclass in which J-Q-A- is $(R^5N)(R^5N)PO—O—$.

Another class of compounds of this invention also of interest is illustrated by formula (f):

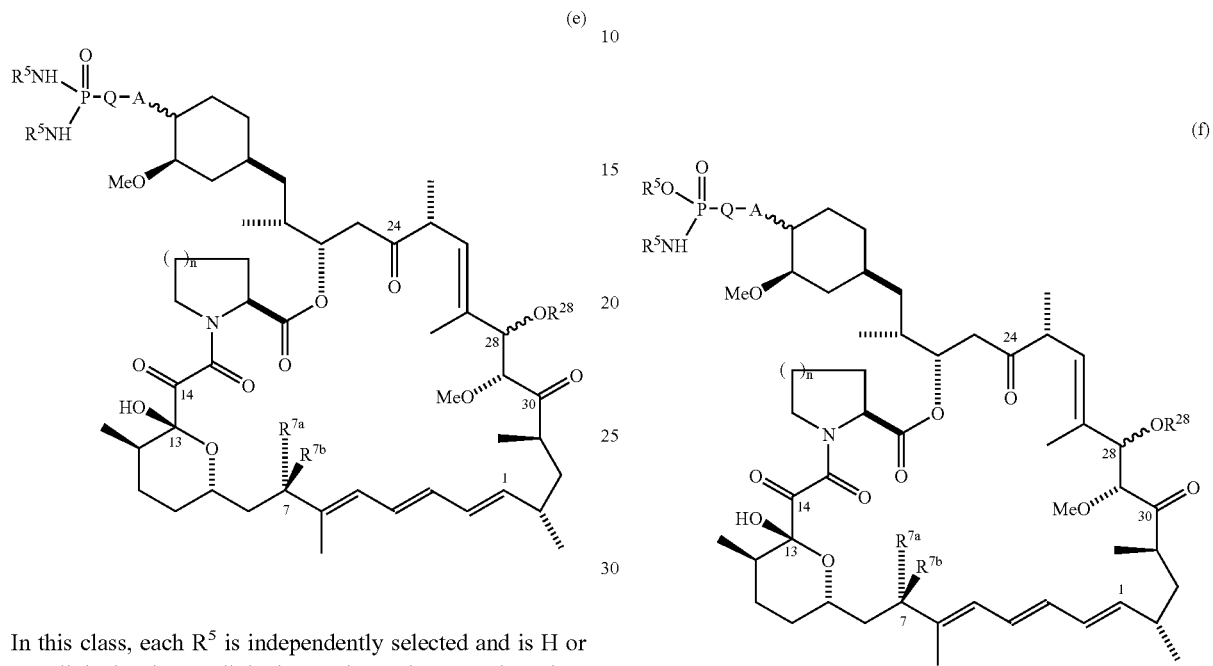

In this class, each $R^5$ is independently selected and is H or an aliphatic, heteroaliphatic, aryl, or heteroaryl moiety (which moiety may be substituted or unsubstituted), especially lower (i.e. from 1 to 6 carbons) aliphatic moiety including lower alkyl, which may be optionally substituted (e.g. with a hydroxyl, alkoxyl, hydroxyalkoxyl, acyloxy-, aryl, or heteroaryl moiety, etc.). Illustrative examples include compounds of formula (e) in which J is selected from the following:

In this class, each $R^5$ is independently selected and is H or an aliphatic, heteroaliphatic, aryl, or heteroaryl moiety (which moiety may be substituted or unsubstituted), especially lower (i.e. from 1 to 6 carbons) aliphatic moiety including lower alkyl, which may be optionally substituted (e.g. with a hydroxyl, alkoxyl, hydroxyalkoxyl, acyloxy-, aryl, or heteroaryl moiety, etc.). Illustrative examples include compounds of formula (f) in which J is selected from the following:

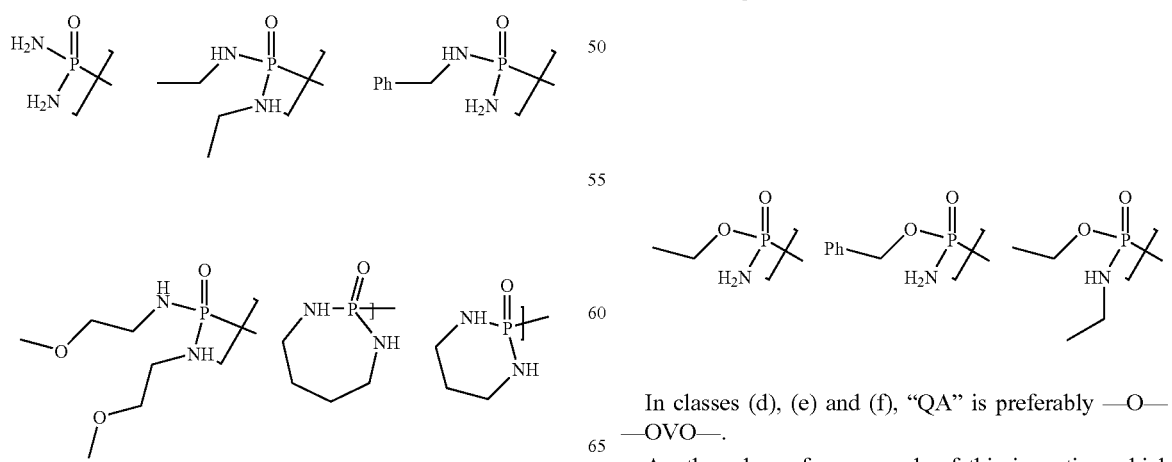

In classes (d), (e) and (f), "QA" is preferably —O— or —OVO—.

Another class of compounds of this invention which is also of interest is illustrated by formula (g):

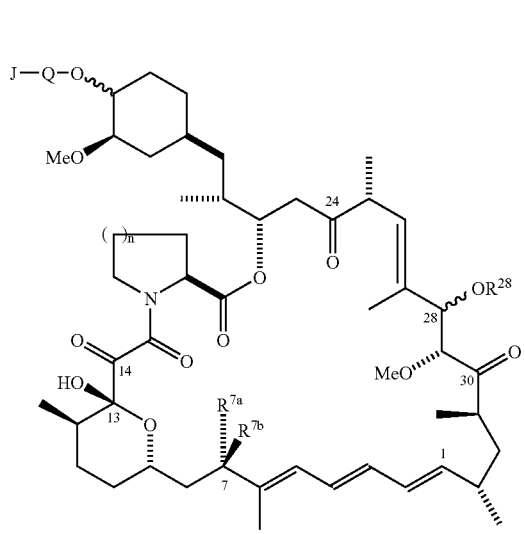

(g)

where J, Q, n and the various R groups are as previously defined, and with the proviso noted previously. This class encompasses a number of subclasses of interest, including the following:

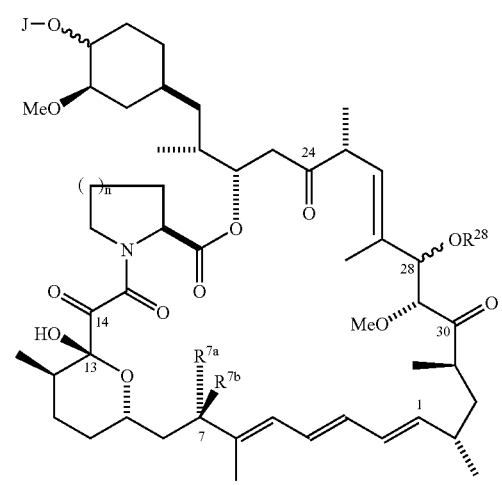

(g)(i)

in which Q is absent, i.e., in which J is linked (i.e., covalently bonded) to the cyclohexyl ring via an oxygen. This subclass (which excludes O-phosphorylated rapamycin itself and the salts or methyl phosphodiester thereof) includes compounds comprising any moiety, J, as previously defined, including all of the types of J moieties illustrated elsewhere in this document, including those shown in the various compounds, types of compounds and illustrative J moieties disclosed herein, including among others the following illustrative examples:

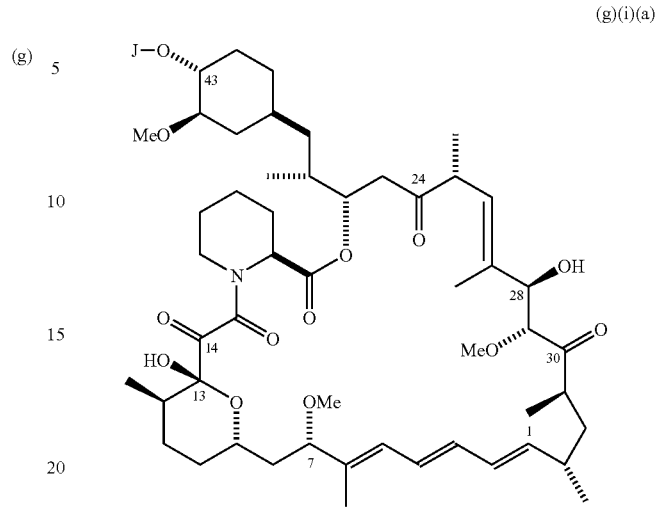

(g)(i)(a)

where J is selected from:
— P(O)Me$_2$, — P(O)Ph$_2$, — P(O)(OMe)(Me),
— P(O)(OnPr)(Me), — P(O)(OiPr)(Me), — P(O)(OnBu)(Me),
— P(O)(Me)(OCH$_2$CH$_2$OMe), — P(O)(Me)(OCH$_2$CH$_2$OEt),
— P(O)(Me)(OCH$_2$CH$_2$OCH$_2$CH$_2$OH), — P(O)(OMe)(Et),
— P(O)(CH$_2$CH$_2$CH$_2$OH)$_2$, — P(O)(OEt)$_2$, — P(O)(NH$_2$)$_2$,
— P(O)(OH)—CH$_2$—PO(OH)$_2$, In compounds of the structure shown in "(g)(i)(a)", J is a moiety other than —PO$_3$H$_2$, a salt thereof, or —PO$_3$Me$_2$. Those choices for the subsituent, J, are permitted only in combination with one or more additional structural changes relative to rapamycin, e.g. altered stereochemistry at one or more sites including C43 or C28, modification in the substituent or stereochemistry at C7, reduction of one or more of the ketone functionalities, demethylation at one or more sites, etc. Thus the following compounds, among others, are of interest:

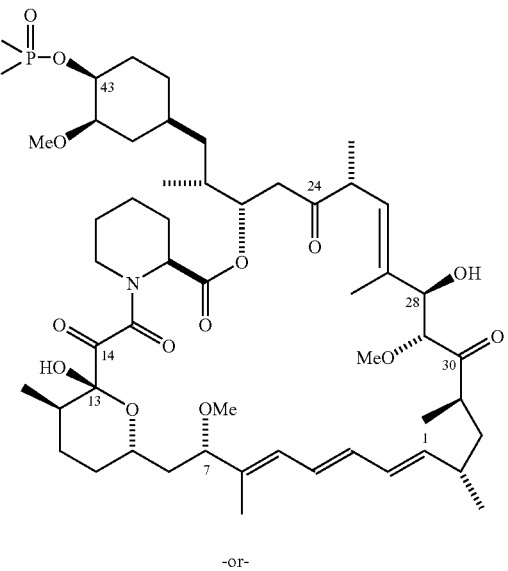

-or-

-continued

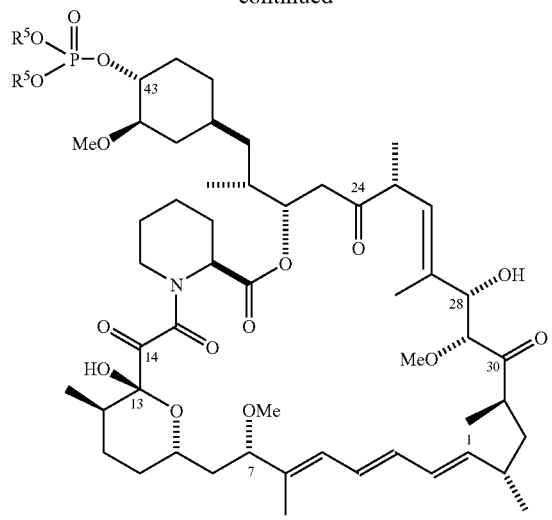

wherein R⁵ is H or lower alkyl, including, among others, methyl.

Also of particular interest is the subclass of compounds, (g)(ii), which differs from subclass (g)(i)(a) in one or more of the following respects: (a) the substituent at position 28 is epimerized (relative to the orientation of rapamycin's C28 —OH), (b) one or both ketones at positions 24 and 30 are reduced to hydroxyl groups, (c) the methoxyl group at position 7 is replaced by H or by one of the various C7 substituents listed elsewhere, and (d) the substituent J-O— at position 43 is in the epimeric orientation (relative to the orientation of rapamycin's C43 —OH). Again, J is any of the phosphorus-containing moieties as previously described.

Another subclass of interest is depicted below in (g)(iii) to illustrate compounds with an O-linked J moiety in which Q is present. This subclass illustrates the case in which Q is —OV— where V is an aliphatic moiety.

(g)(iii)

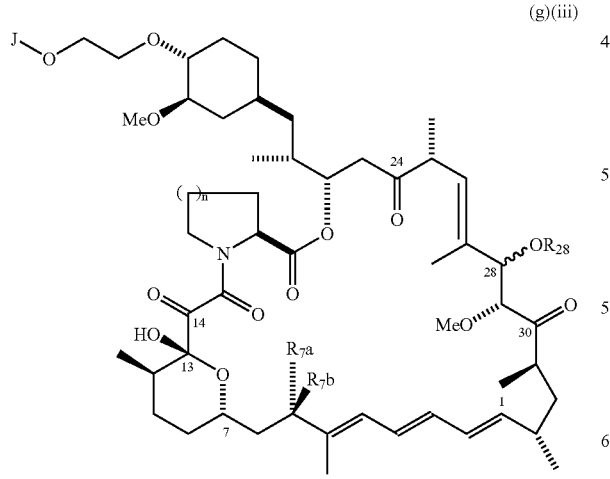

where J is selected from:
—P(O)Me₂, —P(O)Ph₂, —P(O)(OMe)(Me),
—P(O)(OnPr)(Me), —P(O)(OiPr)(Me), —P(O)(OnBu)(Me),
—P(O)(Me)(OCH₂CH₂OMe), —P(O)(Me)(OCH₂CH₂OEt),
—P(O)(Me)(OCH₂CH₂OCH₂CH₂OH), —P(O)(OMe)(Et),
—P(O)(CH₂CH₂OH)₂, —P(O)(OEt)₂, —P(O)(NH₂)₂.

Another class of compounds of this invention which is also of interest is illustrated by the compounds in which A is —NR²— as depicted in formula (h):

(h)

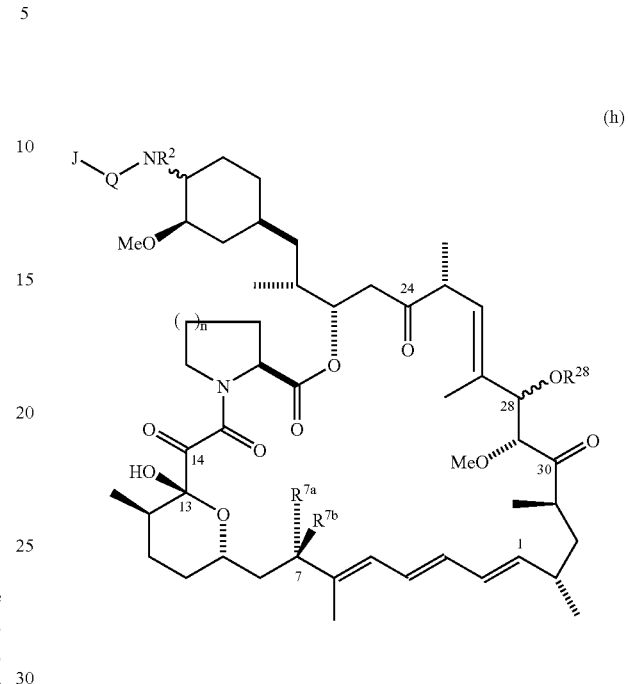

This class includes the subclass in which Q is absent, i.e., in which J is linked (i.e., covalently bonded) to the cyclohexyl ring via a nitrogen as illustrated below:

(h)(i)

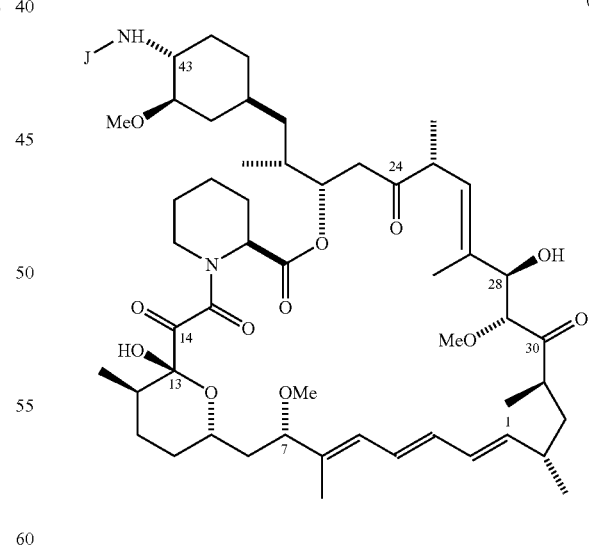

where J is selected from:
—P(O)Me₂, —P(O)Ph₂, —P(O)(OMe)(Me),
—P(O)(OnPr)(Me), —P(O)(OiPr)(Me), —P(O)(OnBu)(Me),
—P(O)(Me)(OCH₂CH₂OMe), —P(O)(Me)(OCH₂CH₂OEt),
—P(O)(Me)(OCH₂CH₂OCH₂CH₂OH), —P(O)(OMe)(Et),
—P(O)(CH₂CH₂OH)₂, —P(O)(OEt)₂, —P(O)(NH₂)₂, Another subclass of class (h) of interest is illustrated below by rapamycin derivatives in which Q is present and comprises an aliphatic or heteroaliphatic moiety, V, which may be substituted or unsubstituted, where each of the variable moieties are as previously defined or otherwise exemplified herein:

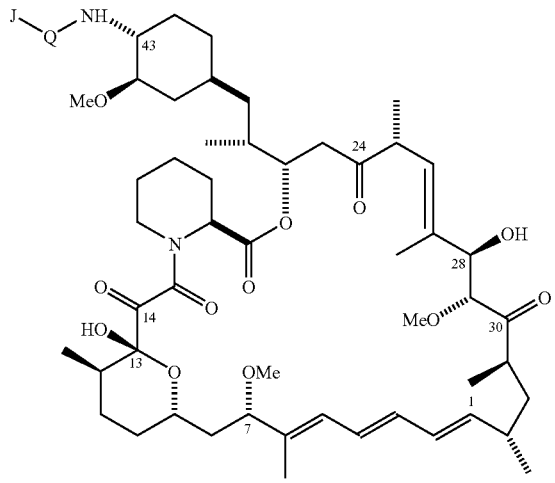

(h)(ii)

where JQ- is J—OCH$_2$CH$_2$NH—, J—CH$_2$CH$_2$NH—, J—OCH$_2$CH$_2$OCH$_2$CH$_2$NH— or J—OCH(CH$_3$)CH$_2$NH—.

Another class of compounds of this invention which is also of interest is illustrated by formula (i):

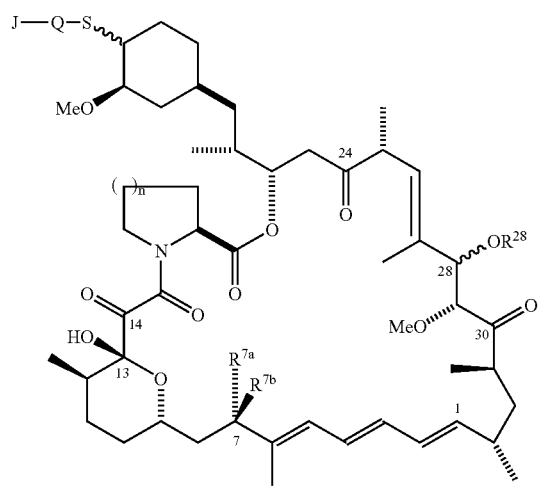

(i)

where J, Q, n and the various R groups are as previously defined. This class encompasses a number of subclasses of interest, including the following:

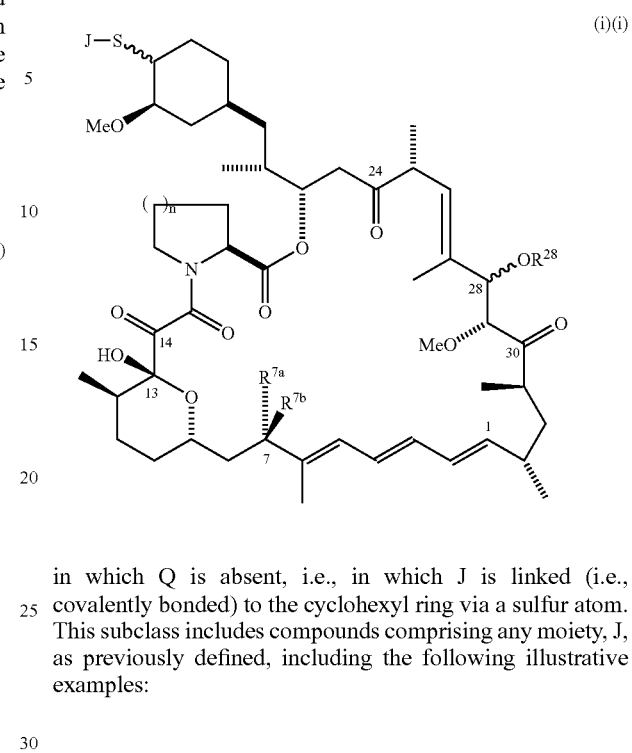

(i)(i)

in which Q is absent, i.e., in which J is linked (i.e., covalently bonded) to the cyclohexyl ring via a sulfur atom. This subclass includes compounds comprising any moiety, J, as previously defined, including the following illustrative examples:

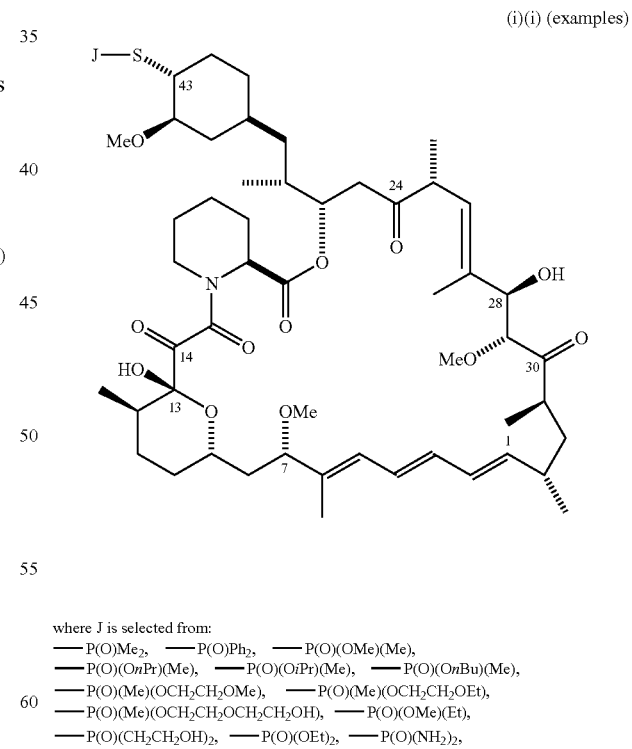

(i)(i) (examples)

where J is selected from:
—P(O)Me$_2$, —P(O)Ph$_2$, —P(O)(OMe)(Me),
—P(O)(OnPr)(Me), —P(O)(OiPr)(Me), —P(O)(OnBu)(Me),
—P(O)(Me)(OCH$_2$CH$_2$OMe), —P(O)(Me)(OCH$_2$CH$_2$OEt),
—P(O)(Me)(OCH$_2$CH$_2$OCH$_2$CH$_2$OH), —P(O)(OMe)(Et),
—P(O)(CH$_2$CH$_2$OH)$_2$, —P(O)(OEt)$_2$, —P(O)(NH$_2$)$_2$, Another subclass of interest is depicted below in (i)(ii) which illustrates some compounds with an O-linked J moiety in which Q is present. This subclass illustrates the case in which Q is —SV— where V is an aliphatic moiety.

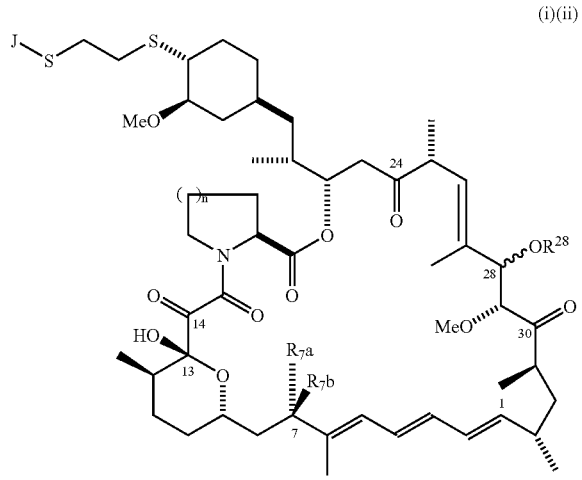

(i)(ii)

where J is selected from:
— P(O)Me$_2$, — P(O)Ph$_2$, — P(O)(OMe)(Me),
— P(O)(OnPr)(Me), — P(O)(OiPr)(Me), — P(O)(OnBu)(Me),
— P(O)(Me)(OCH$_2$CH$_2$OMe), — P(O)(Me)(OCH$_2$CH$_2$OEt),
— P(O)(Me)(OCH$_2$CH$_2$OCH$_2$CH$_2$OH), — P(O)(OMe)(Et),
— P(O)(CH$_2$CH$_2$OH)$_2$, — P(O)(OEt)$_2$, — P(O)(NH$_2$)$_2$, Additional classes of compounds of the invention of particular interest are noted below:

(j) Compounds of FIG. 1, in which JQA- replaces the C-43 hydroxyl group of rapamycin, with conservation of stereochemistry at C43 relative to rapamycin, where JQA is as defined above, with the proviso noted at the outset. Such compounds can be prepared from rapamycin as disclosed in detail below.

(k) Compounds as in class (j), but with one or more additional structural modifications relative to rapamycin. Numerous such modifications are known in the art and are alluded to elsewhere herein, including replacement of the —OMe substituent at C7, or alteration of its stereochemistry; epimerization at one or both of C28 and C43; reduction of one or more of the ketone functionalities e.g. at one or both of ring positions 24 and 30; desmethylation at one or more sites; reduction of one or more of the double bonds between C1 and C6; and/or use of the prolyl analog instead of the pipicolate structure of rapamycin. Compounds of this invention may be prepared in some cases by starting with the appropriate rapamycin analog in place of rapamycin itself and in other cases by effecting the desired additional transformation on the appropriate JQA-containing rapalog.

(l) Compounds of this invention in which J is other than —PO$_3$H$_2$, a salt thereof, or a dialkyl phosphate (such as —PO$_3$Me$_2$, for example).

(m) Compounds of the invention with a molecular weight below 1700, preferably below 1400, and more preferably below 1200 mass units (not counting the contribution of a counter ion in cases in which the compound is in a salt form).

(n) Compounds of the invention which are chemically linked to a polyethylene glycol moiety or other solubility-enhancing group. Examples include glycinate (or other aminocarboxylate) esters or PEGylated esters (see e.g. WO 02/24706, the contents of which are incorporated herein by reference) of any free —OH moiety of a rapalog of this invention.

(o) Compounds of the invention that retain at least 0.01, preferably 0.1 and more preferably at least 0.5 times the potency of rapamycin in a T cell proliferation assay (e.g., which have an IC50 value less than 100-fold, preferably less than 10-fold, and more preferably less than 2-fold worse than that of rapamycin).

(p) Compounds of the formula:

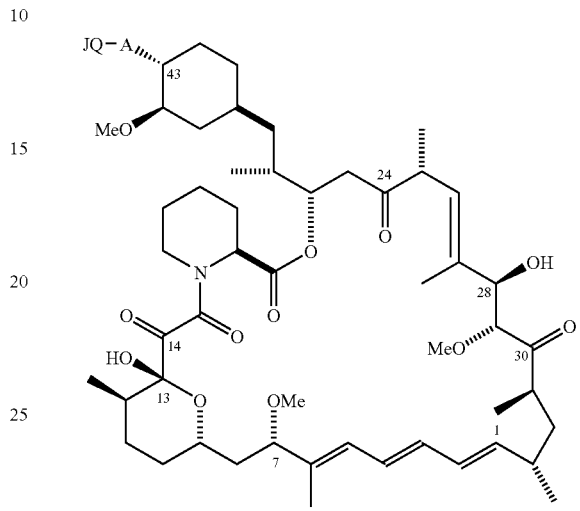

and pharmaceutically acceptable derivatives thereof, wherein A is —O—, —S— or —NR$^2$— or is absent (i.e., or is a covalent bond linking JQ to C-43); Q is absent (i.e., is a covalent bond) or (if A is —O—, —S— or —NR$^2$—) Q may be —V—, —OV—, —SV—, or —NR$^2$V—, where V is an aliphatic, heteroaliphatic, aryl, or heteroaryl moiety, such that J is linked to the cyclohexyl ring directly, through A or through VA, OVA, SVA or NR$^2$VA; K is O or S;

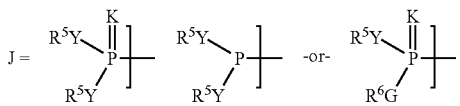

each occurrence of Y is independently —O—, —S—, —NR$^2$—, or a bond linking a R moiety to P; each occurrence of R$^2$ and R$^5$ is independently an aliphatic, heteroaliphatic, aryl, or heteroaryl moiety, or H; and each occurrence of R$^6$ is independently —PK(YR$^5$)(YR$^5$), —SO$^2$(YR$^5$) or —C(O)(YR$^5$); so long as any R$^2$ or R$^5$ moiety linked directly to P is not H; wherein two R$^2$, R$^5$ and/or R$^6$ moieties may be chemically linked to one another to form a ring; each occurrence of G is independently —O—, —S—, —NR$^2$—, or (M)$_x$; each occurrence of M is independently a substituted or unsubstituted methylene moiety, and any M-M' moiety may be saturated or unsaturated; each occurrence of x is independently an integer from 1–6; wherein each of the foregoing aliphatic and heteroaliphatic moieties is independently linear or branched, or cyclic or acyclic, and substituted or unsubstituted, and each of the aryl, heteroaryl, acyl, aroyl or heteroaroyl moieties is independently substituted or unsubstituted;

with the proviso that: J-Q-A- is not (HO)$_2$(P=O)O— or (MeO)$_2$(P=O)O—, or (HO)$_2$(P=O)—W—O— (or a desmethyl or reduced analog of such (HO)$_2$(P=O)—W—O-containing rapamycin derivative, where W comprises a substituted or unsubstituted heterocycle comprising

alone or fused to a six-membered aromatic ring, wherein U is substituted or unsubstituted amino, O, S, SO or SO$_2$; or a salt of any of the foregoing; and if JQA- is (R$^2$Y)(Me)(P=O)O—, then (R$^2$Y) is not an immunogenic carrier material, detector carrier material or a solid matrix or salt thereof (e.g., as in embodiments in which R$^2$ in that R$^2$Y group has 15 or fewer, preferably 10 or fewer, and optimally 6 or fewer carbon atoms).

(q) Compounds of the formula:

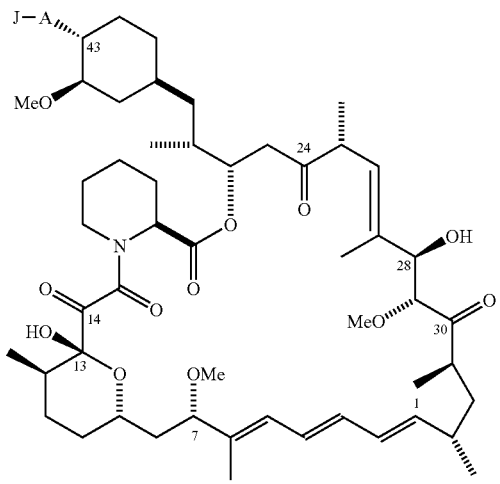

and pharmaceutically acceptable derivatives thereof, wherein A, J, K and the other variable groups are as defined in (p), except in these compounds, with the proviso that (a) J-A- is not (HO)$_2$(P=O)O— or (MeO)$_2$(P=O)O—, and (b) if JA- is (R$^2$Y)(Me)(P=O)O—, then (R$^2$Y) is not an immunogenic carrier material, detector carrier material or a solid matrix matrix or salt thereof (e.g., as in embodiments in which R$^2$ in that R$^2$Y group has 15 or fewer, preferably 10 or fewer, and optimally 6 or fewer carbon atoms) (instead of the proviso in the case of (p).

(r) A compound of the formula:

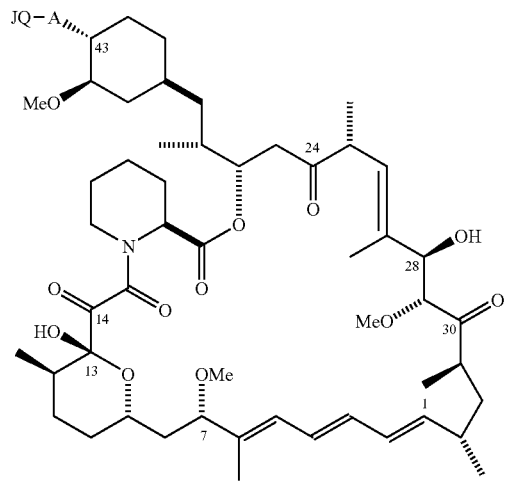

and pharmaceutically acceptable derivatives thereof, wherein J is chosen from:

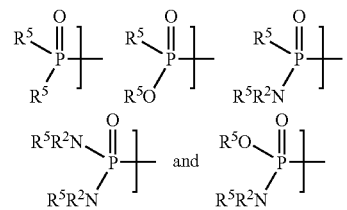

wherein the various variable groups are as otherwise defined above in (p) and (q) except that each occurrence of R$^2$ and R$^5$ is an independently chosen lower aliphatic or aryl moiety, which may be substituted or unsubstituted (except that in addition, each —OR$^5$ and —NR$^2$R$^5$ may be —OH and —NHR$^5$, respectively);

and with the proviso that if J-Q-A- is (R$^2$Y)(Me)(P=O)O—, then (R$^2$Y) is not an immunogenic carrier material, detector carrier material or a solid matrix, or a salt thereof.

(s) Compounds of the formula:

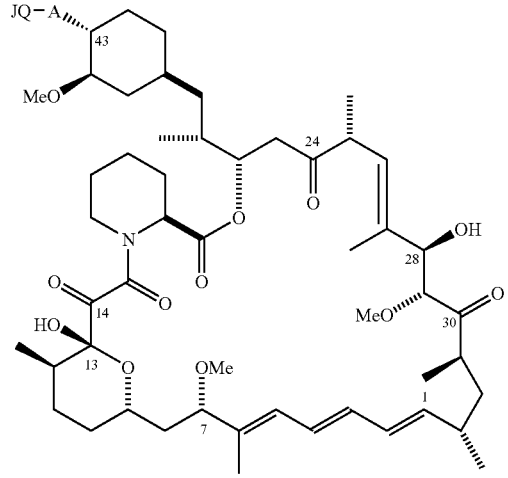

and pharmaceutically acceptable derivatives thereof, wherein J is chosen from:

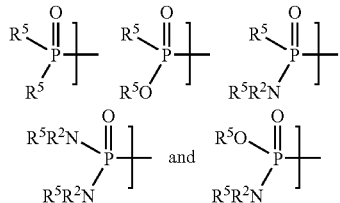

A is absent or is —O—, —S— or —NR$^2$—; Q is absent or (if A is —O—, —S— or —NR$^2$—) Q may be —V—, —OV—, —SV—, or —NR$^2$V—, where V is an aliphatic, heteroaliphatic, aryl, or heteroaryl moiety, such that J is linked to the cyclohexyl ring directly, through A or through VA, OVA, SVA or NR$^2$VA;

each occurrence of R$^2$ and R$^5$ is an independently chosen lower aliphatic or aryl moiety, which may be substituted or unsubstituted, except that in addition, —OR$^5$ and —NR$^2$R$^5$, may be —OH and —NHR$^5$; with the proviso that if J-Q-A- is (R$^2$Y)(Me)(P=O)O—, then (R$^2$Y) contains 15 or fewer carbon atoms;

two R$^2$, R$^5$ and/or R$^6$ moieties may optionally be chemically linked to one another to form a ring;

and each of the foregoing aliphatic and heteroaliphatic moieties is independently linear or branched, or cyclic or acyclic, and substituted or unsubstituted, and each of the aryl, heteroaryl, acyl, aroyl or heteroaroyl moieties is independently substituted or unsubstituted;

(t) Compounds of types (p) through (s) in which each occurrence of R$^2$ and R$^5$ is an independently chosen C1–C6 alkyl group optionally bearing one or more halo, —OH, alkoxyl-, alkyloxyalkyloxy-, haloalkyl-, hydroxyalkoxyl-, acyl-, acyloxy-, hetrocyclic, aryl or heteroaryl substituents, except that in addition, each —OR$^5$ and —NR$^2$R$^5$ may be —OH and —NHR$^5$ respectively.

(u) Compounds of type (t) in which each occurrence of R$^2$ and R$^5$ is independently chosen from methyl, ethyl, n-propyl, -propyl, n-butyl, 2-butyl, t-butyl, phenyl, or heteroaryl, each of which optionally bearing one or more halo, —OH, alkoxyl-, alkoxylalkoxyl-, haloalkyl-, hydroxyalkoxyl-, acyl-, acyloxy-, heterocyclic, aryl or heteroaryl substituents, and in addition, each —OR$^5$ and —NR$^2$R$^5$ may be —OH and —NHR$^5$ respectively.

(v) Compounds of types (p) through (u) in which the R$^2$ and R$^5$ moieties of J are aliphatic groups with up to 8 carbon atoms which may be optionally substituted, e.g. as illustrated by the following J groups:

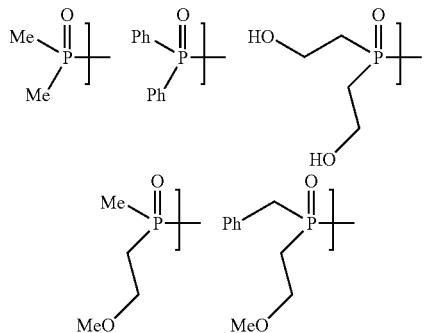

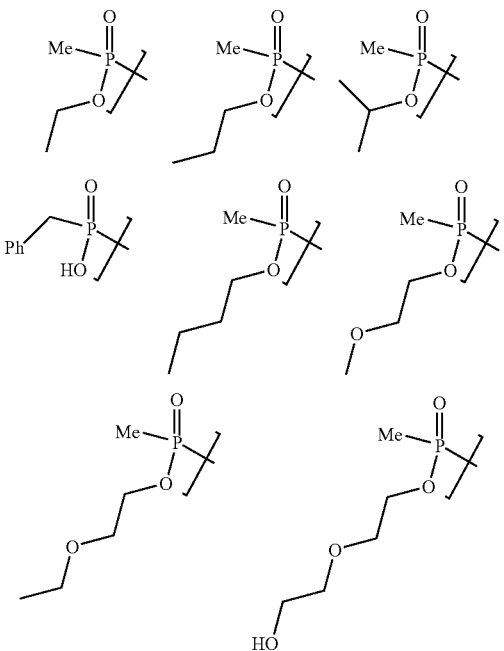

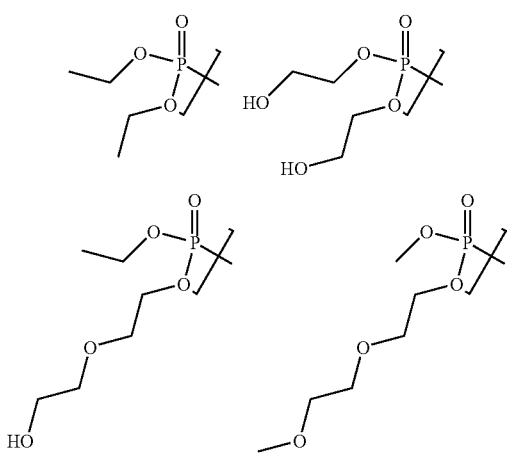

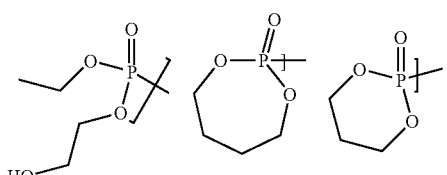

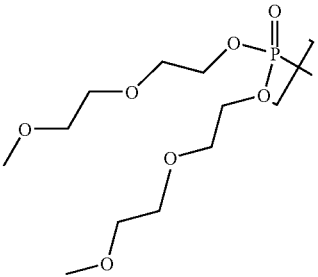

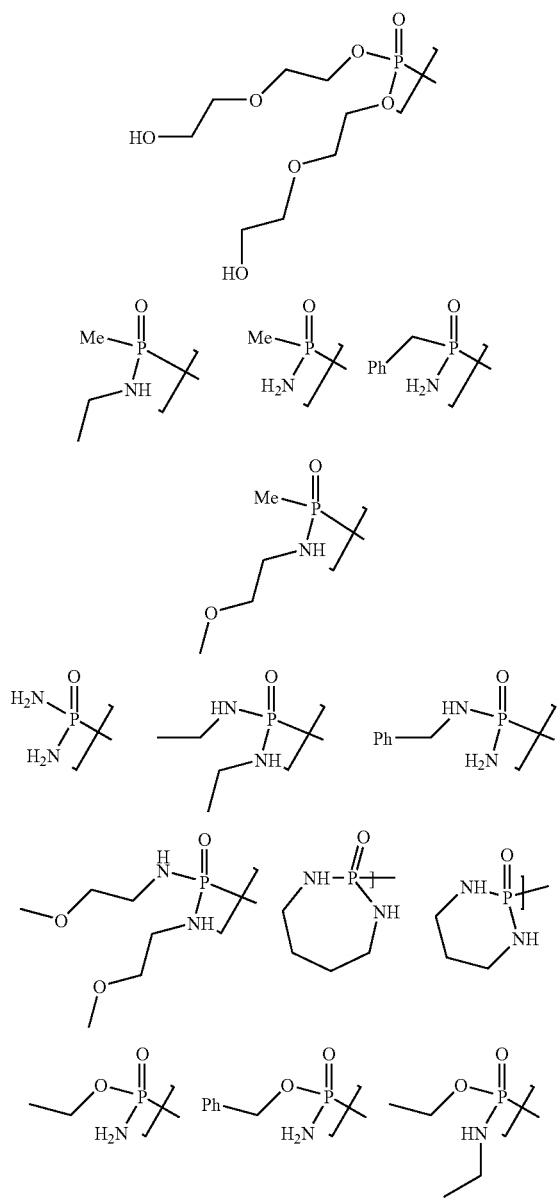

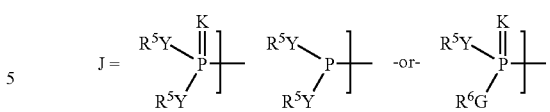

each occurrence of Y is independently —O—, —S—, —NR²—, or a bond linking a R⁵ moiety to P;

each occurrence of R² and R⁵ is independently an aliphatic, heteroaliphatic, aryl, or heteroaryl moiety, or H; and each occurrence of R⁶ is independently —PK(YR⁵)(YR⁵), —SO²(YR⁵) or —C(O)(YR⁵); so long as any R² or R⁵ moiety linked directly to P is not H; wherein two R², R⁵ and/or R⁶ moieties may be chemically linked to one another to form a ring;

each occurrence of G is independently —O—, —S—, —NR²— or $(M)_x$;

each occurrence of M is independently a substituted or unsubstituted methylene moiety, and any M-M' moiety may be saturated or unsaturated;

each occurrence of x is independently an integer from 1–6;

wherein each of the foregoing aliphatic and heteroaliphatic moieties is independently linear or branched, or cyclic or acyclic, and substituted or unsubstituted, and each of the aryl, heteroaryl, acyl, aroyl or heteroaroyl moieties is independently substituted or unsubstituted;

with one or more of the following additional features:

(1) epimerization at position 28, or replacement of the position 28 hydroxyl group (in either sterochemical orientation) with halo, —OR² or —OC(=O)AR²;

(2) replacement of the ketone at position 24 with a substituted or unsubstituted oxime, or with a hydroxyl group or derivative thereof of the formula —OR² or —OC(=O)AR²;

(3) replacement of the ketone at position 24 with a substituted or unsubstituted oxime, or with a hydroxyl group or derivative thereof of the formula —OR² or —OC(=O)AR²;

(4) epimerization of the —OMe at position 7 and/or replacement of the —OMe with a moiety selected from H, halo, —R⁴, —OR⁴, —SR⁴, —OC(O)R⁴, —OC(O)NR^A R^B, —NR^A R^B, —NR^B C(O)R⁴, —NR^B C(O)OR⁴, —NR^B SO2R⁴ or —NR^B SO2NR^A R^B'; where R⁴ is R² and where R^B is OH or R²; and (5) elimination of the —OMe at position 7 yielding the tetra-ene moiety:

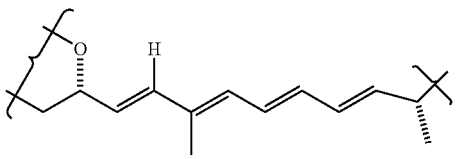

(w) Compounds of types (p) (s) (t) (u) or (v) in which QA is —O—, —OVO—, —NH—, —OVNH—, —S—, or —SVS—, where V is a lower aliphatic moiety.

(x) Compounds of all of the foregoing types in which JQA- or JA- comprises a group (R²Y)(Me)(P=O)O— in which R²Y— contains 15 or fewer, preferably 10 or fewer, and more preferably 8 or fewer carbon atoms.

(y) Compounds comprising a derivative of rapamycin or 43-epi-rapamycin in which the hydroxyl group at position 43 is replaced by a group JQA- in which A is —O—, —S— or —NR²— or is absent; Q is absent or (if A is —O—, —S— or —NR²—) Q may be —V—, —OV—, —SV—, or —NR²V—, where V is an aliphatic, heteroaliphatic, aryl, or heteroaryl moiety, such that J is linked to the cyclohexyl ring directly, through A or through VA, OVA, SVA or NR²VA; K is O or S;

(z) Compounds of type (y) in which each occurrence of R² and R⁵ is an independently chosen C1–C6 alkyl group optionally bearing one or more halo, —OH, alkoxyl-, alkyloxyalkyloxy-, haloalkyl-, hydroxyalkoxyl-, acyl-, acyloxy-, hetrocyclic, aryl or heteroaryl substituents, except that in addition, —OR⁵ and —NR²R⁵, may be —OH and —NHR⁵. For instance, in some cases, each occurrence of R² and R⁵ is independently chosen from methyl, ethyl, n-propyl, -propyl, n-butyl, 2-butyl, t-butyl, phenyl or heteroaryl, each of which optionally bearing one or more of the foregoing types of substituents or other substituents as disclosed herein.
(aa) Compounds of type (y) or (z) in which QA is —OVO—, —OVNH— or —SVS—, where V is a lower aliphatic moiety.
(ab) Compounds of type (y) or (z) containing a moiety J as described in conection with compounds of type (v).

One class of compounds that are not within the invention are conjugates or rapamycin, or derivatives thereof, comprising a substituent on the oxygen at position 43 which comprises —P(O)(Me)(Z) where Z is a immunogenic carrier material, detector carrier material or a solid matrix, or a salt thereof, linked to the P via a carbonyl, —NH—, —S—, —O— or certain aliphatic groups such as disclosed in US 2001/0010920 A1. That document discloses conjugates of rapamycin with such carriers or matrices for use in generating and detecting antibodies, for measuring levels of rapamycin iand for isolating rapamycin binding proteins. As disclosed in that document, the immunogenic carrier material can be selected from any conventionally known immunogenic carrier material, and will usually a protein or polypeptide, and in some cases could be a sufficiently large and immunogenic carbohydrate, polysaccharide, lipopolysaccharide, or nucleic acid; immunogenic proteins and polypeptides will have molecular weights between 5,000 and 10,000,000, preferably greater than 15,000 and more usually greater than 40,000; examples included albumins, globulins, enzymes, hemocyanins, glutelins or proteins having significant non-proteinaceous constituents, e.g., glycoproteins; the detector carrier material can be an enzyme such as horseradish peroxidase, alkaline phosphatase, luciferase, a fluorescent moiety such as fluorescein, Texas Red, or rhodamine, a chemiluminescent moiety, and the like; the solid matrix carrier material can be resin beads, an ELISA plate, glass beads as commonly used in a radioimmunoassay, plastic beads, or solid matrix material typically used in a dipstick-type assay.

Some other aspects of the invention include:

A composition comprising a compound of the invention, including any of the various types of compounds noted above, together with a pharmaceutically acceptable vehicle and optionally containing one or more pharmaceutically acceptable excipients. The composition may be one which is suitable for oral or parenteral administration to a subject, e.g. a mammalian subject, including a human patient.

Compositions may be prepared using conventional materials such that they are suitable for administration by any desired route of administration, examples of which are noted in this document.

The use of a compound of this invention to prepare a composition useful for any of the various medical and other uses noted herein.

A method for suppressing the immune response of a subject by administering to the subject an immunosuppressive amount (i.e., an immunosuppressive treatment course involving periodic administration) of one of the foregoing compositions, for instance as a method treating or suppressing the rejection of transplanted tissues in a recipient.

A method for treating graft vs. host disease, lupus, rheumatoid arthritis, diabetes mellitus, myasthenia gravis, multiple sclerosis, psoriasis, dermatitis, eczema, seborrhea, inflammatory bowel disease, pulmonary inflammation, ocular uveitis; adult T-cell leukemia/lymphoma; fungal infections; hyperproliferative restenosis; graft vascular atherosclerosis; cerebral vascular disease, coronary artery disease, cerebrovascular disease, arteriosclerosis, atherosclerosis, nonatheromatous arteriosclerosis, or vascular wall damage from cellular events leading toward immune mediated vascular damage, stroke or multiinfarct dementia in a subject in need thereof, by administering to such a subject a therapeutically effective amount of a composition containing a compound of the invention.

A method for treating coronary artery disease, cerebrovascular disease, arteriosclerosis, atherosclerosis, nonatheromatous arteriosclerosis, vascular wall damage from cellular events leading toward immune mediated vascular damage, stroke or multiinfarct dementia in a subject in need thereof, the method comprising administering to the subject a composition containing a compound of this invention, alone or in combination with treatment with one or more other therapeutic agents as are noted elsewhere herein, including among others an ACE inhibitor (such as quinapril, perindopril, ramipril, captopril, trandolapril, fosinopril, lisinopril, moexipril, and enalapril); angiotensin II receptor antagonist (such as candesartan, irbesartan, losartan, valsartan, and telmisartan); fibric acid derivative (such as clofibrate, and gemfibrozil); HMG Co-A reductase inhibitor (such as cerivastatin, fluvastatin, atorvastatin, lovastatin, pravastatin, or simvastatin); beta adrenergic blocking agent (such as sotalol, timolol, esmolol, carteolol, propranolol, betaxolol, penbutolol, nadolol, acebutolol, atenolol, metoprolol, and bisoprolol); calcium channel blocker (such as nifedipine, verapamil, nicardipine, diltiazem, nimodipine, amlodipine, felodipine, nisoldipine, and bepridil); antioxidant; anticoagulant (such as warfarin, dalteparin, heparin, enoxaparin, and danaparoid); or agent useful in hormone replacement therapy containing estrogens (such as conjugated estrogens, ethinyl estradiol, 17-beta-estradiol, estradiol, and estropipate). The additional agent or agents, in this and other cases herein, may be provided before or after or concurrent with administration of a compound of this invention.

A method for treating cancer in a subject in need thereof, which comprises administering to the subject a treatment effective amount of a composition containing a compound of this invention. Various cancers which may be thus treated are noted below and elsewhere herein. This treatment may be provided in combination with one or more other cancer therapies, such as in combination with the administration to the subject of one or more of an anti-cancer alkylating or intercalating agent; an antiestrogen; an inhibitor of a kinase (e.g., Src, BRC/Abl, kdr, aurora-2, glycogen synthase kinase 3 ("GSK-3")); an antibody to a receptor or hormone implicated in a cancer (e.g. EGFR, PDGFR, IGF-R and IL-2);, or a soluble receptor or other receptor antagonist to such receptor; a proteasome inhibitor or other NF-kB inhibitor; or radiation. Examples of other thereapeutic agents are noted elsewhere herein and include among others, Zyloprim, alemtuzmab, altretamine, amifostine, nastrozole, antibodies against prostate-specific membrane antigen (such as MLN-591, MLN591RL and MLN2704), arsenic trioxide, Avastin® (or other anti-VEGF antibody), bexarotene, bleomycin, busulfan, capecitabine, carboplatin, Gliadel Wafer, celecoxib, chlorambucil, Cl-1033 (Pfizer's pan-EGF-R inhibitor; or other EGF-R inhibitor), cisplatin, cisplatin-epinephrine gel, cladribine, cytarabine liposomal, daunorubicin liposomal, daunorubicin, daunomycin, dexrazoxane, docetaxel, doxorubicin, Elliott's B Solution, epirubicin, estramustine, etoposide phosphate, etoposide, exemestane, fludarabine, 5-FU, fulvestrant, gemcitabine, gemtuzumab-ozogamicin, goserelin acetate, hydroxyurea, idarubicin, idarubicin, Idamycin, ifosfamide, imatinib mesylate, irinotecan (or other topoisomerase inhibitor, including antibodies such as MLN576 (XR11576)), letrozole, leucovorin, leucovorin levamisole,liposomal daunorubicin, melphalan, L-PAM, mesna, methotrexate, methoxsalen, mitomycin C, mitoxantrone, MLN518 or MLN608 (or other inhibitors of the flt-3 receptor tyrosine kinase, PDFG-R or c-kit), itoxantrone, paclitaxel, Pegademase, pentostatin, porfimer sodium, Rituximab (RITUXAN®), talc, tamoxifen, temozolamide, teniposide, VM-26, topotecan, toremifene, Trastuzumab (Herceptin®, or other anti-Her2 antibody), 2C4 (or other antibody which interferes with HER2-mediated signaling), tretinoin, ATRA, valrubicin, vinorelbine, or pamidronate, zoledronate or another bisphosphonate.

A partial list of cancers includes the following: A partial list of cancers, primary or otherwise, of men, women, adults and children includes the following: Adrenocortical Carcinoma; AIDS-Related Lymphoma; AIDS-Related Malignancies; Anal Cancer; Bile Duct Cancer, Extrahepatic; Bladder Cancer; Bone Cancer, Osteosarcoma/Malignant Fibrous Histiocytoma; cancers of the brain including among others Brain Stem Glioma; Cerebellar Astrocytoma, Cerebral Astrocytoma/Malignant Glioma, Ependymoma, Medulloblastoma, Supratentorial Primitive Neuroectodermal Tumors, and Visual Pathway and Hypothalamic Glioma; Breast Cancer; Bronchial Adenomas/Carcinoids; Gastrointestinal Carcinoid Tumor; the various Carcinomas including Adrenocortical, Islet Cell and adenocarcinoma as well as Carcinoma of Unknown Primary; Central Nervous System Lymphoma; Cervical Cancer; other Childhood Cancers; Clear Cell Sarcoma of Tendon Sheaths; Colon Cancer; Colorectal Cancer; Cutaneous T-Cell Lymphoma; Endometrial Cancer; Ependymoma; Ovarian Epithelial Cancer; Esophageal Cancer; Ewing's Family of Tumors; Extracranial Germ Cell Tumor; Extragonadal Germ Cell Tumor; Extrahepatic Bile Duct Cancer; Eye Cancer, Intraocular Melanoma; Retinoblastoma; Gallbladder Cancer; Gastric (Stomach) Cancer; Gastrointestinal Carcinoid Tumor; Germ Cell Tumor s including e.g., Extracranial, Extragonadal, and Ovarian; Gestational Trophoblastic Tumor; Hairy Cell Leukemia; Head and Neck Cancer; Hepatocellular (Liver) Cancer; Hodgkin's Disease; Hypopharyngeal Cancer; Islet Cell Carcinoma (Endocrine Pancreas); Kaposi's Sarcoma; Kidney Cancer; Laryngeal Cancer; Leukemias including e.g., Acute Lymphoblastic, Acute Myeloid, Chronic Lymphocytic, Chronic Myelogenous and Hairy Cell leukemias; Lip and Oral Cavity Cancer; Liver Cancer; Non-Small Cell and Small Cell Lung Cancer; the various Lymphomas, including e.g., AIDS-Related, Central Nervous System and Cutaneous T cell-Lymphomas as well as Hodgkin's Disease, Non-Hodgkin's lymphoma, and Central Nervous System lymphoma; Waldenstrom's Macroglobulinemia; Malignant Mesothelioma; Malignant Thymoma; Medulloblastoma; Melanoma; Intraocular Melanoma; Merkel Cell Carcinoma; Mesothelioma, Malignant; Metastatic Squamous Neck Cancer with Occult Primary; Multiple Endocrine Neoplasia Syndrome; Multiple Myeloma/Plasma Cell Neoplasm; Mycosis Fungoides; Myelodysplastic Syndrome; Multiple Myeloma; Myeloproliferative Disorders; Nasal Cavity and Paranasal Sinus Cancer; Nasopharyngeal Cancer; Neuroblastoma; Oral Cancer; Oral Cavity and Lip Cancer; Oropharyngeal Cancer; Osteosarcoma/Malignant Fibrous Histiocytoma of Bone; Ovarian Cancer; Ovarian Epithelial Cancer; Ovarian Germ Cell Tumor; Ovarian Low Malignant Potential Tumor; Pancreatic Cancer; Islet Cell Cancer; Paranasal Sinus and Nasal Cavity Cancer; Parathyroid Cancer; Penile Cancer; Pheochromocytoma; Pineal and Supratentorial Primitive Neuroectodermal Tumors; Pituitary Tumor; Plasma Cell Neoplasm/Multiple Myeloma; Pleuropulmonary Blastoma; Prostate Cancer; Rectal Cancer; Renal Cell (Kidney) Cancer (including among others progressive metastatic renal cell carcinoma (including among others clear cell and the collecting duct hamartoma variant); Renal, Pelvis and Ureter Transitional Cell Cancers; Retinoblastoma; Rhabdomyosarcoma; Salivary Gland Cancer; Kaposi's; Sarcoma (Osteosarcoma)/Malignant Fibrous Histiocytoma of Bone; Soft Tissue Sarcoma (including among others malignant mixed mullerian, liposarcoma and GIST); Sezary Syndrome; Skin Cancer, including melanomas and Merkel Cell cancer; Small Intestine Cancer; Soft Tissue Sarcoma; Squamous Neck Cancer; Stomach (Gastric) Cancer (including among others progressive metastatic GIST); Supratentorial Primitive Neuroectodermal Tumors; Testicular Cancer; Thymoma; Thyroid Cancer; Transitional Cell Cancer of the Renal Pelvis and Ureter; Gestational Trophoblastic Tumor; Cancers of an Unknown Primary Site; Unusual Cancers of Childhood; Ureter and Renal Pelvis, Transitional Cell Cancer; Urethral Cancer; Uterine Sarcoma (including among others malignant mixed mullerian); Vaginal Cancer; Vulvar Cancer and Wilms' Tumor.

A drug eluting stent comprising a vascular stent containing a compound this invention, dispersed in, on or under a matrix, or disposed on surfaces or in channels, reservoirs or other chambers on or in said stent. Various types of stents and means and materials for loading such stents with drug are noted elsewhere herein and in references cited herein. Various matrices, polymers and other materials are also noted herein or in the cited references. Illustrative stents include the following stents: Angiomed (Bard), Cardiocoil (In-Stent Medtronic), CORINTHIAN (BSC), Radius (Scimed), Wallstent (Schneider), Act-one (ACT), Angiostent (angioynamics), be-Stent (In-Stent Medtronic), BiodivYsio (Biocompatibles), Cordis, Cross-flex (Cordis), Crown (JJIS), Freedom (Global therapeutics), Gianturco-Roubin II (Cook), Jo-med, Jostent flex (Jomed), Microstent GFX (AVE), Multilink (Guidant-ACS), NIR (Medinol), NIR Royal (Medinol), NIRflex (Medinol), NIRSIDE flex (Medinol), Palmaz-Scatz (JJIS), STS (De Scheerder), Tensum (Biotronic), Wiktor-GX (Medtronic), Wiktor-I (Medtronic), X-Trode (Bard), Y-Flex (Devon), Tsunami (Terumo), Bx Velocity (J&J), SLK-View (Advanced Stent Technologies, Inc.) and the Duraflex (Avantec) stent. The stent may be any of the foregoing, or may be another example of any of the types of stents noted herein and in the cited references, and may contain other materials (e.g. polymers which may be degradable or erodable or not) as noted elsewhere.

Compositions containing a compound of the invention and a diluent suitable for applying the compound to a stent.

This invention provides a family of new rapalogs, many illustrative types and specific examples of which are disclosed herein. Those compounds, rapamycin analogs modified relative to rapamycin at position 43, may also be further derivatized relative to rapamycin, e.g. at one or more of C7, C28, C13, C24 and C30 and elsewhere, by adapting chemical transformations such as those disclosed in U.S. Pat. No. 6,258,823, WO 96/41865, WO 98/02441, WO 99/36553 and WO 01/14387and in the other patent documents and scientific references cited therein or within this document. Compounds of interest include among others, those which bind to human FKBP12, or inhibit its rotamase activity, within two, and more preferably within one order of magnitude of results obtained with rapamycin in any conventional FKBP binding or rotamase assay.

Also included are pharmaceutically acceptable derivatives of the foregoing compounds, where the phrase "pharmaceutically acceptable derivative" denotes any pharmaceutically acceptable salt, ester, carbamate, or salt of such ester or carbamate of such compound, or any other adduct or derivative which, upon administration to a patient, is capable of providing (directly or indirectly) a JQA-containing rapalog as described herein, or a biologically active metabolite or residue thereof. Pharmaceutically acceptable derivatives thus include among others pro-drugs of the rapalogs. A pro-drug is a derivative of a compound, usually with significantly reduced pharmacological activity, which contains an additional moiety which is susceptible to removal in vivo yielding the parent molecule as the pharmacologically active species. An example of a pro-drug is an ester which is cleaved in vivo to yield a compound of interest. Various materials and methods for derivatizing rapamycin and of other compounds to create the pro-drugs are known and may be adapted to create produgs of compounds disclosed herein.

Compounds of this invention may be provided in substantially pure form (relative to side products, residual reactants or other unwanted materials), for example at least 50% pure, suitably at least 60% pure, advantageously at least 75% pure, preferably at least 85% pure, more preferably at least 95% pure, especially at least 98% pure, all percentages being calculated on a weight/weight basis. An impure or less pure form of a compound of the invention may be useful in the preparation of a more pure form of the same compound or of a related compound (for example a corresponding derivative) suitable for pharmaceutical use.

The compounds of this invention may be used for multimerizing chimeric proteins in cells (in vitro, ex vivo or in vivo, i.e. in organisms harboring them) for a variety of important purposes, as described in detail for rapamycin and other rapalogs in WO 96/41865, WO 99/36553 and WO 01/14387. See also Rivera V M, Ye X, Courage N L, Sachar J, Cerasoli F, Wilson J M and Gilman M. (1999) Long-term regulated expression of growth hormone in mice following intramuscular gene transfer. Proc Natl Acad Sci U S A 96, 8657–8662; and Ye X, Rivera V M, Zoltick P, Cerasoli F Jr, Schnell M A, Gao G-p, Hughes J V, Gilman M, and Wilson J M (1999) Regulated delivery of therapeutic proteins after in vivo somatic cell gene transfer. Science 283, 88–91. Materials and methods which may be adapted for these purposes are disclosed in WO 01/14387 (especially on pages 18 to 24), incorporated herein by reference. In adapting the disclosure of WO 01/14387, for example, one substitutes a rapalog of this invention for the 28-epi-rapalogs referred to there.

Compounds of this invention having antifungal activity, including among others those having a replacement C7 substituent in place of methoxyl, are useful (as a monotherapy or in combination with one or more other antifungal therapies) for the prophylaxis and treatment of fungal infections in animals, especially mammals, including humans, in particular humans and domesticated animals (including farm animals). The compounds may be used, for example, in the treatment of topical fungal infections caused by, among other organisms, species of *Candida* (e.g. *C. albicans*), *Trichophyton* (e.g. *Trichophyton mentagrophytes*), *Microsporum* (e.g. *Microsporum gypseum*) or *Epidermophyton* or in mucosal infections caused by *Candida albicans* (e.g. thrush and vaginal candidiasis). They may also be used in the treatment of systemic fungal infections caused by, for example *Candida albicans, Cryptococcus neoformans, Aspergillus fumigatus, Coccidiodes, Paracocciciodes, Histoplasma* or *Blastomyces* spp. They may also be of use in treating eumycotic mycetoma, chromoblastomycosis and phycomycosis. Other fungal infections for which compounds of this invention are applicable and considerable background information on assays for comparative evaluation of the compounds, formulation and administration of rapalogs for treating fungal infection can be found in Holt et al, U.S. Pat. No. 6,258,823 (issued Jul. 10, 2001) and references cited therein, the contents of which are incorporated herein by reference. Note that antifungal rapalogs of this invention may retain the methoxyl substituent at C7 or may contain any of a variety of replacement substituents, including H and bulky or non-bulky substituents. U.S. Pat. No. 6,258,823, for instance, discloses a series of C7 replacement substituents which may be incorporated into the design of compounds of FIG. 1, especially for antifungal or multimerizing applications.

Certain compounds of this invention have been found to inhibit T cell proliferation with observed EC50 values ranging to potency levels comparable to rapamycin. Potent activity has also been observed against human tumors in a nude mouse xenograft model. These rapalogs typically retain the methoxyl substituent at C7 or replace it with H or a replacement substituent which is not so much bulkier than methoxyl that it unduly reduces inhibition of T cell proliferation. These rapalogs may be used as immunosuppressant, antiproliferative, anti-tumor, and anti-restenotic agents, as well as for other uses described herein or in the literature for rapamycin and analogs such as CCI 779 and SDZ RAD ("RAD 001") in the scientific and patent literature, examples of which are cited herein. Compounds with a —OMe group at C7, or which contain a replacement C7 substituent (i.e., in place of —OMe) that does not unduly reduce potency in a T cell inhibition assay, are of particular interest for such uses.

More specifically, certain compounds of this invention have immunomodulatory activity, meaning that the compounds are capable of inducing immune suppression by inhibiting immune cell responses or proliferation in vitro or in vivo and/or by producing a statistically significant decrease in the inflammatory response as determined by any scientifically acceptable cellular, tissue or animal model. Such compounds may be administered in a treatment effective amount and dosing regimen for treating, among others, conditions such as rheumatoid arthritis, osteoarthritis, systemic lupus erythematosis, multiple sclerosis, acute transplantation/graft rejection, myasthenia gravis, progressive systemic sclerosis, tuberous sclerosis, multiple myeloma, atopic dermatitis, hyperimmunoglobulin E, hepatitis B antigen negative chronic active hepatitis, Hashimoto's thyroiditis, Familial Mediterranean fever, Grave's disease, autoimmune hemolytic anemia, primary biliary cirrhosis, inflammatory bowel disease, and insulin dependent diabetes mellitus.

Compounds of this invention also have activity against primary and/or metastatic cancers, including cancers which are or have become resistant to treatment with other agents. Our compounds should be useful for reducing tumor size, inhibiting tumor growth or metastasis; treating various leukemias and/or prolonging the survival time of animals or patients with those diseases.

Accordingly the invention provides compounds for use in medical therapy, in particular for use as antifungal, anticancer, immunosuppressive or anti-restenotic agents, or as agents against the other diseases and conditions disclosed herein.

The invention further provides a method of treating a human or non-human animal suffering from any of those diseases or conditions by the administration of an effective amount of the rapalog, and further provides pharmaceutical compositions comprising a compound of the invention together with a pharmaceutically acceptable diluent or carrier, as well as medical devices, such as drug-bearing stents, containing a compound of this invention.

Compounds of this invention may be formulated as disclosed below and elsewhere herein (or using formulations based on those reported for rapamycin or rapamycin derivatives such as CCI-779 or RAD001), and may then be administered in treatment effective amounts to patients in need thereof for the treatment of a variety of diseases as noted herein. Such compositions may be administered in any manner useful in directing the active compounds to the recipient's bloodstream or site of action, including orally, parenterally (including intravenous, intraperitoneal and subcutaneous injections as well as injection into joints or other tissues), via stents or other implants, rectally, intranasally, vaginally, and transdermally. For the purposes of this disclosure, transdermal administrations are understood to include all administrations across the surface of the body and the inner linings of bodily passages including epithelial and mucosal tissues. Such administration may be carried out using the present compounds, or pharmaceutically acceptable salts or prodrugs thereof, in lotions, creams, foams, patches, suspensions, solutions, and suppositories (rectal and vaginal).

For parenteral or intraperitoneal administration, solutions or suspensions of these active compounds or a pharmacologically acceptable salt thereof can be prepared in water suitably mixed with a surfactant such as hydroxy-propylcellulose or by adaptation of formulations used for rapamycin, CCI779 or RAD001. Dispersions can also be prepared in glycerol, liquid polyethylene glycols and mixtures thereof in oils. Under ordinary conditions of storage and use, these preparations may contain a preservative to prevent the growth of microorganisms.

Compositions which contain a compound of this invention and which are suitable for injectable use include sterile aqueous solutions or dispersions and sterile powders for the extemporaneous preparation of sterile injectable solutions or dispersions. In all cases, the composition to be injected should be sterile and should be sufficiently fluid to permit transfer via syringe. It should be stable under the conditions of manufacture and storage and will preferably be protected from the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils. Parenteral formulations which may be adapted for use with rapalogs of this invention are disclosed in U.S. Pat. Nos. 5,530,006; 5,516,770; and 5,616,588, which are hereby incorporated by reference.

Formulation, routes of administration and dosing may be selected from, or based upon, those used for rapamycin and other rapamycin derivatives used for the same or analogous indications. In the case of treating tumors, it may be preferred to first determine whether the function of PTEN (or PTEN-mediated processes) is partially or wholly deficient in a patient's tumor, and then to selectively treat the patients with PTEN-deficient tumors (See e.g., Neshat et al, PNAS, above). More generally, a preferred approach may be to determine through genotype analysis and/or in vitro culture and study of biopsied tumor samples, those patients with tumors in which the phosphatidyl-inositol 3 kinase/Akt-mTOR signaling pathway or the mTOR-mediated nutrient sensing pathway is particular important to cell growth, and then to selectively treat those patients with rapalog. Non-limiting examples of such cancers involving abnormalities in the phosphatidyl-inositol 3 kinase/Akt-mTOR pathway include glioma, lymphoma and tumors of the lung, bladder, ovary, endometrium, prostate or cervix which are associated with abnormal growth factor receptors (e.g. EGFR, PDGFR, IGF-R and IL-2); ovarian tumors which are associated with abnormalities in PI3 kinase; melanoma and tumors of the breast, prostate or endometrium which are associated with abnormalities in PTEN; breast, gastric, ovarian, pancreatic, and prostate cancers associated with abnormalities with Akt; lymphoma, cancers of the breast or bladder and head and neck carcinoma associated with abnormalities in elF-4E; mantle cell lymphoma; breast cancer and head and neck carcinomas associated with abnormalities in Cyclin D; and, familial melanoma and pancreas carcinomas associated with abnormalities in P16.

For all of the indications noted herein, it may be beneficial in some cases to treat the patient with a combination of a compound of this invention and one or more other agents useful for treating the relevant disease. The combination may be administered together or separately (e.g., serially). For instance, a patient being treated with an anti-cancer compound of this invention, may (before, during or after such treatment) also be treated one or more other anti-cancer agents such as cisplatin; an antiestrogen (e.g., raloxifene, droloxifene, idoxifine, nafoxidine, toremifene, TAT-59, levomeloxifene, LY-353381, CP-3361656, MDL-103323, EM-800 and ICI-182,780; see e.g. WO 02/13802 which may be adapted to the present invention); an inhibitor of one or more kinases such as Src, BRC/Abl, kdr, aurora-2, glycogen synthase kinase 3 ("GSK-3"), an epidermal growth factor receptor ("EGF-R"), or platelet derived growth factor receptor ("PDGF-R") for example, including inhibitors such as Gleevec, Iressa, CP-358774 (Tarceva), ZD-1839, SU-5416, or NSC-649890; an antibody (such as Herceptin) to a receptor or hormone (e.g. VEGF) implicated in a cancer, or a soluble receptor or other receptor antagonist to such receptor; a proteasome inhibitor such as Velcade; an IKK inhibitor or other NF-kB inhibitor; or radiation. Each component of the combination may be administered as it would be if given alone, although in some cases reduced dosing of one or more components may be possible or beneficial in view of the combined action of the different drugs.

Compounds of this invention can also be used to help prevent restenosis or other complications by systemic administration of the drug or introduction into the patient's body of a graft, stent, or other device bearing the drug. See e.g. Sousa et al, above, and Marx and Marks, 2001, Circulation 104:852–855. Thus, the rapalogs of this invention may be administered systemically or applied to stents, grafts, shunts or other devices or scaffolds (including cardiac pacemaker leads or lead tips, cardiac defibrillator leads or lead tips, heart valves, pacemakers, orthopedic devices, etc.) to provide drug-eluting devices for implantation into patients in need thereof. Stents and such devices are typically inserted into a patient's vasculature (e.g. veins, arteries, aorta, etc., including both coronary and peripheral arteries) but can also be used in many other organs, glands, ducts, etc.

A stent is an expandable tube, typically an expandable wire mesh tube, small enough to be inserted into a blood vessel. They are typically used to prevent closure of the vessel after a procedure such as angioplasty. A growing variety of stent designs and types are available for the practitioner, including stents made from nitinol (a nickel-titanium alloy), cobalt alloy on a platinum core, platinum-iridium, stainless steel, gold plated stainless steel, silicon carbide, tantalum, coated tantalum, and other metals or non-metals, in a variety of designs including wire braid, spiral coil, slotted tube (zig zag design, serpentine mesh with rotating junctions, sinusoidal slot, cellular mesh, spiral articulation, etc.), wire mesh, sinusoidal single wire coil, single helical coil, fishbone, flexible coil, connected zig-zag wires, multiple rings, multicellular, etc.

An all too frequent complication of the use of stents is re-closure ("restenosis") of the vessel after insertion of the stent. One of the primary causes of restenosis is thought to be rapid proliferation of blood vessel cells in the region of the stent ("neointimal hyperplasia"), eventually blocking the vessel. One approach for reducing the incidence of restenosis has been the use of drug-eluting stents using Paclitaxel, rapamycin, Everolimus (RAD001) or other drugs. Other benefits of drug-eluting stents have also been noted in the literature.

To provide a stent (or other implantable device) with reduced likelihood of restenosis, a compound of this invention may be disposed on or in such a device in place of rapamycin or other drug such that the compound is released ("elutes") from the device after it is implanted in the recipient. Drug eluting stents are generally prepared by coating at least part of the stent with a carrier material (typically a polymer) containing the drug or by filling one or more surfaces or chambers or channels in, or on the surface of, the stent with the drug or a composition containing the drug. Coatings may be applied in more than one layer, some of which might not contain the drug. Sometimes an additional coating is provided on top of the drug-containing layer or reservoir, which additional coating permits gradual release of drug to the recipient's tissues.

A variety of methods and materials for applying drugs to stents and for using such stents are available to the practitioner and may be adapted to use with compounds of this invention. For instance, methods and materials for releasing drugs from implantable and other devices are described in U.S. Pat. Nos. 6,471,980; 6,096,070; 5,824,049; 5,624,411; 5,609,629; 5,569,463; 5,447,724; and 5,464,650 as well as WO02066092. The use of stents for drug delivery within the vasculature are described in PCT Publication No. WO 01/01957 and U.S. Pat. Nos. 6,099,561; 6,071,305; 6,063, 101; 5,997,468; 5,980,551; 5,980,566; 5,972,027; 5,968, 092; 5,951,586; 5,893,840; 5,891,108; 5,851,231; 5,843, 172; 5,837,008; 5,769,883; 5,735,811; 5,700,286; 5,679, 400; 5,649,977; 5,637,113; 5,591,227; 5,551,954; 5,545, 208; 5,500,013; 5,464,450; 5,419,760; 5,411,550; 5,342, 348; 5,286,254; and 5,163,952. Biodegradable materials are described in U.S. Pat. Nos. 6,051,276; 5,879,808; 5,876, 452; 5,656,297; 5,543,158; 5,484,584; 5,176,907; 4,894, 231; 4,897,268; 4,883,666; 4,832,686; and 3,976,071. The use of hydrocyclosiloxane as a rate limiting barrier is described in U.S. Pat. No. 5,463,010. Methods for coating of stents is described in U.S. Pat. No. 5,356,433. Coatings to enhance biocompatibility of implantable devices are described in U.S. Pat. Nos. 5,463,010; 5,112,457; and 5,067, 491. Energy based devices are described in U.S. Pat. Nos. 6,031,375; 5,928,145; 5,735,811; 5,728,062; 5,725,494; 5,409,000; 5,368,557; 5,000,185; and 4,936,281. Magnetic processes, some of which have been used in drug delivery systems, are described in U.S. Pat. Nos. 5,427,767; 5,225, 282; 5,206,159; 5,069,216; 4,904,479; 4,871,716; 4,501, 726; 4,3579259; 4,345,588; and 4,335,094. Expandable medical devices containing one or more drugs in one or more openings on or in the device, using various optional layers, barrier compositions, and configurations are disclosed in Shanley et al, U.S. patent application Pub. No. 2002/0082680. See also e.g., U.S. Pat. No. 6,471,979 which discloses methods and materials for loading a stent which may be applied to compounds of this invention. Exemplary coatings disclosed therein include phosphorylcholine, polyurethane, segmented polyurethane, poly-L-lactic acid, cellulose ester, polyethylene glycol and polyphosphate esters, as well as naturally occurring vehicles or carriers like collagens, laminens, heparins, fibrins, and other naturally occurring substances that absorb to cellulose. Using such a coating is advantageous in that it allows the compound to slowly release from the device. This extends the time that the affected portion of the body sustains the efficacious effects of the compounds. The manner in which these coatings interact with the device material as well as the inherent structure of the coating provide a diffusion barrier, thereby controlling the release of the entrapped compound(s). Thus, the matrix or coating with which the compounds are loaded on the stent or delivery device can control slow or fast delivery of the compound.

In other approaches, a coating such as a Phosphorylcholine-based coating like Biocompatibles' (LO) PC polymer is used. Such coatings contain a hydrophobic component which aids in the initial adhesion and film-formation of the polymer on to the stainless steel stent substrate, while other groups allow cross-linking both within the polymer and with the stent surface to achieve firm anchorage. The coating is thus tightly adhered to the stent and can survive balloon expansion without damage. The coating can absorb a variety of molecules of different size and physical characteristics into the PC coating, and to release those in a controlled manner. The PC coating may be as thin as ~0.1 µm, although thicker layers may also be used. The stent, coated with the LO matrix may be immersed in a solution of the compound in an organic solvent for as little as a few minutes. The loading level can be controlled by the concentration of the solution of the compound. After removal from the solution, the coating is allowed to dry briefly before it is ready for use. See e.g., WO 01/00109, 01/01957, 01/52915, 02/55121 and 02/55122.

The use of a rapalog of this invention in conjunction with a stent may be achieved, e.g., by adapting methods and materials used for the delivery of other drugs (including among others rapamycin and paclitaxel) using such devices, e.g. as disclosed in the foregoing documents as well as in U.S. Pat. Nos. 5,516,781; 6,153,252; 5,665,728; 5,646,160; 5,563,146; and 5,516,781 as well as in published international patent applications WO 01/01957, 01/49338, 01/87263, 01/87342, 01/87372, 01/87373, 01/87374, 01/87375, and 01/87376. Rapalogs of this invention are broadly compatible across the range of stent designs and of methods and materials for coating, depositing, layering or otherwise loading them with drug. Loading such medical devices with a rapalog of this invention, medical devices loaded with a rapalog of this invention and the insertion into a blood vessel or other lumen in a recipient of such a device loaded with such a rapalog are all encompassed by this invention, including the various matrices, polymers, barriers, and other options available to the practitioner. In practice, the choice of materials (e.g. solvents, polymers, barrier layers, matrices, etc.) and precise methods may be optimized, depending on the choice of compound, using routine experimentation. In other words, desirable and optimal choices of stent design or composition, solvents, cosolvents, polymers, copolymers, coatings, barriers, drug-loading procedures, ranges of concentration or time or temperature, etc. will become clear in a given case using routine practices.

Further discussion of pharmaceutical uses, formulation, dosing, and administration is provided below.

DETAILED DESCRIPTION OF THE INVENTION

In reading this document, the following information and definitions apply unless otherwise indicated. In addition, unless otherwise indicated, all occurrences of a functional group are independently chosen, as the reader is in some cases reminded by the use of a slash mark or prime to indicate simply that the two occurrences may be the same or different (e.g., R and R'). Numbering of atoms in or relating to chemical structures disclosed in this document is with reference to the numbering system shown in Formula I. Also, the reader is directed to pages 15–18 of WO 01/14387 for additional definitions and orienting information which supplement the following.

The term "aliphatic" as used herein includes both saturated and unsaturated (but non-aromatic), straight chain (i.e., unbranched), branched, cyclic, or polycyclic non-aromatic hydrocarbon moieties, which are optionally substituted with one or more functional groups. Unless otherwise specified, alkyl, other aliphatic, alkoxy and acyl groups preferably contain 1–8, and in many cases 1–6, contiguous aliphatic carbon atoms. Illustrative aliphatic groups thus include, for example, methyl, ethyl, n-propyl, isopropyl, cyclopropyl, —$CH_2$-cyclopropyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl moieties and the like, which again, may bear one or more substituents.

The term "aliphatic" is thus intended to include alkyl, alkenyl, alkynyl, cycloalkyl, cycloalkenyl, and cycloalkynyl moieties.

As used herein, the term "alkyl" includes both straight, branched and cyclic alkyl groups. An analogous convention applies to other generic terms such as "alkenyl", "alkynyl" and the like. Furthermore, as used herein, the language "alkyl", "alkenyl", "alkynyl" and the like encompasses both substituted and unsubstituted groups.

The term "alkyl" refers to groups usually having one to eight, preferably one to six carbon atoms. For example, "alkyl" may refer to methyl, ethyl, n-propyl, isopropyl, cyclopropyl, butyl, isobutyl, sec-butyl, tert-butyl, cyclobutyl, pentyl, isopentyl tert-pentyl, cyclopentyl, hexyl, isohexyl, cyclohexyl, and the like. Suitable substituted alkyl groups include, but are not limited to, fluoromethyl, difluoromethyl, trifluoromethyl, 2-fluoroethyl, 3-fluoropropyl, hydroxymethyl, 2-hydroxyethyl, 3-hydroxypropyl, benzyl, substituted benzyl and the like.

The term "alkenyl" refers to groups usually having two to eight, preferably two to six carbon atoms. For example, "alkenyl" may refer to prop-2-enyl, but-2-enyl, but-3-enyl, 2-methylprop-2-enyl, hex-2-enyl, hex-5-enyl, 2,3-dimethyl-but-2-enyl, and the like. The language "alkynyl," which also refers to groups having two to eight, preferably two to six carbons, includes, but is not limited to, prop-2-ynyl, but-2-ynyl, but-3-ynyl, pent-2-ynyl, 3-methylpent-4-ynyl, hex-2-ynyl, hex-5-ynyl, and the like.

The term "cycloalkyl" as used herein refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of other aliphatic or heteroaliphatic or heterocyclic moieties, may optionally be substituted.

The term "heteroaliphatic" as used herein refers to aliphatic moieties which contain one or more oxygen, sulfur, nitrogen, phosphorous or silicon atoms, e.g., in place of carbon atoms. Heteroaliphatic moieties may be branched, unbranched or cyclic and include heterocycles such as morpholino, pyrrolidinyl, etc.

The term "heterocycle", "heterocyclyl", or "heterocyclic" as used herein refers to non-aromatic ring systems having five to fourteen members, preferably five to ten, in which one or more ring carbons, preferably one to four, are each replaced by a heteroatom such as N, O, or S. Non-limiting examples of heterocyclic rings include 3-1H-benzimidazol-2-one, (1-substituted)-2-oxo-benzimidazol-3-yl, 2-tetrahydrofuranyl, 3-tetrahydrofuranyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperdinyl, 4-thiazolidinyl, diazolonyl, N-substituted diazolonyl, 1-phthalimidinyl, benzoxanyl, benzopyrrolidinyl, benzopiperidinyl, benzoxolanyl, benzothiolanyl, and benzothianyl. Also included within the scope of the term "heterocyclyl" or "heterocyclic", as it is used herein, is a group in which a non-aromatic heteroatom-containing ring is fused to one or more aromatic or non-aromatic rings, such as in an indolinyl, chromanyl, phenanthridinyl, or tetrahydroquinolinyl, where the radical or point of attachment is on the non-aromatic heteroatom-containing ring. The term "heterocycle", "heterocyclyl", or "heterocyclic" whether saturated or partially unsaturated, also refers to rings that are optionally substituted.

The term "aryl" used alone or as part of a larger moiety as in "aralkyl", "aralkoxy", or "aryloxyalkyl", refers to aromatic ring groups having five to fourteen members, such as phenyl, 1-naphthyl, 2-naphthyl, 1-anthracyl and 2-anthracyl. The term "aryl" also refers to rings that are optionally substituted. The term "aryl" may be used interchangeably with the term "aryl ring". "Aryl" also includes fused polycyclic aromatic ring systems in which an aromatic ring is fused to one or more rings. Non-limiting examples of useful aryl ring groups include phenyl, halophenyl, alkoxyphenyl, dialkoxyphenyl, trialkoxyphenyl, alkylenedioxyphenyl, naphthyl, phenanthryl, anthryl, phenanthro and the like, as well as 1-naphthyl, 2-naphthyl, 1-anthracyl and 2-anthracyl. Also included within the scope of the term "aryl", as it is used herein, is a group in which an aromatic ring is fused to one or more non-aromatic rings, such as in a indanyl, phenanthridinyl, or tetrahydronaphthyl, where the radical or point of attachment is on the aromatic ring.

The term "heteroaryl" as used herein refers to stable heterocyclic, and polyheterocyclic aromatic moieties having 3–14, usually 5–14, carbon atoms, which moieties may be substituted or unsubstituted and may comprise one or more rings. Substituents include any of the previously mentioned substituents. Examples of typical heteroaryl rings include 5-membered monocyclic ring groups such as thienyl, pyrrolyl, imidazolyl, pyrazolyl, furyl, isothiazolyl, furazanyl, isoxazolyl, thiazolyl and the like; 6-membered monocyclic groups such as pyridyl, pyrazinyl, pyrimidinyl, pyridazinyl, triazinyl and the like; and polycyclic heterocyclic ring groups such as benzo[b]thienyl, naphtho[2,3-b]thienyl, thianthrenyl, isobenzofuranyl, chromenyl, xanthenyl, phenoxathienyl, indolizinyl, isoindolyl, indolyl, indazolyl, purinyl, isoquinolyl, quinolyl, phthalazinyl, naphthyridinyl, quinoxalinyl, quinazolinyl, benzothiazole, benzimidazole, tetrahydroquinoline cinnolinyl, pteridinyl, carbazolyl, beta-carbolinyl, phenanthridinyl, acridinyl, perimidinyl, phenanthrolinyl, phenazinyl, isothiazolyl, phenothiazinyl, phenoxazinyl, and the like (see e.g. Katritzky, Handbook of Heterocyclic Chemistry). Further specific examples of heteroaryl rings include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazoyl, 5-oxazolyl, 1-pyrrolyl, 2-pyrrolyl, 3-pyrrolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indolyl, isoindolyl, acridinyl, or benzoisoxazolyl. Heteroaryl groups further include a group in which a heteroaromatic ring is fused to one or more aromatic or nonaromatic rings where the radical or point of attachment is on the heteroaromatic ring. Examples include tetrahydroquinoline, tetrahydroisoquinoline, and pyrido[3,4-d]pyrimidinyl. The term "heteroaryl" also refers to rings that are optionally substituted. The term "heteroaryl" may be used interchangeably with the term "heteroaryl ring" or the term "heteroaromatic".

An aryl group (including the aryl portion of an aralkyl, aralkoxy, or aryloxyalkyl moiety and the like) or heteroaryl group (including the heteroaryl portion of a heteroaralkyl or heteroarylalkoxy moiety and the like) may contain one or more substituents. Examples of suitable substituents on the unsaturated carbon atom of an aryl or heteroaryl group include halogen, —$YR^2$ (i.e., including —$R^2$, —$OR^2$, —$SR^2$ and —$NR^2R^5$), —Y—C(=O)$R^2$, —Y—C(=O)$OR^2$, —Y—C(=O)$NR^2R^5$, —Y—C(=$NR^{2'}$)$NR^2R^5$, —COCOR$^2$, —COMCOR$^2$), J, —CN, —S(=O)$R^2$, —$SO_2R^2$, —$SO_2NR^2R^5$, —$NO_2$, —$NR^5SO_2R^2$ and —$NR^5SO_2NR^2R^5$. To illustrate further, substituents in which Y is $NR^2$ thus include among others, —$NR^2$C(=O)$R^5$, —$NR^2$C(=O)$NR^5$, —$NR^2$C(=O)$OR^5$, and —$NR^2$C(=NH)$NR^5$. Note that $R^2$ and $R^5$ substituents may themselves be substituted or unsubstituted (e.g. non-limiting illustrations of an $R^5$ moiety include -alkylhalo such as chloromethyl or trichloromethyl; -alkoxyalkyl such as methoxyethyl-; mono-, di- and tri-alkoxyphenyl; methylenedioxyphenyl or ethylenedioxyphenyl; halophenyl; and alkylamino). Additional illustrative examples include 1,2-methylene-dioxy, 1,2-ethylenedioxy, protected OH (such as acyloxy)), phenyl, substituted phenyl, —O-phenyl, —O-(substituted) phenyl, -benzyl, substituted benzyl, —O-phenethyl (i.e., —$OCH_2CH_2C_6H_5$), —O-(substituted)phenethyl, —C(O)$CH_2$C(O)$R^2$, —$CO_2R^2$, —C(=O)$R^2$ (i.e., acyl in cases in which $R^2$ is aliphatic, aroyl in cases in which $R^2$ is aryl and heteroaroyl in cases in which $R^2$ is heteroaryl), —C(=O)$NR^2R^5$, —OC(=O)$NR^2R^5$, —C(=NH)$NR^2R^5$, and —OC(=NH)$NR^2R^5$. Further examples of substituents include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, and haloalkyl groups.

An aliphatic, heteroaliphatic or non-aromatic heterocyclic group may also contain one or more substituents. Examples of suitable substituents on such groups include those listed above for the carbon atoms of an aryl or heteroaryl group and in addition include the following substituents for a saturated carbon atom: =O, =S, =$NR^2$, =$NNR^2R^5$, =NNHC(O)$R^2$, =$NNHCO_2R^2$, or =$NNHSO_2R^2$. Illustrative examples of substituents on an aliphatic, heteroaliphatic or heterocyclic group include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl groups.

Illustrative substituents on the nitrogen of an aromatic or non-aromatic heterocyclic ring include —$R^2$, —$NR^2R^5$, —C(=O)$R^2$, —C(=O)$OR^2$, —C(=O)$NR^2R^5$, —C(=$NR^{2'}$)$NR^2R^5$, —COCOR$^2$, —COMCOR$^2$), —CN, —$NR^5SO_2R^2$ and —$NR^5SO_2NR^2R^5$.

Examples of substituents on the aliphatic group or the phenyl ring include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

A combination of substituents or variables is permissible only if such a combination results in a stable or chemically feasible compound. A stable compound or chemically feasible compound is one that is not substantially altered when kept at a temperature of 40° C. or less, in the absence of moisture or other chemically reactive conditions, for at least a week.

Certain compounds of this invention may exist in tautomeric forms, and this invention includes all such tautomeric forms of those compounds unless otherwise specified.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Thus, this invention encompasses each diasteriomer or enantiomer substantially free of other isomers (>90%, and preferably >95%, free from other stereoisomers on a molar basis) as well as a mixture of such isomers. (In chemical structures in this document, a wavy line, e.g. the wavy line in Formula I at positions 43 and 28, indicates either R or S orientation.)

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a 13 C- or 14 C-enriched carbon are within the scope of this invention.

A JQA-containing rapalog as described herein (i.e., 43-JQA-containing rapalogs) may differ from the corresponding 43-JQA-containing derivative of rapamycin with respect to zero, one, two, three, four, five, six or seven (or more) substituent moieties or functional groups at positions other than position 43. One class of rapalogs of this invention includes JQA-containing rapalogs with no other modifications, relative to rapamycin, i.e., other than the JQA modification at position 43. Another class includes among others JQA-containing rapalogs with additional modification(s) at any one, two, three, four, five or all six of positions C7, C13, C14, C24, C28 and C30. Modifications in rapalog structure are known for a number of previously known rapalogs (see e.g. WO 99/36553, Table III and Liberles et al, 1997, *Proc Natl Acad Sci USA* 94:7825–7830 and infra) and may be readily adapted to the present invention. See also WO 01/14387, already incorporated herein by reference, including among others pages 24–30, for information on known modifications and combinations of modifications known for rapamycin which may be used in the design of JQA-containing rapalogs.

One subset of JQA-containing rapalogs of special interest for practicing the methods of this invention are those those (or pharmaceutically acceptable derivatives thereof) in which $R^{C7a}$ is a moiety other than OMe. This subset ("C7 JQA-containing rapalogs") includes compounds in which one of $R^{7a}$ and $R^{7b}$ is H and the other is selected from —$R^A$, —Z—$R^A$, —Z—(CO)$R^A$, —Z—(CO)Z$R^A$, —N$R^A$SO$_2$$R^A$ and —NSO$_2$$R^A$, where each Z is independently O, S or N$R^A$. Illustrating this subset are the JQA-containing rapalogs bearing a C7 substituent selected from the following group: aryl; heteroaryl; aryl, heteroaryl or benzyl ether; and —NH(CO)O$R^A$, —NH(CO)$R^A$, —NH(SO$_2$)$R^A$ or —NH(SO$^2$)NH$R^A$ (where $R^A$ is a substituted or unsubstituted lower alkyl, e.g., methyl, ethyl, iPr, butyl, benzyl, etc. or is a substituted or unsubstituted phenyl (e.g., p-tolyl); In certain embodiments of this subset, $R^{7a}$ and $R^{7b}$ are independently selected from the following groups: H; a substituted or unsubstituted two to eight carbon straightchain, branched or cyclic alkenyl, alkoxyl or alkylmercapto; and a substituted or unsubstituted aryl , heteroaryl, aryloxy or heteroaryloxy, arylmercapto or heteroarylmercapto. Compounds of this subset include among others those in which $R^{7a}$ is H; (together with $R^{7b}$) =O; alkoxy; alkylmercapto; amino (primary, secondary, tertiary or quaternary); amido; carbamate; aryl or substituted aryl; phenyl or substituted phenyl; substituted or unsubstituted heteroaryl such as substituted or unsubstituted thiophenyl, furyl, indolyl, etc.; or benzyloxy or substituted benzyloxy. Other illustrative C7 JQA-containing rapalogs which may be used in practicing the methods of this invention include those in which one of $R^{7a}$ and $R^{7b}$ is H and the other is selected from —OEt, —O-propyl, —O-butyl, —OCH$_2$CH$_2$—OH, —O-benzyl, —O-substituted benzyl (including e.g., 3-nitro-, 4-chloro-, 3-iodo4-diazo-, 3,4-dimethoxy-, and 2-methoxy-), —S—Me, —S-phenyl, —O(CO)Me, -allyl, —CH$_2$C(Me)=CH$_2$, —OCH$_2$—CCH, —OCH$_2$—CC—Me, —OCH$_2$—CC—Et, —OCH$_2$—CC—CH$_2$OH, or -2,4-dimethoxyphenyl, 2,4,6-trimethoxyphenyl, furanyl, thiophen-yl, methylthiophen-yl, pyrolyl and indolyl. C7-modified JQA-containing rapalogs of particular interest are those bearing a substituted or unsubstituted aromatic ether, a substituted or unsubstituted benzyl ether or a carbamate moiety at C7. In C7-modified embodiments, the substituent at C43 may be present in either stereochemical orientation (or as a mixture of isomers). C7 JQA-containing rapalogs may further vary from the corresponding C7-modified rapamycin at one, two, three, four, five or more other positions as well.

43 JQA-rapamycin and C7 JQA-containing rapalogs of are of particular interest.

Another subset of JQA-containing rapalogs of special interest in the practice of the various methods of the invention are those in which the substituents at C24 and C30 are both other than (=O). Of special interest are those C30 and C24 substituents disclosed in WO 99/36553. This subset includes among others all 43-JQA-containing rapalogs in which $R^{C30}$ and $R^{C24}$ are OH and one of $R^{C7a}$ and $R^{C7b}$ comprises any of the replacement substituents at that position specified herein, including any of the C7 substituents identified in WO 01/14387. Of special interest are compounds in which one of $R^{C7a}$ and $R^{C7b}$ is cyclic aliphatic, aryl, heterocyclic or heteroaryl, which may be optionally substituted. Other compounds within this subset include those in which one, two, three, four or five of the hydroxyl groups is epimerized, fluorinated, alkylated, acylated or otherwise modified via other ester, carbamate, carbonate or urea formation. An illustrative compound for example is the JQA-containing rapalog in which the hydroxyl groups at C28 and C30 are alkylated, acylated or linked via carbonate formation.

Another subset of JQA-containing rapalogs of special interest are the mono- and difluoro-JQA-containing rapalogs which contain an F at one or both of C13 and C28, as disclosed in WO 99/36553, with or without additional changes elsewhere in the JQA-containing rapalog molecule.

Another subset of JQA-containing rapalogs of interest have an $R^{C24}$ which is other than =O, again, with or without one or more other modifications at other positions relative to rapamycin.

Other JQA-containing rapalogs of interest include those in which $R^{C14}$ is OH.

Furthermore, this invention encompasses JQA-containing rapalogs in which one or more of the carbon-carbon double bonds at the 1,2, 3,4 or 5,6 positions in rapamycin are saturated, alone or in combination with a modification elsewhere in the molecule, e.g. at one or more of C7, C13, C24 C28 and/or C30. It should also be appreciated that the C3,C4 double bond may be epoxidized; that the C6 methyl group may be replaced with —CH$_2$OH or —CH$_2$OMe; that the C42 methoxy moiety may be demethylated, in any of the compounds disclosed herein, using methods known in the art.

Synthetic Guidance

The production of rapamycin by fermentation and by total synthesis is known. The production of a number of rapalogs as fermentation products is also known. These include among others rapalogs bearing alternative moieties in place of the characteristic cyclohexyl ring or pipecolate ring of rapamycin, as well as C7-desmethyl-rapamycin, C29-desmethyl-rapamycin and C29-desmethoxyrapamycin, among others.

Methods and materials for effecting various chemical transformations of rapamycin and structurally related macrolides are known in the art. Many such chemical transformations of rapamycin and various rapalogs are disclosed in the patent documents identified in Table I of WO/014387 which serve to help illustrate the level of skill and knowledge in the art of chemical synthesis and product recovery, purification and formulation which may be applied in practicing the subject invention. Several representative transformations and/or references which can be employed to produce the desired rapalogs are noted for the sake of illustration:

| Ring position modified | Literature reference |
|---|---|
| C7 | Luengo et al, J Org Chem 59, 6512 (1995); Chem & Biol 2 (7), 471–481 (1995) |
| C14 | Schubert et al, Angew Chemie Int Ed Engl 23, 167 (1984) |
| C20 | Nelson, U.S. Pat. No. 5,387,680 |
| C-24 | U.S. Pat. Nos. 5,373,014 and 5,378,836; Lane et al, Synthesis 1975, p./136 |
| C-30 | Luengo et al, Tet Lett 35, 6469 (1994) |

See also: U.S. Pat. Nos. 5,100,883; 5,118,677; 5,118,678; 5,130,307; 5,177,203; and 5,194,447 for materials and methods concerning the preparation of fluorinated esters, amide esters, carbamates, aminoesters, sulfonates and sulfamates, and sulfonylcarbamates of rapamycin.

Additionally, the conversion of rapamycin to 28-epirapamycin can be readily carried out as described e.g. in WO/014387. That document also identifies materials and methods for effecting many other known chemical transformations of rapamycin. See also references cited therein and US 2001/0010920. 28-epi rapamycin may be used in place of rapamycin in the practice of the present invention to afford the corresponding 28-epi rapalog modified at position 43 in accordance with the present disclosure.

Similarly, the reduction of ketones at one or both of positions 24 and 30 may be effected using known methods, e.g. methods previously used with rapamycin itself, but now applied to the C-43 rapalogs disclosed herein to afford the corresponding 24-hydroxyl-, 30-hydroxyl- or 24, 30-tetrahydro-rapalogs modified at position 43 in accordance with the present disclosure.

It is also contemplated that rapalogs for use as intermediates in the production of 43-JQA-rapalogs may be prepared by directed biosynthesis, e.g. as described by Katz et al, WO 93/13663 and by Cane et al, WO 9702358. See also Khaw et al, 1998, J. Bacteriology 180 (4):809–814 for additional biological methods.

Rapalogs of this invention may be prepared by one of ordinary skill in this art relying upon methods and materials known in the art as guided by the disclosure presented herein. For instance, methods and materials may be adapted from known methods set forth or referenced in the documents cited above, the full contents of which are incorporated herein by reference. Additional guidance and examples are provided herein by way of illustration and further guidance to the practitioner. It should be understood that the chemist of ordinary skill in this art would be readily able to make modifications to the foregoing, e.g. to add appropriate protecting groups to sensitive moieties during synthesis, followed by removal of the protecting groups when no longer needed or desired, and would be readily capable of determining other synthetic approaches.

Some additional transformations of potential interest to the practitioner are shown below, including the preparation of reagents for generating the described C-43 phosphorus-containing rapalogs:

Preparation of Diakyl/diaryl Chlorophoshates

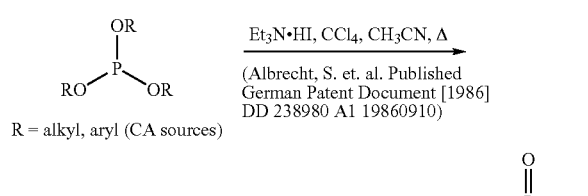

R = alkyl, aryl (CA sources)

(Albrecht, S. et. al. Published German Patent Document [1986] DD 238980 A1 19860910)

Preparation of Alkyl Halide Phosphonates

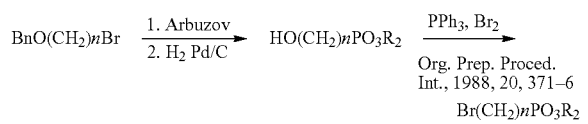

Org. Prep. Proced. Int., 1988, 20, 371–6

Illustrative routes for using the foregoing sorts of reagents to prepare certain rapalogs of this invention are shown below.

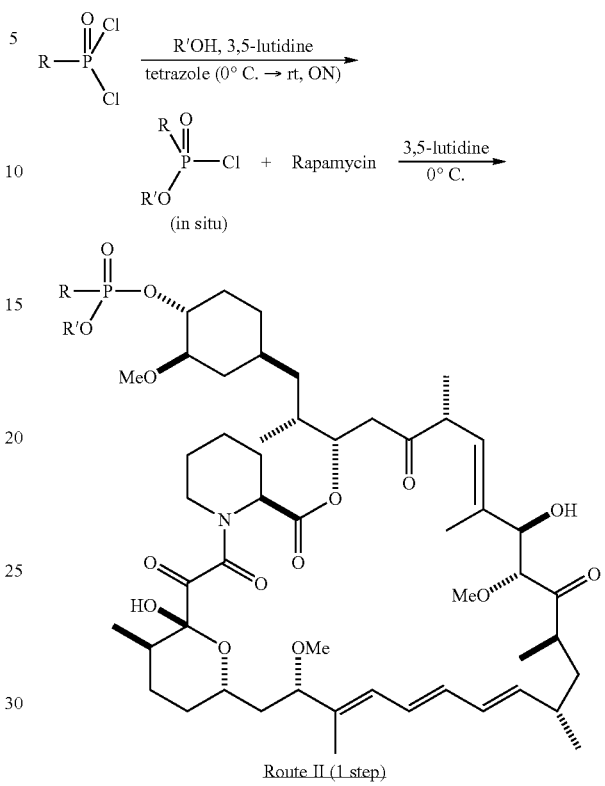

The synthesis of compounds of this invention often involves preparation of an activated form of the desired moiety "J", such as a phosphoryl chloride as shown above (e.g. (R)(RO)P—Cl or RR'P(=O)—Cl, etc), and reaction of that reagent with rapamycin (or the appropriate rapalog) under conditions yielding the desired product, which may then be recovered from residual reactants and any undesired side products. Protecting groups may be chosen, added and removed as appropriate using conventional methods and materials.

Purification of Compounds of the Invention

A variety of materials and methods for purifying rapamycin and various rapalogs have been reported in the scientific and patent literatures and may be adapted to purification of the rapalogs disclosed herein. Flash chromatography using a BIOTAGE prepacked cartridge system has been particularly effective. A typical protocol is disclosed in the Examples which follow.

Physicochemical Characterization of Compounds of the Invention

The identity, purity and chemical/physical properties of the rapalogs may be determined or confirmed using known methods and materials, including HPLC, mass spectral analysis, X ray crystallography and NMR spectroscopy. High resolution 1D $^1$H and $^{31}$P NMR spectra acquired using a typical relaxation delay of 3 seconds have proved useful, as has reverse phase HPLC analysis (analytical column, 3 micron particle size, 120 ansgstrom pore size, thermostatted to 50° C. with a mobile phase of 50% acetonitrile, 5% methanol and 45% water (all % s by volume), for example, in an isocratic elution system, with elution of product and impurity peaks followed by UV detection at 280 nanometers). Normal phase HPLC may also be used, especially to evaluate the level of residual rapamycin or rapalog byproducts. The presence of residual solvent, heavy metals, moisture and bioburden may be assessed using conventional methods.

Biological Characterization of Compounds of the Invention

The biological properties of the rapalogs may be determined using known methods and materials, including e.g. assays measuring binding to FKBP12, inhibition of T cell proliferation, anti-fungal activity, antitumor activity In vitro or in vivo (e.g. against one or more cancer cell lines in vitro and/or in vivo), immunosuppressive activity, and activity in a 3-hybrid assay based on FKBP- and FRAP-containing fusion proteins. Examples of many such assays are disclosed or referenced in Sorbera et al, Drugs of the Future 2002, 27(1): 7–13, which is incorporated herein by reference.

The following will be of particular interest in connection with binding of the rapalogs to FKBP12.

Binding Properties, Assays

Rapamycin is known to bind to the human protein, FKBP12 and to form a tripartite complex with hFKBP12 and FRAP, a human counterpart to the yeast proteins TOR1 and TOR2. Rapalogs may be characterized and compared to rapamycin with respect to their ability to bind to human FKBP12 and/or to form tripartite complexes with human FKBP12 and human FRAP (or fusion proteins or fragments containing its FRB domain). See WO 96/41865 (Clackson et al). That application discloses various materials and methods which can be used to quantify the ability of a compound to bind to human FKBP12 or to form a tripartite complex with (i.e., "heterodimerize") proteins comprising human FKBP12 and the FRB domain of human FRAP, respectively. Such assays include fluorescence polarization assays to measure binding. Other useful assays include cell based transcription assays in which the ability of a rapalog to form the tripartite complex is measured indirectly by correlation with the observed level of reporter gene product produced by engineered mammalian cells in the presence of the compound. Corresponding cell-based assays may also be conducted in engineered yeast cells. See e.g. WO 95/33052 (Berlin et al).

It will often be preferred that the rapalogs of this invention be physiologically acceptable (i.e., lack undue toxicity toward the cell or organism with which it is to be used), can be administered orally or parenterally to animals and/or can cross cellular and other membranes, as necessary for a particular application.

In some cases, e.g. for use in antifungal applications or to trigger a genetically engineered biological switch, preferred rapalogs are those which bind to mutant or fungal binding proteins preferentially over the human counterpart binding proteins. A non-limiting example of a mutant binding protein is a human FKBP in which Phe36 is replaced with a different amino acid, preferably an amino acid with a less bulky side chain such as valine or alanine). For example, such compounds may bind preferentially to mutant FKBPs at least an order of magnitude better than they bind to human FKBP12, and in some cases may bind to mutant FKBPs greater than 2 or even 3 or more orders of magnitude better than they do to human FKBP12, as determined by any scientifically valid or art-accepted assay methodology.

Binding affinities of various rapalogs of this invention with respect to human FKBP12, variants thereof or other immunophilin proteins may be determined by adaptation of known methods used in the case of FKBP. For instance, the practitioner may measure the ability of a compound of this invention to compete with the binding of a known ligand to the protein of interest. See e.g. Sierkierka et al, 1989, Nature 341, 755–757 (test compound competes with binding of labeled FK506 derivative to FKBP).

Certain rapalogs of this invention which are of particular interest bind to human FKBP12, to a mutant thereof as discussed above, or to a fusion protein containing such FKBP domains, with a Kd value below about 200 nM, more preferably below about 50 nM, even more preferably below about 10 nM, and even more preferably below about 1 nM, as measured by direct binding measurement (e.g. fluorescence quenching), competition binding measurement (e.g. versus FK506), inhibition of FKBP enzyme activity (rotamase), or other assay methodology.

A known Competitive Binding FP Assay is described in detail in WO99/36553 and WO96/41865. That assay permits the in vitro measurement of an IC50 value for a given compound which reflects its ability to bind to an FKBP protein in competition with a labeled FKBP ligand, such as, for example, FK506.

One interesting class of compounds of this invention have an IC50 value in the Competitive Binding FP Assay (e.g., using a flouresceinated FK506 standard) of better than 1000 nM, preferably better than 300 nM, more preferably better than 100 nM, and even more preferably better than 10 nM with respect to a given FKBP domain and ligand pair, e.g. human FKBP12 or a variant thereof with up to 10 amino acid replacements, preferably 1–5 amino acid replacements.

The ability of the rapalogs to multimerize chimeric proteins may be measured in cell-based assays by measuring the occurrence of an event triggered by such multimerization. For instance, one may use cells containing and capable of expressing DNA encoding a first chimeric protein comprising one or more FKBP-domains and one or more effector domains as well as DNA encoding a second chimeric protein containing an FRB domain and one or more effector domains capable, upon multimerization, of actuating a biological response. We prefer to use cells which further contain a reporter gene under the transcriptional control of a regulatory element (i.e., promoter) which is responsive to the multimerization of the chimeric proteins. The design and preparation of illustrative components and their use in so engineered cells is described in WO99/36553 and WO96/41865 and the other international patent applications referred to in this and the foregoing section. (See also WO99/10510 for additional guidance on the design, assembly and delivery of nucleic acids to render cells and animals responsive to rapalogs of interest and for additional guidance on applications of such systems.) The cells are grown or maintained in culture. A rapalog is added to the culture medium and after a suitable incubation period (to permit gene expression and secretion, e.g. several hours or overnight) the presence of the reporter gene product is measured. Positive results, i.e., multimerization, correlates with transcription of the reporter gene as observed by the appearance of the reporter gene product. The reporter gene product may be a conveniently detectable protein (e.g. by ELISA) or may catalyze the production of a conveniently detectable product (e.g. colored). Materials and methods for producing appropriate cell lines for conducting such assays are disclosed in the international patent applications cited above in this section. Typically used target genes include by way of example SEAP, hGH, beta-galactosidase, Green Fluorescent Protein and luciferase, for which convenient assays are commercially available.

Conducting such assays permits the practitioner to select rapalogs possessing the desired IC50 values and/or binding characteristics. The Competitive Binding FP Assay permits one to select rapalogs which possess the desired IC50 values and/or binding preference for a mutant FKBP or wild-type FKBP relative to a control, such as FK506.

Applications

The rapalogs of this invention can be used as described in WO94/18317, WO95/02684, WO96/20951, WO95/41865, WO99/36553 and WO/01/14387, e.g. to regulatably activate the transcription of a desired gene, delete a target gene, actuate apoptosis, or trigger other biological events in engineered cells growing in culture or in whole organisms, including in gene therapy applications. Additionally, certain compounds of this invention possess immunosuppressive and/or anti-cancer and/or antiinflammatory activity and/or anti-proliferative and/or antifungal activity, and/or inhibit thymocyte proliferation in vitro, as can be quantified and compared using conventional assay methods. Those compounds are therefore useful in the treatment or inhibition of organ or tissue transplant rejection; autoimmune diseases such as lupus, rheumatoid arthritis, diabetes mellitus and multiple sclerosis; fungal infection; inflammatory diseases (such as psoriasis, exzema, seborrhea, inflammatory bowel disease and pulmonary inflammation such as asthma, chronic obstructive disease, empheysema, bronchitis, etc.; hyperproliferative vascular disease (e.g., restenosis following the introduction of a vascular stent)(see e.g. Sousa et al, Circulation, 2001, 103:192–195); syndromes such as tuberous sclerosis (see e.g. Kwiatkowski et al, Human Molecular Genetics, 2002, vol 11, No. 5, pp 525–534) and certain cancers (e.g., tumors of the breast, prostate, ovarian, lung, pancreatic, colon, head and- neck, glioblastoma or other cancers of the brain, melanoma, and cervix) especially PTEN-deficient tumors (see e.g. Neshat et al, PNAS 98(18): 10314 10319; Podsypanina et al, PNAS 98(18):01320–10325; Mills et al PNAS 98(18):10031–10033; Hidalgo et al, Oncogene (2000) 19, 6680–6686). Cert compounds of the invention will be of interest for their ability to inhibit osteoclast function, and may be useful in treating patients with debilitating bone disorders such as osteoporosis, particularly osteoporosis associated with the peri and post menopausal conditions. We also contemplate the administration of compounds of this invention for the treatment of patients who have, or are at risk of, Paget's disease, hypercalcemia associated with bone neoplasms and other types of osteoporotic diseases and related disorders, including but not limited to involutional osteoporosis, Type I or postmenopausal osteoporosis, Type II or senile osteoporosis, juvenile osteoporosis, idiopathic osteoporosis, endocrine abnormality, hyperthyroidism, hypogonadism, ovarian agensis or Turner's syndrome, hyperadrenocorticism or Cushing's syndrome, hyperparathyroidism, bone marrow abnormalities, multiple myeloma and related disorders, systemic mastocytosis, disseminated carcinoma, Gaucher's disease, connective tissue abnormalities, osteogenesis imperfecta, homocystinuria, Ehlers-Danlos syndrome, Marfan's syndrome, Menke's syndrome, immobilization or weightlessness, Sudeck's atrophy, chronic obstructive pulmonary disease, chronic heparin administration, and chronic ingestion of anticonvulsant drugs.

Several of these uses are further discussed below.

1. Regulated Gene Therapy.

In many instances, the ability to switch a therapeutic gene on and off at will or to titrate its expression level is important for therapeutic efficacy. This invention is particularly well suited for achieving regulated expression of a therapeutic target gene in the context of human gene therapy. One example uses a pair of fusion proteins (one containing at least one FKBP:rapamycin binding domain (an "FRB" domain) of the protein, FRAP, the other containing at least one FKBP domain), a rapalog of this invention capable of dimerizing the fusion proteins, and a target gene construct. One of the fusion proteins comprises a DNA-binding domain, preferably a composite DNA-binding domain as described in Pomerantz et al, supra, as the heterologous effector domain. The second fusion protein comprises a transcriptional activating domain as the heterologous effector domain. The rapalog is capable of binding to both fusion proteins and thus of effectively cross-linking them. DNA molecules encoding and capable of directing the expression of these chimeric proteins are introduced into the cells to be engineered. Also introduced into the cells is a target gene linked to a DNA sequence to which the DNA-binding domain is capable of binding. Contacting the engineered cells or their progeny with the rapalog (by administering it to the animal or patient) leads to assembly of the transcription factor complex and hence to expression of the target gene. The design and use of similar components is disclosed in PCT/US93/01617 and in WO 96/41865 (Clackson et al). In practice, the level of target gene expression should be a function of the number or concentration of chimeric transcription factor complexes, which should in turn be a function of the concentration of the rapalog. Dose (of rapalog)-responsive gene expression is typically observed.

The rapalog may be administered to the recpient as desired to activate transcription of the target gene. Depending upon the binding affinity of the rapalog, the response desired, the manner of administration, the biological half-life of the rapalog and/or target gene mRNA, the number of engineered cells present, various protocols may be employed. The rapalog may be administered by various routes, including parenterally or orally. The number of administrations will depend upon the factors described above. The rapalog may be administered orally as a pill, powder, or dispersion; buccally; sublingually; by inhalation; or by intravascular, intraperitoneal, intramuscular, subcutaneous or intra-articular injection. The rapalog (and monomeric antagonist compound) may be formulated using conventional methods and materials well known in the art for the various routes of administration. The precise dose and particular method of administration will depend upon the above factors and be determined by the attending physician or human or animal healthcare provider. For the most part, the manner of administration will be determined empirically.

In the event that transcriptional activation by the rapalog is to be reversed or terminated, adminstration of the rapalog is terminated. Furthermore, if desired, a monomeric compound which can compete with the rapalog may be administered. Thus, in the case of an adverse reaction or the desire to terminate the therapeutic effect, an antagonist to the dimerizing agent can be administered in any convenient way, particularly intravascularly, if a rapid reversal is desired. Alternatively, one may provide for the presence of an inactivation domain (or transcriptional silencer) with a ligand binding domain.

In another approach, cells are engineered to express a pair of chimeric proteins containing FRB and FKBP domains as discussed above, but containing a cellular signaling domain in place of a DNA binding domain or transcription activation domain. Such signaling domains are known which upon their clustering or dimerization or idfferentiation, trigger cell death, proliferation or idfferentiation. This approach permits rapalog-mediated regulation of cell signaling (i.e., of cell death, proliferation or differentiation) in genetically engineered cells or organisms harboring them, as described elsewhere, which may be adapted for use of rapalogs of this invention. See International Patent Applications PCT/US94/01617 and PCT/US94/08008.

The particular dosage of the rapalog for any application may be determined in accordance with the procedures used for therapeutic dosage monitoring, where maintenance of a particular level of expression is desired over an extended period of times, for example, greater than about two weeks, or where there is repetitive therapy, with individual or repeated doses of rapalog over short periods of time, with extended intervals, for example, two weeks or more. A dose of the rapalog within a predetermined range would be given and monitored for response, so as to obtain a time-expression level relationship, as well as observing therapeutic response. Depending on the levels observed during the time period and the therapeutic response, one could provide a larger or smaller dose the next time, following the response. This process would be iteratively repeated until one obtained a dosage within the therapeutic range. Where the rapalog is chronically administered, once the maintenance dosage of the rapalog is determined, one could then do assays at extended intervals to be assured that the cellular system is providing the appropriate response and level of the expression product.

It should be appreciated that the system is subject to a number of variables, such as the cellular response to the rapalog, the efficiency of expression and, as appropriate, the level of secretion, the activity of the expression product, the particular need of the patient, which may vary with time and circumstances, the rate of loss of the cellular activity as a result of loss of cells or expression activity of individual cells, and the like.

2. Production of Recombinant Proteins and Viruses.

Production of recombinant therapeutic proteins for commercial and investigational purposes is often achieved through the use of mammalian cell lines engineered to express the protein at high level. The use of mammalian cells, rather than bacteria or yeast, is indicated where the proper function of the protein requires post-translational modifications not generally performed by heterologous cells. Examples of proteins produced commercially this way include erythropoietin, tissue plasminogen activator, clotting factors such as Factor VIII:c, antibodies, etc. The cost of producing proteins in this fashion is directly related to the level of expression achieved in the engineered cells. A second limitation on the production of such proteins is toxicity to the host cell: Protein expression may prevent cells from growing to high density, sharply reducing production levels. Therefore, the ability to tightly control protein expression, as described for regulated gene therapy, permits cells to be grown to high density in the absence of protein production. Only after an optimum cell density is reached, is expression of the gene activated and the protein product subsequently harvested.

A similar problem is encountered in the construction and use of "packaging lines" for the production of recombinant viruses for commercial (e.g., gene therapy) and experimental use. These cell lines are engineered to produce viral proteins required for the assembly of infectious viral particles harboring defective recombinant genomes. Viral vectors that are dependent on such packaging lines include retrovirus, adenovirus, and adeno-associated virus. In the latter case, the titer of the virus stock obtained from a packaging line is directly related to the level of production of the viral rep and cap proteins. But these proteins are highly toxic to the host cells. Therefore, it has proven difficult to generate high-titer recombinant AAV viruses. This invention provides a solution to this problem, by allowing the construction of packaging lines in which the rep and core genes are placed under the control of regulatable transcription factors of the design described here. The packaging cell line can be grown to high density, infected with helper virus, and transfected with the recombinant viral genome. Then, expression of the viral proteins encoded by the packaging cells is induced by the addition of dimerizing agent to allow the production of virus at high titer.

3. Biological Research.

This invention is applicable to a wide range of biological experiments in which precise control over the expression of a target gene is desired. These include, among others: (1) expression of a protein or RNA of interest for biochemical purification; (2) regulated expression of a protein or RNA of interest in tissue culture cells (or in vivo, via engineered cells) for the purposes of evaluating its biological function; (3) regulated expression of a protein or RNA of interest in transgenic animals for the purposes of evaluating its biological function; (4) regulating the expression of a gene encoding another regulatory protein, ribozyme or antisense molecule that acts on an endogenous gene for the purposes of evaluating the biological function of that gene. Transgenic animal models and other applications in which the components of this invention may be adapted include those disclosed in PCT/US95/10591.

This invention further provides kits useful for the foregoing applications. Such kits contain DNA constructs encoding and capable of directing the expression of chimeric proteins of this invention (and may contain additional domains as discussed above) and, in embodiments involving regulated gene transcription, a target gene construct containing a target gene linked to one or more transcriptional control elements which are activated by the multimerization of the chimeric proteins. Alternatively, the target gene construct may contain a cloning site for insertion of a desired target gene by the practitioner. Such kits may also contain a sample of a dimerizing agent capable of dimerizing the two recombinant proteins and activating transcription of the target gene. Kits can also be provided for genetic engineering of cells or organisms to permit drug-regulated cellular signaling (e.g., leading to cell proliferation, differentiation or death) using rapalogs of this invention.

4. Several Other Pharmaceutical Uses.

Compounds of this invention which were tested for activity against a variety of cancer cell lines were found to inhibit cancer cell growth and are therefore useful as antineoplastic agents. In particular, the compounds of this invention may be used alone or in combination with other drugs and/or radiation therapy in treating or inhibiting the growth of various cancers, including leukemias and solid tumors, including sarcomas and carcinomas, such as astrocytomas, prostate cancer, breast cancer, small cell lung cancer, and ovarian cancer. Their use is analogous to that of rapamycin or CCI779 as disclosed in Sorbera et al, "CCI-779" Drugs of the Future 2002, 27(1):7–13; WO 02/4000 and WO 02/13802, for example. Examples of other drugs that can be used to treat cancer patients in conjunction with (i.e., before, during or after administration of a compound of this invention) a compound of this invention include, among others, Zyloprim, alemtuzmab, altretamine, amifostine, nastrozole, antibodies against prostate-specific membrane antigen (such as MLN-591, MLN591RL and MLN2704), arsenic trioxide, Avastin® (or other anti-VEGF antibody), bexarotene, bleomycin, busulfan, capecitabine, carboplatin, Gliadel Wafer, celecoxib, chlorambucil, cisplatin, cisplatin-epinephrine gel, cladribine, cytarabine liposomal, daunorubicin liposomal, daunorubicin, daunomycin, dexrazoxane, docetaxel, doxorubicin, Elliott's B Solution, epirubicin, estramustine, etoposide phosphate, etoposide, VP-16, exemestane, fludarabine, 5-FU, fulvestrant, gemcitabine, gemtuzumab-ozogamicin, goserelin acetate, hydroxyurea, idarubicin, idarubicin, ldamycin, ifosfamide, imatinib mesylate, irinotecan (or other topoisomerase inhibitor, including antibodies such as MLN576 (XR11576)), letrozole, leucovorin, leucovorin levamisole,liposomal daunorubicin, melphalan, L-PAM, mesna, methotrexate, methoxsalen, mitomycin C, mitoxantrone, MLN518 or MLN608 (or other inhibitors of the fit-3 receptor tyrosine kinase, PDFG-R or c-kit), itoxantrone, paclitaxel, Pegademase, pentostatin, porfimer sodium, Rituximab (RITUXAN®), talc, tamoxifen, temozolamide, teniposide, VM-26, topotecan, toremifene, Trastuzumab (Herceptin®, or other anti-Her2 antibody), 2C4 (or other antibody which interferes with HER2-mediated signaling), tretinoin, ATRA, valrubicin, vinorelbine, or pamidronate, zoledronate or another bisphosphonate.

The compounds of this invention may also be used for the treatment or inhibition of rejection of transplanted tissues including, e.g., kidney, heart, liver, lung, bone marrow, pancreas (islet cells), cornea, small bowel, and skin allografts, and heart valve xenografts; in the treatment or inhibition of graft vs. host disease; in the treatment or inhibition of autoimmune diseases such as lupus, rheumatoid arthritis, diabetes mellitus, myasthenia gravis, and multiple sclerosis; and diseases of inflammation such as psoriasis, dermatitis, eczema, seborrhea, inflammatory bowel disease, pulmonary inflammation (including asthma, chronic obstructive pulmonary disease, emphysema, acute respiratory distress syndrome, bronchitis, and the like) and ocular uveitis; adult T-cell leukemia/lymphoma; fungal infections; hyperproliferative vascular diseases including restenosis; graft vascular atherosclerosis; and cardiovascular disease, cerebral vascular disease, and peripheral vascular disease, such as coronary artery disease, cerebrovacular disease, arteriosclerosis, atherosclerosis, nonatheromatous arteriosclerosis, or vascular wall damage from cellular events leading toward immune mediated vascular damage, and inhibiting stroke or multiinfarct dementia. Methods and materials for using rapalogs of this invention for such applications may be adapted from those used with rapamycin, CCI779 or RAD001.

When used as an immunosuppressive or antiinflammatory agent, a rapalog of this invention can be administered in conjunction with one or more other immunoregulatory agents. Such other immunoregulatory agents include, but are not limited to azathioprine, corticosteroids, such as prednisone and methylprednisolone, cyclophosphamide, rapamycin, cyclosporin A, FK-506, OKT-3, mycophenolate, and ATG. By combining the compounds of this invention with such other drugs or agents for inducing immunosuppression or treating inflammatory conditions, the lesser amounts of each of the agents may be required to achieve the desired effect. The basis for such combination therapy was established by Stepkowski whose results showed that the use of a combination of rapamycin and cyclosporin A at individually subtherapeutic doses significantly prolonged heart allograft survival time. [Transplantation Proc. 23: 507 (1991)]. Rapalogs of this invention may be used for treating cardiac inflammatory disease, e.g., by adaptation of the methods and materials disclosed in U.S. Pat. No. 5,496,832; for treating ocular inflammation, e.g., by adaptation of the methods and materials disclosed in U.S. Pat. No. 5,387,589; and for treating immunoinflammatory bowel disease and other immunoinflammatory diseases, e.g., by adaptation of the methods and materials disclosed in U.S. Pat. Nos. 5,286,731 and 5,286,730.

Rapalogs of this invention may also be used in the treatment or inhibition of vascular disease (including among others, coronary artery disease, cerebrovascular disease, arteriosclerosis, atherosclerosis, nonatheromatous arteriosclerosis, vascular wall damage from cellular events leading toward immune mediated vascular damage, stroke and multiinfarct dementia) to provide cardiovascular, cerebral, or peripheral vascular benefits as the sole active ingredient, or may be administered in combination with other agents which provide beneficial cardiovascular, cerebral, or peripheral vascular effects. Such agents include ACE inhibitors, such as quinapril, perindopril, ramipril, captopril, trandolapril, fosinopril, lisinopril, moexipril, and enalapril; angiotensin II receptor antagonists, such as candesartan, irbesartan, losartan, valsartan, and telmisartan; fibric acid derivatives, such as clofibrate, and gemfibrozil; HMG Co-A reductase inhibitors, such as cerivastatin, fluvastatin, atorvastatin, lovastatin, pravastatin, simvastatin; beta adrenergic blocking agents, such as sotalol, timolol, esmolol, carteolol, propranolol, betaxolol, penbutolol, nadolol, acebutolol, atenolol, metoprolol, and bisoprolol; calcium channel blockers, such as nifedipine, verapamil, nicardipine, diltiazem, nimodipine, amlodipine, felodipine, nisoldipine, and bepridil; antioxidants; anticoagulants such as, warfarin, dalteparin, heparin, enoxaparin, and danaparoid; and agents useful in hormone replacement therapy containing estrogens, such as conjugated estrogens, ethinyl estradiol, 17-beta-estradiol, estradiol, and estropipate. See e.g. U.S. Pat. No. 5,288,711 or WO01/97809 for methods and materials which may be adapted to the use of rapalogs of this invention for treating various diseases, including hyperproliferative and other vascular diseases.

The compounds of this invention may also be used as neurotrophic agents, and may be particularly useful in promoting neuronal regeneration and functional recovery and in stimulating neurite outgrowth and thus treatment of various neuropathological states, including damage to peripheral nerves and the central nervous system caused by physical injury (e.g., spinal cord injury and trauma, sciatic or facial nerve lesion or injury), disease (e.g., diabetic neuropathy), cancer chemotherapy (e.g., by vinca alkaloids and doxorubicin), brain damage associated with stroke and ischemia associated with stroke, and neurological disorders including, but not limited to, various peripheral neuropathic and neurological disorders related to neurodegeneration including, but not limited to: trigeminal neuralgia, glossopharyngeal neuralgia, Bell's palsy, myasthenia gravis, muscular dystrophy, amyotrophic lateral sclerosis, progressive muscular atrophy, progressive bulbar inherited muscular atrophy, herniated, ruptured or prolapsed vertebral disk syndromes, cervical spondylosis, plexus disorders, thoracic outlet destruction syndromes, peripheral neuropathies such as those caused by lead, acrylamides, gamma-diketones (glue-sniffer's neuropathy), carbon disulfide, dapsone; ticks, porphyria, Gullain-Barre syndrome, dementia, Alzheimer's disease, Parkinson's disease, and Huntington's chorea.

5. Use for Preventing Restenosis; Use with Stents or Other Devices

A rapalog of this invention may be used by itself or in conjunction with mycophenolic acid, e.g. by adaptation of the methods and materials disclosed in U.S. Pat. No. 5,665,728, in treating or reducing the risk or severity of intimal smooth muscle cell hyperplasia, restenosis, and vascular occlusion in a mammal, particularly following either biologically or mechanically mediated vascular injury, or under conditions that would predispose a mammal to suffering such a vascular injury. Biologically mediated vascular injury includes injury attributed to infectious disorders including endotoxins and herpes viruses such as cytomegalovirus; metabolic disorders such as atherosclerosis; and vascular injury resulting from hypothermia, and irradiation, among others. Mechanically mediated vascular injury includes, among others, vascular injury caused by catheterization procedures or vascular scraping procedures such as percutaneous transluminal coronary angioplasty; vascular surgery; transplantation surgery; laser treatment; and other invasive procedures which disrupt the integrity of the vascular intima or endothelium. Thus, alone or in combination with mycophenolic acid, a rapalog of this invention may be used in preventing restenosis following invasive procedures that disrupt the vascular endothelial lining, such as percutaneous transluminal coronary angioplasty, vascular catheterization, vascular scraping, vascular surgery, or laser treatment procedures.

One application of particular interest involves the use of a rapalog of this invention for treating or reducing the likelihood of restenosis such as occurs in a portion of patients following an angioplasty procedure. When used in such methods, the compounds of this invention can be administered prior to the angioplasty procedure, during the procedure, subsequent to the procedure, or any combination of the above. Of great interest is the use of a rapalog of this invention delivered on or in a stent (or other inserted or implanted device) in order to reduce the chances of restenosis following introduction of the device. The use of a rapalog of this invention with a stent may be achieved by adapting the methods and materials used for the delivery of other drugs (including rapamycin and paclitaxel among others) using such devises, e.g. as disclosed in U.S. Pat. Nos. 5,516,781; 6,153,252; 5,665,728; 5,646,160; 5,563,146; and 5,516,781 as well as in published international patent applications WO 01/01957, 01/49338, 01/87263, 01/87342, 01/87372, 01/87373, 01/87374, 01/87375, and 01/87376 and other patent documents relating to stents and other drug-bearing devices noted elsewhere herein. Rapalogs of this invention are broadly compatible across the range of stent designs and of methods and materials for coating or otherwise loading them with drug. Loading such medical devices with a rapalog of this invention, medical devices loaded with a rapalog of this invention and the insertion of such a device loaded with such a rapalog are all encompassed by this invention.

Generally speaking, a rapalog-bearing device of this invention comprises an expansible structure which is implantable within a body lumen and a means on or within the structure for releasing a compound of this invention, in some cases at a pre-selected rate. Release of the compound may be at rates in a range from 5 µg/day to 200 µg/day, preferably in a range from 10 µg/day to 60 µg/day. The total amount of compound released will in some cases be in a range from 100 µg to 10 mg, preferably in a range from 300 µg to 2 mg, more preferably in a range from 500 µg to 1.5 mg.

The expansible structure may be in the form of a stent, which additionally maintains luminal patency, or may be in the form of a graft, which additionally protects or enhances the strength of a luminal wall. The expansible structure may be radially expansible and/or self-expanding and is preferably suitable for luminal placement in a body lumen. The site of implantation may be any blood vessel in the patient's vasculature, including veins, arteries, aorta, and particularly including coronary and peripheral arteries, as well as previously implanted grafts, shunts, fistulas, and the like, or other body lumens, such as the biliary duct, or other organs, such as organs, nerves, glands, ducts, and the like. Exemplary stents for use in the present invention include the Duraflex Coronary Stent (Avantec), Multi-Link Zeta or Vision stent (Guidant), S7 Stent (Medtronic), Express Stent (Boston Scientific), and the Bx Velocity or Cypher stent (J&J), as well as other stents mentioned previously.

Radially "expansible" devices or segments thereof are those which can be converted from a small diameter configuration to a radially expanded, usually cylindrical, configuration when the device is implanted at a desired target site. The device may be minimally resilient, e.g., malleable, thus requiring the application of an internal force to expand and set it at the target site. The expansive force is often provided by a balloon, such as the balloon of an angioplasty catheter for vascular procedures. The device may provide sigmoidal links between successive unit segments which can be useful for enhancing flexibility and crimpability of the stent.

Alternatively, the device can be self-expanding. Such self-expanding structures are provided by using a resilient material, such as a tempered stainless steel or a super-elastic alloy such as a Nitinol™ alloy. The body segment is formed from the resilient material so that it possesses its desired, radially-expanded diameter when it is unconstrained, i.e. released from the radially constraining forces of a sheath. In order to remain anchored in the body lumen, the device will remain partially constrained by the lumen. The self-expanding device can be tracked and delivered in its radially constrained configuration, e.g., by placing the device within a delivery sheath or tube and removing the sheath at the target site.

The dimensions of the device will depend on its intended use. Typically, the device will have a length in a range from about 5 mm to 100 mm, usually being from about 8 mm to 50 mm, for vascular applications. The small (radially collapsed) diameter of cylindrical device will usually be in a range from about 0.5 mm to 10 mm, more usually being in a range from 0.8 mm to 8 mm for vascular applications. The expanded diameter will usually be in a range from about 1.0 mm to 100 mm, preferably being in a range from about 2.0 mm to 30 mm for vascular applications. The device will have a thickness in a range from 0.025 mm to 2.0 mm, preferably being in a range from 0.05 mm to 0.5 mm.

The device, or its segments or structural component(s), may be formed from conventional materials used for body lumen stents and grafts, typically being formed from malleable metals, such as 300 series stainless steel, or from resilient metals, such as superelastic and shape memory alloys, e.g., Nitinol™ alloys, spring stainless steels, and the like. It may be formed from combinations of these metals, or combinations of these types of metals and other non-metallic materials. Additional examples of structures for the body or unit segments of the device are illustrated in U.S. Pat. Nos. 5,195,417; 5,102,417; and 4,776,337, the full disclosures of which are incorporated herein by reference. Examplary stents and delayed or staged release of drug, including at preselected rates, are described in U.S. Pat. No. 6,471,980, the full disclosure of which is also incorporated herein by reference.

In an illustrative embodiment, the means for releasing the compound comprises a matrix formed over at least a portion of the structure. The matrix may be composed of a material which is degradable, partially degradable, nondegradable polymer, synthetic, or natural material. The compound may be disposed within the matrix or adjacent to the matrix in a pattern that provides a desired release rate. Alternatively, compound may be disposed on or within the expansible structure adjacent to the matrix to provide the desired release rate. Suitable biodegradable or bioerodible matrix materials include polyanhydrides, polyorthoesters, polycaprolactone, poly vinly acetate, polyhydroxybutyrate-polyhyroxyvalerate, polyglycolic acid, polyactic/polyglycolic acid copolymers and other aliphatic polyesters, among a wide variety of polymeric substrates employed for this purpose. An often preferred biodegradable matrix material is a copolymer of poly-1-lactic acid and poly-e-caprolactone. Suitable nondegradable matrix materials include polyurethane, polyethylene imine, cellulose acetate butyrate, ethylene vinyl alcohol copolymer, or the like.

An example of a biodegradable matrix material useful in practicing the present invention is a copolymer of poly-1-lactic acid (having an average molecular weight of about 200,000 daltons) and poly-e-caprolactone (having an average molecular weight of about 30,000 daltons). Poly-e-caprolactone (PCL) is a semi crystalline polymer with a melting point in a range from 59° C. to 64° C. and a degradation time of about 2 years. Thus, poly-1-lactic acid (PLLA) can be combined with PCL to form a matrix that generates the desired release rates. A preferred ratio of PLLA to PCL is 75:25 (PLLA/PCL). As generally described by Rajasubramanian et al. in ASAIO Journal, 40, pp. M584-589 (1994), the full disclosure of which is incorporated herein by reference, a 75:25 PLLA/PCL copolymer blend exhibits sufficient strength and tensile properties to allow for easier coating of the PLLA/PLA matrix on the scaffold. Additionally, a 75:25 PLLA/PCL copolymer matrix allows for controlled drug delivery over a predetermined time period as a lower PCL content makes the copolymer blend less hydrophobic while a higher PLLA content leads to reduced bulk porosity.

The polymer matrix may degrade by bulk degradation (i.e., in which the matrix degrades throughout) or by surface degradation (i.e., in which a surface of the matrix degrades over time while maintaining bulk integrity). Hydrophobic matrices are sometimes preferred as they tend to release compound at a predetermined release rate. Alternatively, a nondegradable matrix may be used to release the substance by diffusion. Suitable nondegradable matrix materials include polyurethane, polyethylene imine, cellulose acetate butyrate, ethylene vinyl alcohol copolymer, or the like.

The matrix may comprise multiple layers, each layer containing the rapalog compound of this invention, a different substance, or no substance (with the various layers containing the same or diffent matrix mateirlal). A top layer may contain no substance while a bottom layer contains the compound. As the top layer degrades, the compound delivery rate increases. In other cases, compound disposed within a top degradable layer of the matrix is released as the top matrix layer degrades and a second substance disposed within an adjacent nondegradable matrix layer is released primarily by diffusion. In some instances, multiple substances may be disposed within a single matrix layer. Optional substances which may be used in addition to the compound of this invention may, for example, be selected from those listed in U.S. Pat. No. 6,471,980. Additionally, the present invention may employ a rate limiting barrier formed between the device and the matrix, or may optionally be formed over the matrix. Such rate limiting barriers may be nonerodible and control the flow rate of release by diffusion of the compound through the barrier. Suitable nonerodible rate limiting barriers include silicone, PTFE, PARYLAST™, and the like. Furthermore, a layer such as polyethylene glycol (PEG), and the like, may be formed over the matrix to make the delivery device more biocompatible.

In some cases the means for releasing the compound includes a rate limiting barrier formed over at least a portion of the structure. The compound may be disposed within the barrier or adjacent to the barrier, e.g., in a layer covered directly or indirectly by the barrier. The rate limiting barrier may have a sufficient thickness so as to provide the desired release rate of compound. Rate limiting barriers will typically have a total thickness in a range from 0.01 micron to 100 microns, preferably in a range from 0.1 micron to 10 microns, to provide compound release at the desired release rate. The rate limiting barrier is typically nonerodible such as silicone, polytetrafluorethylene (PTFE), PARYLAST™, polyurethane, parylene, or a combination thereof and compound release through such rate limiting barriers is usually accomplished by diffusion. In some instances, the rate limiting barrier may comprise multiple adjacent layers of same or different barrier material, wherein at least one layer contains compound and another layer contains compound, at least one substance other than compound, or no substance. Multiple substances may also be contained within a single barrier layer. Furthermore, a biocompatible or blood compatible layer, such as polyethylene glycol (PEG), may be formed over the matrix or rate limiting barrier to make the delivery prosthesis more biocompatible.

In other cases, the means for releasing the substance comprises a reservoir on or within the structure containing compound and a cover over the reservoir. The cover may be degradable or partially degradable over a preselected time period so as to provide the desired compound release rate. The cover may comprise a polymer matrix, as described above, which contains compound within the reservoir. A rate limiting barrier, such as silicone, may additionally be formed adjacent to the reservoir and/or the cover, thus allowing compound to be released by diffusion through the rate limiting barrier. Alternatively, the cover may be a nondegradable matrix or a rate limiting barrier.

Another device of this invention comprises an expansible structure which is implantable within a body lumen with a rate limiting barrier on the structure permitting release of compound at a pre-selected rate, e.g., a rate selected to inhibit smooth muscle cell proliferation. The barrier comprises multiple layers, wherein each layer comprises PARYLAST™ or parylene and has a thickness in a range of 50 nm–10 microns. At least one layer contains compound, and another layer contains compound, at least one substance other than compound, or no substance.

Another such device is a vascular prosthesis which comprises an expansible structure, a source of compound on or within the structure, and optionally a source of at least one other substance in addition to compound on or within the structure. The compound is released from the source when the expansible structure is implanted in a blood vessel. The optional additional substance is also released from its source when the expansible structure is implanted in a blood vessel. Each source may comprise a matrix, rate limiting membrane, reservoir, or other rate controlling means as described herein. Examples of the optional additional substance include an immunosuppressive substance (e.g., mycophenolic acid or an analog thereof, anti-platelet agent, anti-thrombotic agent, or IIb/IIIa agent such as disclosed in U.S. Pat. No. 6,471,980.

This invention thus provides methods for inhibiting restenosis in a blood vessel following recanalization of the blood vessel. For example, one method includes implanting a vascular prosthesis, bearing a compound of this invention, in the body lumen such as a coronary or peripheral blood vessel, for instance, to prevent reclosure of the vessel. The compound is then released, in some cases at a rate selected to inhibit smooth muscle cell proliferation. The release of the compound may occur immediately upon introduction or expansion of the stent, or the release may be delayed. Thus, in some cases substantial release of compound may be delayed for at least one hour following implantation of the prosthesis. The delayed release from its reservoir may be provided using with a material that at least partially degrades in a vascular environment over that one hour. In some instances, release may be slowed by the use of a matrix that at least partially degrades in a vascular environment over that one hour. In other instances, release may be slowed with a nondegradable matrix or rate limiting barrier that allows diffusion of compound through said nondegradable matrix or barrier after that hour. The release of compound will typically be at rates in a range from 5 µg/day to 200 µg/day, preferably in a range from 10 µg/day to 60 µg/day. Typically, compound is released within a time period of 1 day to 45 days in a vascular environment, preferably in a time period of 7 day to 21 days in a vascular environment.

The device may be coated with a matrix or barrier by spraying, dipping, deposition, or painting. Such coatings may be non-uniform. For example, the coating may be applied to only one side of the prosthesis or the coating may be thicker on one side. Likewise, the device may also incorporate the compound by virtue of coating, spraying, dipping, deposition, chemical bonding, or painting compound on all or partial surfaces of the device.

In cases in which the device also bears at least one additional substance in addition to the compound, the compound may be released within a time period of 1 day to 45 days and the additional substance or substances may be released within a time period of 2 days to 3 months. Thus, release of the compound and the additional substance(s) may be simultaneous or sequential.

The total amount of the compound released depends in part on the level and amount of vessel injury. In some embodiments the release rate will be in a range from 100 µg to 10 mg, preferably in a range from 300 µg to 2 mg, more preferably in a range from 500 µg to 1.5 mg. It is often preferred that the release rate during the initial phase be from 0 µg/day to 50 µg/day, usually from 5 µg/day to 30 µg/day. The compound release rate during the subsequent phase will be much higher, typically being in the range from 5 µg/day to 200 µg/day, usually from 10 µg/day to 100 µg/day. Thus, the initial release rate will typically be from 0% to 99% of the subsequent release rates, usually from 0% to 90%, preferably from 0% to 75%. A mammalian tissue concentration of the compound at an initial phase will typically be within a range from 0 µg/mg of tissue to 100 µg/mg of tissue, preferably from 0 µg/mg of tissue to 10 µg/mg of tissue. A mammalian tissue concentration of the substance at a subsequent phase will typically be within a range from 1 picogram/mg of tissue to 100 µg/mg of tissue, preferably from 1 nanogram/mg of tissue to 10 µg/mg of tissue.

The duration of the initial, subsequent, and any other additional phases may vary. Typically, the initial phase will be sufficiently long to allow initial cellularization or endothelialization of at least part of the stent, usually being less than 12 weeks, more usually from 1 hour to 8 weeks, more preferably from 12 hours to 2 weeks, most preferably from 1 day to 1 week. The durations of the subsequent phases may also vary, typically being from 4 hours to 24 weeks, more usually from 1 day to 12 weeks, more preferably in a time period of 2 days to 8 weeks in a vascular environment, most preferably in a time period of 3 days to 50 days in a vascular environment.

In some instances, the release profile of the compound over a predetermined time may allow for a higher release rate during an initial phase, typically from 40 µg/day to 300 µg/day, usually from 40 µg/day to 200 µg/day. In such instances, the compound release during the subsequent phase will be much lower, typically being in the range from 1 µg/day to 100 µg/day, usually from 10 µg/day to 40 µg/day. The duration of the initial phase period for the higher release rate will be in a range from 1 day to 7 days, with the subsequent phase period for the lower release rate being in a range from 2 days to 45 days. A mammalian tissue concentration of the substance at the initial phase of 1–7 days will typically be within a range from 10 nanogram/mg of tissue to 100 µg/mg of tissue. A mammalian tissue concentration of the substance at the subsequent phase of 2–45 days will typically be within a range from 0.1 nanogram/mg of tissue to 10 µg/mg of tissue. In other instances, the release of the compound may be constant at a rate between 5 µg/day to 200 µg/day for a duration of time in the range from 1 day to 45 days. A mammalian tissue concentration over this period of 1–45 days will typically be within a range from 1 nanogram/mg of tissue to 10 µg/mg of tissue.

In operation, methods for the compound delivery comprise providing a luminal prosthesis incorporating or bearing the compound. The prosthesis is coated with a matrix which undergoes degradation in a vascular environment. The prosthesis is implanted in a body lumen so that at least a portion of the matrix degrades over a predetermined time period and substantial the compound release begins after the portion has degraded. Optionally, the prosthesis may be coated with a rate limiting barrier or nondegradable matrix having a sufficient thickness to allow diffusion of the compound through the barrier or nondegradable matrix. The prosthesis is implanted in a body lumen so that substantial release of compound from the barrier or nondegradable matrix begins, preferably after a preselected time period. As the proliferative effects of restenosis usually occur within a few weeks to a few months, substantial release of the compound in some embodiments will begin within a time period of 4 hours to 24 weeks in a vascular environment, preferably in a time period of 1 day to 12 weeks in a vascular environment, more preferably in a time period of 2 days to 8 weeks in a vascular environment, most preferably in a time period of 3 days to 50 days in a vascular environment.

The prosthesis may incorporate the compound by coating, spraying, dipping, deposition, or painting the compound on the prosthesis. Usually, the compound is dissolved in a solvent to make a solution. Suitable solvents include aqueous solvents (e.g., water with pH buffers, pH adjusters, organic salts, and inorganic salts), alcohols (e.g., methanol, ethanol, propanol, isopropanol, hexanol, and glycols), nitrites (e.g., acetonitrile, benzonitrile, and butyronitrile), amides (e.g., formamide and N dimethylformamide), ketones, esters, ethers, DMSO, gases (e.g., carbon dioxide), and the like. For example, the prosthesis may be sprayed with or dipped in the solution and dried so that the compound crystals are left on a surface of the prosthesis. Alternatively, the prosthesis may be coated with the matrix solution by spraying, dipping, deposition, or painting the polymer solution onto the prosthesis. Usually, the polymer is finely sprayed on the prosthesis while the prosthesis is rotating on a mandrel. A thickness of the matrix coating may be controlled by a time period of spraying and a speed of rotation of the mandrel. The thickness of the matrix coating is typically in a range from 0.01 micron to 100 microns, preferably in a range from 0.1 micron to 10 microns. Once the prosthesis has been coated with the compound/matrix, the stent may be placed in a vacuum or oven to complete evaporation of the solvent.

For example, a stainless steel Duraflex™ stent, having dimensions of 3.0 mm×14 mm is sprayed with a solution of 25 mg/ml the compound in a 100% ethanol, methanol, acetone, ethyl acetate, methylene chloride or other solvent. The stent is dried and the solvent is evaporated leaving the compound on a stent surface. A 75:25 PLLA/PCL copolymer (sold commercially by Polysciences) is prepared in 1,4 Dioxane (sold commercially by Aldrich Chemicals). The compound loaded stent is loaded on a mandrel rotating at 200 rpm and a spray gun (sold commercially by Binks Manufacturing) dispenses the copolymer solution in a fine spray on to the compound loaded stent as it rotates for a 10–30 second period. The stent is then placed in a oven at 25–35° C. up to 24 hours to complete evaporation of the solvent.

Alternatively, in another embodiment, stents bearing a rapalog of this invention may be prepared and used by analogy to the methods of Sousa et al, Circulation, 2001; 103:192; Sousa et al, Circulation, 2001; 104:2007; and Morice et al. N Engl J Med 2002;346(23):1773–1780, but substituting the rapalog for Sirolimus. Thus, patients with native coronary artery disease and angina pectoris may be treated with the implantation of a single rapalog-eluting Bx VELOCITY stent.

In this embodiment, the rapalog is blended in a mixture of nonerodable polymers (see e.g., Kindt-Larsen et al, *J Appl Biomater*. 1995;6:75–83; Revell et al, *Biomaterials*. 1998; 19:1579–1586), and a 5-µm-thick layer of rapalog-polymer matrix is applied onto the surface of the Bx VELOCITY stent (Cordis), a laser-cut 316L stainless-steel balloon-expandable stent. This is referred to as the fast-release [FR] formulation.

The drug will be almost completely eluted by 15 days after implantation in the FR formulation.

To create a slow-release [SR] formulation, another layer of drug-free polymer is applied on top of the drug-polymer matrix to introduce a diffusion barrier and prolong drug release to >28 days. About 80% of the rapalog should be released from the SR formulation within about 30 days.

In this embodiment, the stents, regardless of the coating composition, are loaded with a fixed amount of drug per unit of metal surface area (140 µg drug/cm$^2$).

Based on the experience with other drugs, drug levels in whole blood should peak at 1 hour (~2–3 ng/mL, FR; ~1 ng/mL, SR) after implantation and fall below the lower limit of quantification by about 72 hours. Taking into account that renal transplant patients maintain chronic blood levels of rapamycin between 8 and 17 ng/mL, the peak blood level after implantation of this sort of rapalog-eluting stent should be negligible.

By way of further example, the rapalog-bearing Bx VELOCITY stents are implanted according to standard practice, after balloon predilatation and followed by high-pressure (>12 atmospheres) balloon after dilatation. The stents in this embodiment are 18 mm long and 3 to 3.5 mm in diameter. Heparin may be given to maintain the activated clotting time >300 seconds. Patients may also receive aspirin (325 mg/d, indefinitely) starting at least 12 hours before the procedure and a 300-mg loading dose of clopidogrel immediately after stent implantation and 75 mg/d for 60 days.

In other embodiments, the means for releasing the compound may comprise a reservoir on or within the scaffold holding the compound and an external energy source for directing energy at the prosthesis after implantation to effect release of the compound. A matrix may be formed over the reservoir to contain the compound within the reservoir. Alternatively, the means for releasing the compound may comprise a matrix formed over at least a portion of the scaffold, wherein the compound is disposed under or within the matrix, and an external energy source for directing energy at the prosthesis after implantation to effect release of the compound. Suitable external energy source include ultrasound, magnetic resonance imaging, magnetic field, radio frequency, temperature change, electromagnetic, x-ray, radiation, heat, gamma, and microwave.

For example, an ultrasound external energy source may be used having a frequency in a range from 20 kHz to 100 MHz, preferably in a range from 0.1 MH z to 20 MHz, and an intensity level in a range from 0.05 W/cm 2to 10 W/cm 2, preferably in a range from 0.5 W/cm 2 to 5 W/cm 2. The ultrasound energy should be directed at the prosthesis from a distance in a range from 1 mm to 30 cm, preferably in a range from 1 cm to 20 cm. The ultrasound may be continuously applied or pulsed, for a time period in a range from 5 sec to 30 minutes, preferably in a range from 1 minute to 15 minutes. The temperature of the delivery prosthesis during this period will be in a range from 37° C. to 48° C. The ultrasound may be used to increase a porosity of the prosthesis, thereby allowing release of the compound from the prosthesis.

In one embodiment, means for releasing the compound comprises magnetic particles coupled to the compound and a magnetic source for directing a magnetic field at the prosthesis after implantation to effect release of the compound. Optionally, the means for releasing the compound may comprise magnetic particles coupled to a matrix formed over the device and a magnetic source for directing a magnetic field at the prosthesis after implantation to effect release of the compound. The compound may be disposed under or within the matrix. The magnetic particles may be formed from magnetic beads and will typically have a size in a range from 1 nm to 100 nm. The magnetic source exposes the prosthesis to its magnetic field at an intensity typically in the range from 0.01 T to 2 T, which will activate the magnetic particles, and thereby effect release of the compound from the prosthesis.

This invention thus includes methods for delivering one of the described compounds to an artery. The method is of the type where a prosthesis is implanted in the artery and the prosthesis releases the compound. The method involves implanting a prosthesis that is programmed to begin substantial release of the compound beginning preferably after growth of at least one layer of cells over a part of the prosthesis. The cells will typically comprise inflammation, smooth muscle, or endothelial cells, indicating the onset of restenosis.

A method for positioning the delivery prosthesis in a body lumen in order to deliver the compound therein is also provided. In one approach, a balloon dilation catheter will typically be used to deliver the prosthesis to a region of stenosis in a blood vessel. The prosthesis is initially carried in its radially collapsed diameter configuration on an deflated balloon of the balloon catheter. The balloon catheter is typically introduced over a guidewire under fluoroscopic guidance. The catheters and guidewires may be introduced through conventional access sites to the vascular system, such as through the femoral artery, or brachial, subclavian or radial arteries, for access to the coronary arteries. After the delivery prosthesis is properly positioned within the region of stenosis, the balloon is inflated to radially expand the prosthesis within the stenotic region. The balloon may then be deflated, and the catheter withdrawn over the guidewire. After removal of the guidewire, the expanded prosthesis is left in place to provide luminal delivery of the compound as described above to inhibit restenotic effects.

In general, it will be possible to combine elements of the differing prostheses and treatment methods as described above. For example, a prosthesis having reservoir means for releasing the compound may further incorporate a rate limiting barrier. Additionally, methods of the present invention may combine balloon angioplasty and/or other interventional treatments to resolve a stenotic site with the presently described luminal the compound delivery treatments.

Formulations, Pharmaceutical Compositions, Dosage and Administration

The rapalogs of this invention can exist in free form or, where appropriate, in salt form. Pharmaceutically acceptable salts of many types of compounds and their preparation are well-known to those of skill in the art. Pharmaceutically acceptable salts include conventional non-toxic salts including the quaternary ammonium salts of formed by such compounds with inorganic or organic acids of bases.

The compounds of the invention may form hydrates or solvates. It is known to those of skill in the art that charged compounds form hydrated species when lyophilized with water, or form solvated species when concentrated in a solution with an appropriate organic solvent.

This invention encompasses pharmaceutical compositions comprising a therapeutically (or prophylactically) effective amount of a compound of the invention, and one or more pharmaceutically acceptable carriers and/or other excipients. Carriers include e.g. saline, buffered saline, dextrose, water, glycerol, ethanol, and combinations thereof, and are discussed in greater detail below. The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Formulation may involve mixing, granulating and compressing or dissolving the ingredients as appropriate to the desired preparation. In another approach, the composition may be formulated into nanoparticles.

The pharmaceutical carrier employed may be, for example, either a solid or liquid.

Illustrative solid carriers include lactose, terra alba, sucrose, talc, gelatin, agar, pectin, acacia, magnesium stearate, stearic acid and the like. A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions, and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Illustrative liquid carriers include syrup, peanut oil, olive oil, water, etc. Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant. Liquid pharmaceutical compositions which are sterile solutions or suspensions can be administered by, for example, intravenous, intramuscular, intraperitoneal or subcutaneous injection. Injection may be via a single push or by gradual infusion, e.g. 30 minute intravenous infusion. The compound can also be administered orally either in liquid or solid composition form.

The carrier or excipient may include a time delay material, examples of which are well known to the art, such as glyceryl monostearate or glyceryl distearate, and may further include a wax, ethylcellulose, hydroxypropylmethylcellulose, methylmethacrylate and the like. When formulated for oral administration, 0.01% Tween 80 in PHOSAL PG-50 (phospholipid concentrate with 1,2-propylene glycol, A. Nattermann & Cie. GmbH) has been recognized as providing an acceptable oral formulation for other compounds, and may be adapted to formulations for various compounds of this invention.

A wide variety of pharmaceutical forms can thus be employed in administering compounds of this invention. If a solid carrier is used, the preparation can be tableted, placed in a hard gelatin capsule in powder or pellet form or in the form of a troche or lozenge. The amount of solid carrier will vary widely but preferably will be from about 25 mg to about 1 g. If a liquid carrier is used, the preparation will be in the form of a syrup, emulsion, soft gelatin capsule, sterile injectable solution or suspension in an ampule or vial or nonaqueous liquid suspension.

To obtain a stable water soluble dosage form, the compound, or a pharmaceutically acceptable salt thereof, may be dissolved in an aqueous solution of an organic or inorganic acid, such as a 0.3M solution of succinic acid or citric acid. Alternatively, acidic derivatives can be dissolved in suitable basic solutions. If a soluble form is not available, the compound is dissolved in a suitable cosolvent or combinations thereof. Examples of such suitable cosolvents include, but are not limited to, alcohol, propylene glycol, polyethylene glycol 300, polysorbate 80, glycerin, polyoxyethylated fatty acids, fatty alcohols or glycerin hydroxy fatty acids esters and the like in concentrations ranging from 0–60% of the total volume.

Various delivery systems are known and can be used to administer the compound, or the various formulations thereof, including tablets, capsules, injectable solutions, encapsulation in liposomes, microparticles, microcapsules, etc. Methods of introduction include but are not limited to dermal, intradermal, intramuscular, intraperitoneal, intravenous, subcutaneous, intranasal, pulmonary, epidural, ocular and (as is usually preferred) oral routes. The compound may be administered by any convenient or otherwise appropriate route, for example by infusion or bolus injection, by absorption through epithelial or mucocutaneous linings (e.g., oral mucosa, rectal and intestinal mucosa, etc.) or via a drug-loaded stent and may be administered together with other biologically active agents. Administration can be systemic or local. For treatment or prophylaxis of nasal, bronchial or pulmonary conditions, preferred routes of administration are oral, nasal or via a bronchial aerosol or nebulizer.

In certain embodiments, it may be desirable to administer the compound locally to an area in need of treatment; this may be achieved by, for example, and not by way of limitation, local infusion during surgery, topical application, by injection, by means of a catheter, by means of a suppository, or by means of a skin patch or stent or other implant, said implant typically being of a porous, nonporous, or gelatinous material, including membranes, such as sialastic membranes, or fibers.

In a specific embodiment, the composition is formulated using routine methods as a pharmaceutical composition for intravenous administration to human beings. Typically, compositions for intravenous administration are solutions in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

For example, a solution of a rapalog of this invention for injection may contain 0.1 to 10 mg/ml, e.g. 1–3 mg/ml, of rapalog in a diluant solution containing Phosal 50 PG (phosphatidylcholine, propylene glycol, mono- and di-glycerides, ethanol, soy fatty acids and ascorbyl palmitate) and polysorbate 80, containing 0.5–4% ethanol, e.g. 1.5%–2.5% ethanol. As another example, the diluant may contain 2–8%, e.g. 5–6%, each of propylene glycol USP and polysorbate 80 in water for injection. We have found that 5.2% of each works well in some cases. Typically a solution is processed using conventional methods and materials, including e.g. one or more rounds of sterile filteration.

Oral formulations containing a compound of this invention may comprise any conventionally used oral forms, including tablets, capsules, buccal forms, troches, lozenges and oral liquids, suspensions or solutions. These may take the form of nanoparticles, micro-emulsions or solid dispersions, by way of non-limiting example, which may be prepared by adaptation of conventional materials and methods. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Suitable surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidol silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or a fruit juice, containing appropriate solubilizers or emulsifiers as needed. Oral formulations which may be adapted for use with rapalogs of this invention are disclosed in U.S. Pat. Nos. 5,559,121; 5,536,729; 5,989,591; 5,985,325; 5,145,684 (nanoparticles); U.S. Pat. No. 6,197,781; and WO 98/56358; all of which are hereby incorporated by reference. Tablets containing a rapalog of this invention may contain conventional inactive ingredients including for example sucrose, lactose, polyethylene glycol 8000, calcium sulfate, microcrystalline cellulose, pharmaceutical grade glaze, talc, titanium dioxide, magnesium stearate, povidone, poloxamer 188, polyethylene glycol 20,000, glyceryl monooleate, carnauba wax, and other ingredients. Nanosized compositions for oral administration may also be used. In such cases nanoparticles are formed from compositions containing (on a weight/weight basis) 1–20% rapalog, 70–95% inert material such as sucrose, 0.1 to 4% of materials such as polyvinyl pyrrolidone and benzylconium chloride and 0–1% surfactant such as Tween. An illustrative such composition contains about 15% rapalog, 81% sucrose, 2% polyvinyl pyrrolidone, 2% benzylconium chloride and 0.1% Tween.

In some cases it may be desirable to administer the compounds directly to the airways in the form of an aerosol.

Administration to an individual of an effective amount of the compound can also be accomplished topically by administering the compound(s) directly to the affected area of the skin of the individual. For this purpose, the compound is administered or applied in a composition including a pharmacologically acceptable topical carrier, such as a gel, an ointment, a lotion, or a cream, which includes, without limitation, such carriers as water, glycerol, alcohol, propylene glycol, fatty alcohols, triglycerides, fatty acid esters, or mineral oils.

Other topical carriers include liquid petroleum, isopropyl palmitate, polyethylene glycol, ethanol (95%), polyoxyethylene monolaurate (5%) in water, or sodium lauryl sulfate (5%) in water. Other materials such as anti-oxidants, humectants, viscosity stabilizers, and similar agents may be added as necessary. Percutaneous penetration enhancers such as Azone may also be included.

In addition, in certain instances, it is expected that the compound may be disposed within transdermal devices placed upon, in, or under the skin. Such devices include patches, implants, and injections which release the compound into the skin, by either passive or active release mechanisms. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semi-permeable membrane covering a reservoir containing the active ingredient with or without a carrier, or a matrix containing the active ingredient. Other occlusive devices are known in the literature.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

Materials and methods for producing the various formulations are known in the art and may be adapted for practicing the subject invention. See e.g. U.S. Pat. Nos. 5,182,293 and 4,837,311 (tablets, capsules and other oral formulations as well as intravenous formulations) and European Patent Application Publication Nos. 0 649 659 (published Apr. 26, 1995; illustrative formulation for IV administration) and 0 648 494 (published Apr. 19, 1995; illustrative formulation for oral administration). See also U.S. Pat. No. 5,145,684 (nanoparticles) and U.S. Pat. No. 5,989,591 (solid dosage forms) and WO 98/56358 as well as Yu, K. et al., Endocrine-Related Cancer (2001) 8, 249–258 and Geoerger et al., Cancer Res. (2001) 61 1527–1532.

The effective systemic dose of the compound will typically be in the range of about 0.01 to about 100 mg/kgs, preferably about 0.1 to about 10 mg/kg of mammalian body weight, administered in single or multiple doses. Generally, the compound may be administered to patients in need of such treatment in a daily dose range of about 1 to about 2000 mg per patient. Administration may be once or multiple times daily, weekly (or at some other multiple-day interval) or on an intermittent schedule. For example, the compound may be administered one or more times per day on a weekly basis (e.g. every Monday) for a period of weeks, e.g. 4–10 weeks. Alternatively, it may be administered daily for a period of days (e.g. 2–10 days) followed by a period of days (e.g. 1–30 days) without administration of the compound, with that cycle repeated a given number of times, e.g. 4–10 cycles. As an example, an anti-cancer compound of the invention may be administered daily for 5 days, then discontinued for 9 days, then administered daily for another 5 day period, then discontinued for 9 days, and so on, repeating the cycle a total of 4–10 times.

The amount of compound which will be effective in the treatment or prevention of a particular disorder or condition will depend in part on well known factors affecting drug dosage, and in the case of gene and cell therapy applications, will also depend on the characteristics of the fusion proteins to be multimerized, the characteristics and location of the genetically engineered cells, and on the nature of the disorder or condition, which can be determined by standard clinical techniques. In addition, in vitro or in vivo assays may optionally be employed to help identify optimal dosage ranges. Effective doses may be extrapolated from dose-response curves derived from in vitro or animal model test systems. The precise dosage level should be determined by the attending physician or other health care provider and will depend upon well known factors, including route of administration, and the age, body weight, sex and general health of the individual; the nature, severity and clinical stage of the disease; the use (or not) of concomitant therapies; and the nature and extent of genetic engineering of cells in the patient.

When administered for the treatment or inhibition of a particular disease state or disorder, the effective dosage of the rapalog of this invention may vary depending upon the particular compound utilized, the mode of administration, the condition, and severity thereof, of the condition being treated, as well as the various physical factors related to the individual being treated. In many cases, satisfactory results may be obtained when the rapalog is administered in a daily dosage of from about 0.01 mg/kg–100 mg/kg, preferably between 0.01–25 mg/kg, and more preferably between 0.01–5 mg/kg. The projected daily dosages are expected to vary with route of administration. Thus, parenteral dosing will often be at levels of roughly 10% to 20% of oral dosing levels.

When the rapalog is used as part of a combination regimen, dosages of each of the components of the combination are administered during a desired treatment period. The components of the combination may administered at the same time; either as a unitary dosage form containing both components, or as separate dosage units; the components of the combination can also be administered at different times during a treatment period, or one may be administered as a pretreatment for the other.

The invention also provides a pharmaceutical pack or kit comprising one or more containers containing one or more of the ingredients of the pharmaceutical compositions of the invention. Optionally associated with such container(s) can be a notice in the form prescribed by a governmental agency regulating the manufacture, use or sale of pharmaceutical or biological products, which notice reflects approval by the agency of manufacture, use or sale for human administration. The notice or package insert may contain instructions for use of a rapalog of this invention, consistent with the disclosure herein.

The following examples contain important additional information, exemplification and guidance which can be adapted to the practice of this invention in its various embodiments and the equivalents thereof. The examples are offered by way illustration should not be construed as limiting in any way. Numerous modifications and variations of the present invention should be apparent to one of skill in the art. Such modifications and variations, including design choices in selecting, preparing, formulating and administering the rapalog of this invention; the choice of stent design, materials and methods and materials for loading the rapalog thereon and for delivery the drug-eluting stent;, etc. are intended to be encompassed by the scope of the invention and of the appended claims.

The contents of all cited references including literature references, issued patents, and published patent applications as cited throughout this document are hereby expressly incorporated by reference. The practice of the present invention will employ, unless otherwise indicated, conventional techniques of synthetic organic chemistry, including product recovery, purification and formulation, as well as of cell biology, cell culture, molecular biology, transgenic biology, microbiology, recombinant DNA, and immunology, which are within the skill of the art. Such techniques are explained fully in the patent and scientific literature. See, for example, in the case of biological techniques: Molecular CloningÜA LaboratoryÜManual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No: 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I–IV (D. M. Weir and C. C. Blackwell, eds., 1986); Manipulating the Mouse Embryo, (Cold Spring Harbor Laboratory Press, Cold Spring Harbor, N.Y., 1986).

EXAMPLES

Example 1

Methyl-phosphonic Acid Ethyl Ester C-43 Rapamycin Ester

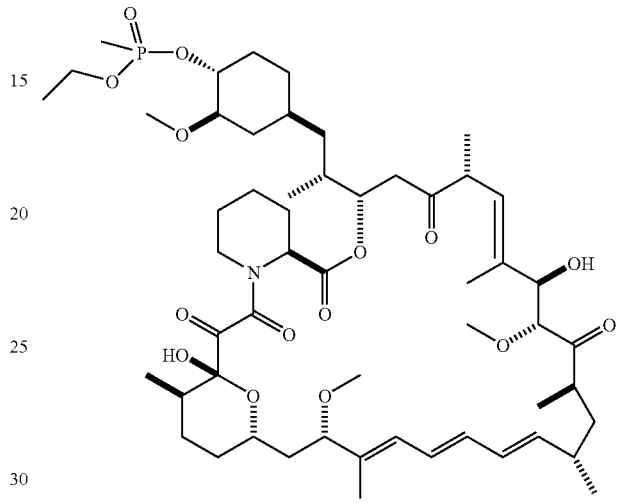

Ethyl Methylphosphonochloridate

To a cooled (0° C.) solution of diethyl methylphosphonate (15.2 g, 0.1 mol) in benzene (30 mL) was added $PCl_5$ (20.8 g, 0.1 mol) in one portion. After the reaction mixture was stirred at 0° C. for 2 hours, the solvent and byproduct $POCl_3$ was removed under high vaccum. The product was distilled to give 12.7 g of a colorless oil: Bpt. 52–54° C./1 mmHg; $^{31}$P-NMR (121 MHz, $CDCl_3$) d 40.7.

Methyl-phosphonic Acid Eethyl Ester C-43 Rapamycin Ester

To a cooled (0° C.) solution of rapamycin (0.1 g, 0.109 mmol) in 1.5 mL of dichloromethane was added a solution of 3,5-lutidine (0.088 g, 0.82 mmol) in 0.25 mL of dichloromethane, under an atmosphere of $N_2$, followed immediately by a solution of ethyl methylphosphonochloridate (0.078 g, 0.547 mmol) in 0.25 mL of dichloromethane. The colorless reaction solution was stirred at 0° C. for 3 h (reaction monitored by MS; reaction sample diluted directly with 50:50 $CH_3CN/H_2O$, 1 drop DMSO, prior to analysis). The cold (0° C.) reaction solution was diluted with ~20 mL EtOAc then transferred to a separatory funnel containing EtOAc (150 mL) and saturated $NaHCO_3$ (100 mL). Upon removing the aqueous layer, the organic layer was washed successively with ice cold 1N HCl (1×100 mL), saturated $NaHCO_3$ (1×100 mL), and brine (1×100 mL), then dried over $MgSO_4$ and concentrated. The crude product was purified by silica gel flash chromatography (eluted with 0.5:10:3:3 MeOH/DCM/EtOAc/hexane) to provide 0.024 g of a white solid (~2:1 diastereomeric mixture): $^1$H NMR (300 MHz, $CDCl_3$) d 4.19 (m, 1Ha, 1Hb), 4.15–4.01 (m, 3Ha, 3Hb), 1.56–1.27 (m, 6Ha, 6Ha, 6Hb); $^{31}$P NMR (121 MHz, $CDCl_3$) d 32.1, 29.9; 1043 m/z (M+Na).

Example 1

Alternative Synthesis:

Rapamycin and dichloromethane are charged into a nitrogen-purged reaction flask. The stirred solution is cooled to approximately 0° C. (an external temperature of −5±5° C. is maintained throughout the reaction). A solution of ethyl methylphosphonochloridate in dichloromethane is then added over a period of approximately 8–13 minutes. This is followed immediately by the addition of a solution of 3,5-lutidine in dichloromethane over a period of approximately 15–20 minutes. Throughout both additions, the internal temperature of the reaction is maintained below 0° C. The cooled reaction solution is stirred for 3 hours during which time reaction progress is monitored by TLC (1:10:3:3 MeOH/DCM/EtOAc/hexanes) and reverse-phase HPLC analyses. In due course, the reaction mixture is diluted with ethyl acetate and worked up as above.

Example 2

Methyl-phosphonic Acid n-butyl Ester C-43 Rapamycin Ester

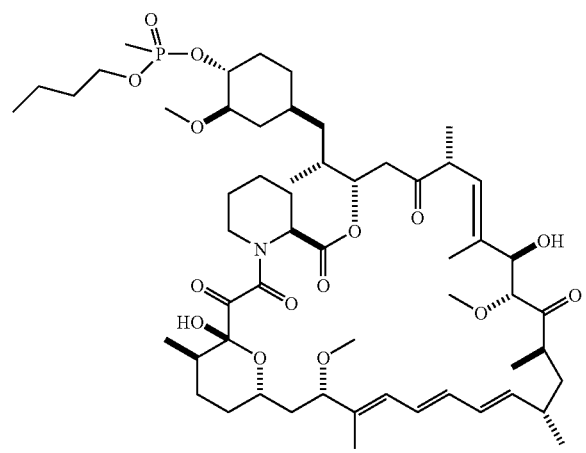

To a flask containing 1H-tetrazole (~0.002 g, 0.028 mmol) was added a solution of n-butanol (0.041 g, 0.55 mmol) in 0.33 mL of DCM, followed by a solution of 3,5-lutidine (0.090 g, 0.84 mmol) in 0.33 mL of DCM. The resulting clear solution was cooled to 0° C. then added, under an atmosphere of $N_2$, a solution of methylphosphonic dichloride (0.073 g, 0.55 mmol) in 0.33 mL of DCM. The resulting white suspension was stirred to ambient temperature overnight. To a cooled (0° C.) solution of rapamycin (0.1 g, 0.11 mmol) in 0.5 mL of DCM was added a solution of 3,5-lutidine (0.090 g, 0.84 mmol) in 0.5 mL of DCM, followed immediately by the phosphorylating reagent (yellow solution with white precipitate) and a 1.0 mL DCM wash. The resulting yellow solution was stirred at 0° C. for 1.0 h (followed by MS). The cold (0° C.) reaction solution was diluted with ~20 mL EtOAc then transferred to a separatory funnel containing EtOAc (120 mL) and saturated $NaHCO_3$ (100 mL). Upon removing the aqueous layer, the organic layer was washed successively with ice cold 1N HCl (1×100 mL), saturated $NaHCO_3$ (3×100 mL), and brine (1×100 mL), then dried over $MgSO_4$ and concentrated. The crude product was purified by silica gel flash chromatography (eluted with 0.25:10:3:3 then 0.5:10:3:3 MeOH/DCM/EtOAc/hexane) then RP HPLC (85% $MeOH/H_2O$) to provide 0.063 g of a white solid (~2:1 diastereomeric mixture): $^1H$ NMR (300 MHz, $CDCl_3$) d 4.15 (m, 1Ha, 1Hb), 4.11–3.89 (m, 3Ha, 3Hb), 3.04 (m, 1Ha, 1Hb); $^{31}P$ NMR (121 MHz, $CDCl_3$) d 32.1, 29.9; 1071 m/z (M+Na).

Example 3

Methyl-phosphonic Acid 2-methoxy-ethyl Ester C-43 Rapamycin Ester

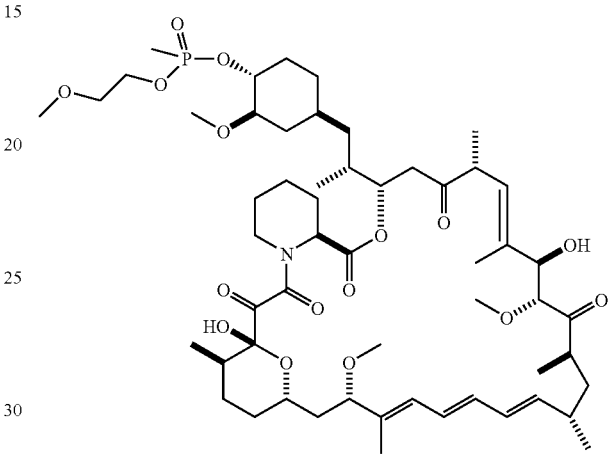

The title compound was synthesized in a manner similar to that described for Example 2. The product was obtained as a white solid (~2:1 diastereomeric mixture): $^{31}P$ NMR (121 MHz, $CDCl_3$) d 33.0, 30.8; 1073 m/z (M+Na).

Example 4

Methyl-phosphonic Acid 2-ethoxy-ethyl Ester C-43 Rapamycin Ester

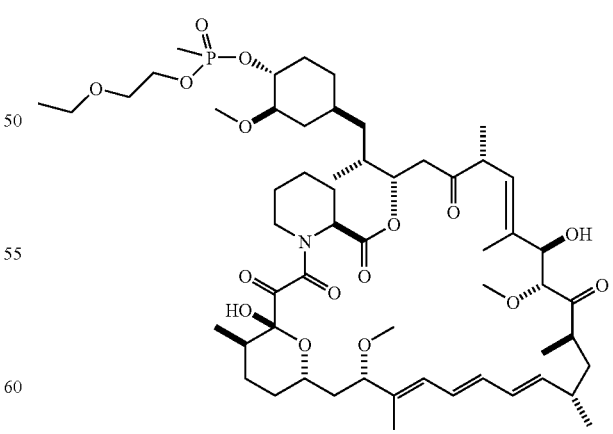

The title compound was synthesized in a manner similar to that described for Example 2. The product was obtained as a white solid (~2:1 diastereomeric mixture): $^{31}P$ NMR (121 MHz, $CDCl_3$) d 32.8, 30.8; 1087 m/z (M+Na).

Example 5

Methyl-phosphonic Acid n-propyl Ester C-43 Rapamycin Ester

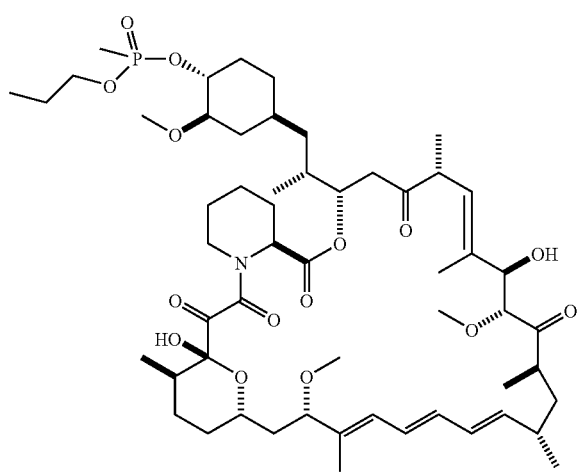

The title compound was synthesized in a manner similar to that described for Example 2. The product was obtained as a white solid (~2:1 diastereomeric mixture): 31P NMR (121 MHz, CDCl$_3$) d 32.1, 29.9; 1057 m/z (M+Na).

Example 6

Methyl-phosphonic Acid Isopropyl Ester C-43 Rapamycin Ester

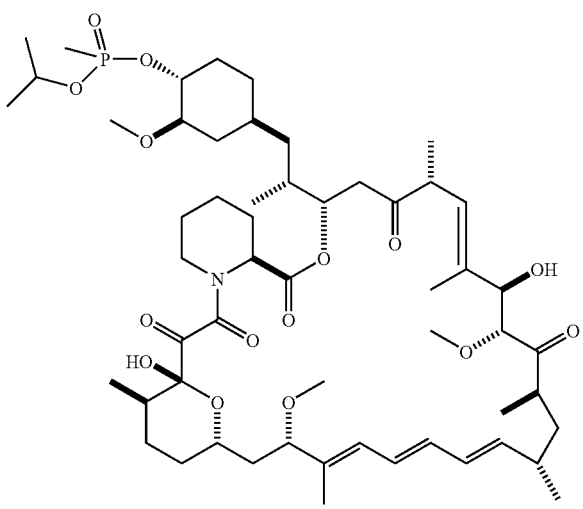

The title compound was synthesized in a manner similar to that described for Example 2. The product was obtained as a white solid (~2:1 diastereomeric mixture): $^{31}$P NMR (121 MHz, CDCl$_3$) d 31.3, 28.8; 1057 m/z (M+Na).

Example 7

Methyl-phosphonic acid 2-(2-hydroxy-ethoxy)-ethyl ester C-43 rapamycin ester

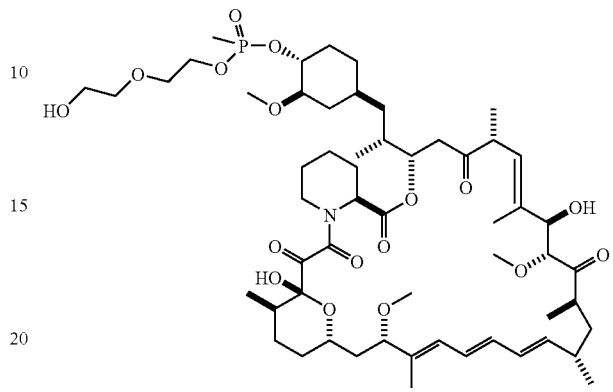

The title compound was synthesized in a manner similar to that described for Example 2. The product was obtained as a white solid (~2:1 diastereomeric mixture): $^{31}$P NMR (121 MHz, CDCl$_3$) d 32.7, 30.9; 1103 m/z (M+Na).

Example 8

Diamino-phosphinic Acid C-43 Rapamycin Ester

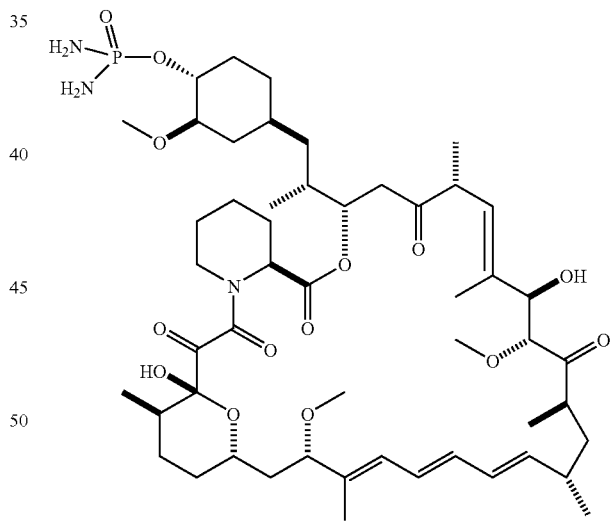

Diamino-phosphinic Acid C-43 Rapamycin Ester

To a stirring solution (0° C.) of rapamycin (0.109 g, 0.12 mmol) and 4-dimethylaminopyridine (0.072 g, 0.59 mmol) in 5.0 mL of DCM was added, dropwise, phosphorous oxychloride (0.050 mL, 0.54 mmol). After a period of 15 min., the mixture was diluted with an additional 5.0 mL of DCM and cooled to −78° C. Ammonia was then bubbled through the reaction mixture for a period of two minutes producing a thick white precipitate. The reaction mixture was then partitioned between a biphasic mixture of 75 mL of EtOAc and 25 mL of 5% aq. HCl. The organic portion was washed sequentially with 25 mL of water and 25 mL of brine, dried over MgSO$_4$, and concentrated. The resulting residue was purified by silica gel flash chromatography (eluted with 9:1 dichloromethane/methanol) which yielded 0.029 g of the desired product: $^{31}$P NMR (121 MHz, CDCl$_3$) 16.4; 1014 m/z (M+Na).

Example 9

Dimethyl-phosphinic Acid C-43 Rapamycin Ester

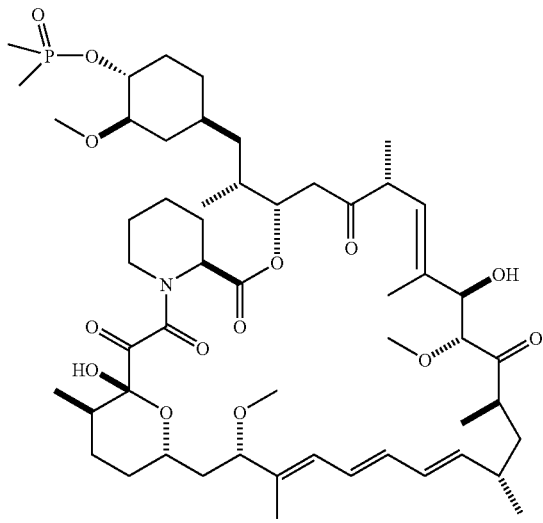

Dimethyl-phosphinic Acid C-43 Rapamycin Ester

To a cooled (0° C.) solution of rapamycin (0.1 g, 0.109 mmol) in 1.8 mL of dichloromethane was added 0.168 g (0.82 mmol) of 2,6-di-t-butyl-4-methyl pyridine, under a stream of N$_2$, followed immediately by a solution of dimethylphosphinic chloride (0.062 g, 0.547 mmol) in 0.2 mL of dichloromethane. The slightly yellow reaction solution was stirred at 0° C., under an atmosphere of N$_2$, for 3.5 h (reaction monitored by TLC). The cold (0° C.) reaction solution was diluted with ~20 mL EtOAc then transferred to a separatory funnel containing EtOAc (150 mL) and saturated NaHCO$_3$ (100 mL). Upon removing the aqueous layer, the organic layer was washed successively with ice cold 1N HCl (1×100 mL), saturated NaHCO$_3$ (1×100 mL), and brine (1×100 mL), then dried over MgSO$_4$ and concentrated. The crude product was purified by silica gel flash chromatography (eluted with 1:10:3:3 MeOH/DCM/EtOAc/hexane) to provide 0.092 g of a white solid: $^1$H NMR (300 MHz, CDCl$_3$) d 4.18 (m, 1H), 4.10 (m, 1H), 3.05 (m, 1H), 1.51 (m, 6H); $^{31}$P NMR (121 MHz, CDCl$_3$) d 53.6; 1013 m/z (M+Na).

Example 9

Alternative Synthesis

Rapamycin and dichloromethane are charged into a nitrogen-purged reaction flask. The stirred solution is cooled to approximately 0° C. (an external temperature of −5±5° C. is maintained throughout the reaction). A solution of dimethylphosphinic chloride (2.0 molar equivalents) in dichloromethane is then added over a period of approximately 8–13 minutes. This is followed immediately by the addition of a solution of 3,5-lutidine (2.2 molar equivalents) in dichloromethane over a period of approximately 15–20 minutes. Throughout both additions, the internal temperature of the reaction sssstays below 0° C. The cooled reaction solution is stirred for 1 hour and then transferred, while still cold, to an extractor containing saturated aqueous NaHCO$_3$ and methyl-t-butyl ether (MTBE), ethyl acetate or diethyl ether. In-process samples are removed at 30 and 60 minute time points. Samples are prepared in a similar fashion to that described for the reaction workup. Reaction progress is monitored by TLC (1:10:3:3 MeOH/DCM/EtOAc/hexanes) and reverse-phase HPLC analyses. The isolated organic layer is successively washed with ice cold 1N HCl, saturated aqueous NaHCO$_3$ (2×), saturated aqueous NaCl, and dried over sodium sulfate. Upon filtration and solvent removal, the residue undergoes solvent exchange with acetone followed by concentration in vacuo to provide crude product, which may be analyzed for purity by normal- and reversed-phase HPLC.

Example 10

Phosphoric Acid Diethyl Ester C-43 Rapamycin Ester

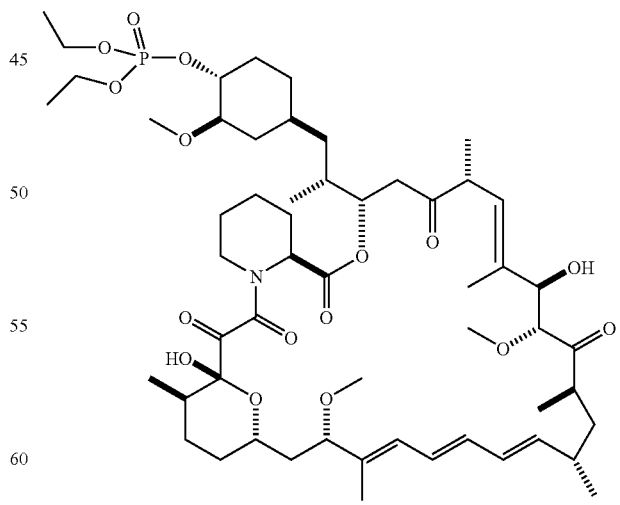

The title compound was synthesized in a manner similar to that described for Example 9. The product was obtained as a white solid: $^{31}$P NMR (121 MHz, CDCl$_3$) d −1.2; 1073 m/z (M+Na).

Example 11

Diphenyl-phosphinic Acid C-43 Rapamycin Ester

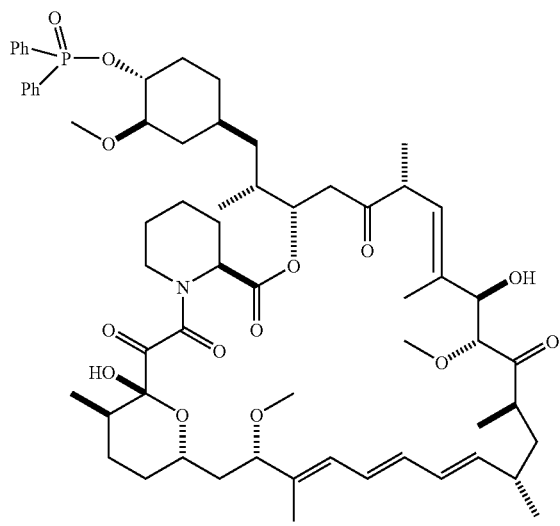

The title compound was synthesized in a manner similar to that described for Example 9. The product was obtained as a white solid: $^{31}$P NMR (121 MHz, CDCl$_3$) d 31.3; 1137 m/z (M+Na).

Example 12

Diethyl-phosphinic Acid C-43 Rapamycin Ester

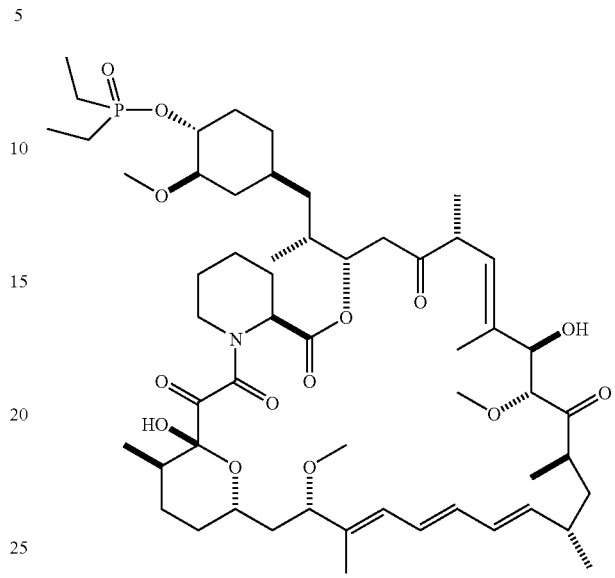

The title compound was synthesized in a manner similar to that described for Example 9. The product was obtained as a white solid: $^{31}$P NMR (121 MHz, CDCl$_3$) d 61.3; 1041 m/z (M+Na).

Example 13

Preparation of Phosphorus-containing epi C-43 Rapamycin Ester Derivatives

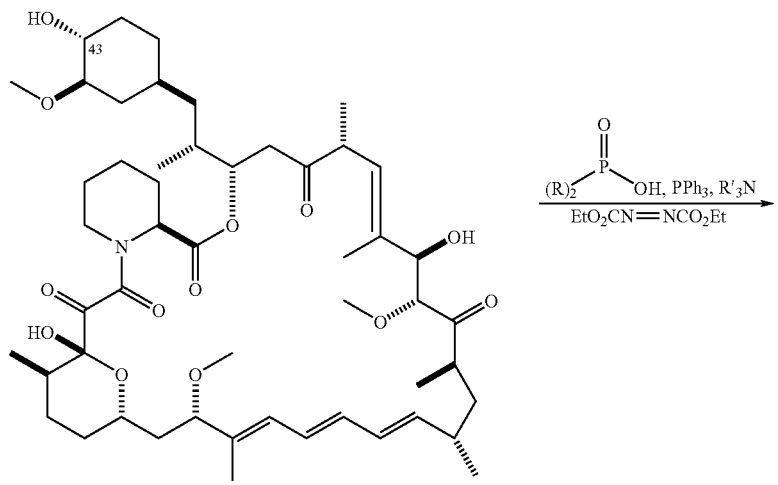

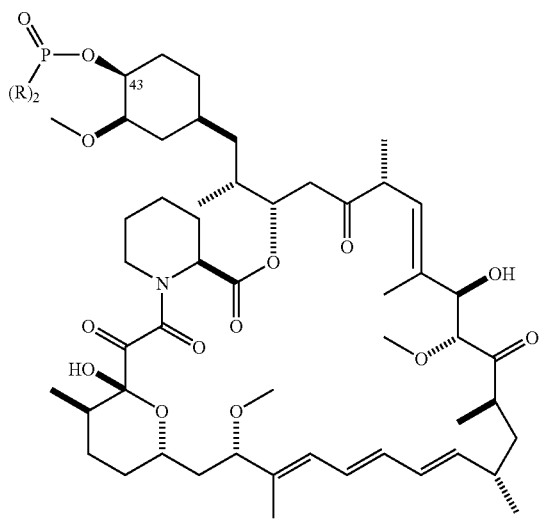

43-epi compounds of the sort shown above may be prepared by adaptation of the methods of Kay, P. B. et al, *J Chem Soc, Perkin Trans.* 1, 1987, [8], 1813–1815, using the depicted reagents where R and each R' is a substituted or unsubstituted aliphatic, aliphatic-O—, aryl, aryloxy, heteroaryl, heteroaryloxy, etc. moiety.

Example 14

Preparation of Phosphorus-linked C-43 Rapamycin Derivatives

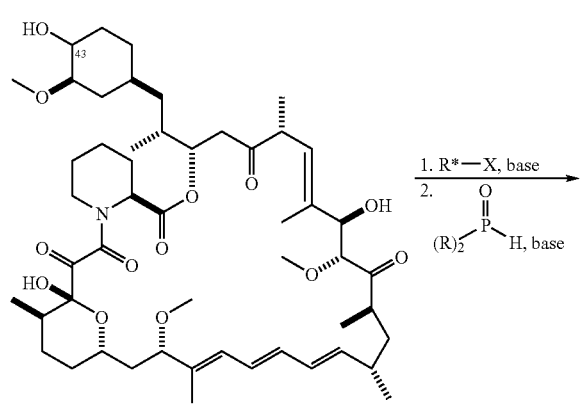

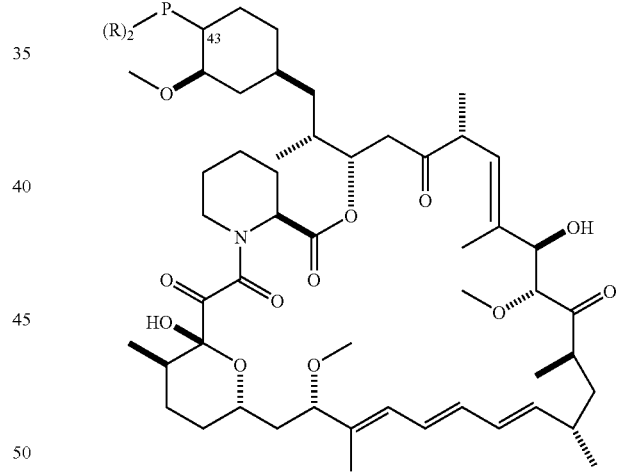

Phosphorous-linked compounds of the sort shown above may be prepared by adaptation of the methods of Yamashita, M. et al, *Bull Chem Soc Japan*, 1983, 56, 1871–1872 using the depicted reagents where X is halogen or anhydride for example, R*X generates a C-43 R*O-moiety which acts as a leaving group, and each occurrence of R is a substituted or unsubstituted aliphatic, aliphatic-O—, aryl, aryloxy, heteroaryl, heteroaryloxy, etc. moiety.

Example 15

Preparation of Phosphorus-containing C-43 Rapamycin Alkyl Amine-linked Derivatives

Example 16

Preparation of Phosphorus-containing C-43 Rapamycin Ether-linked Derivatives

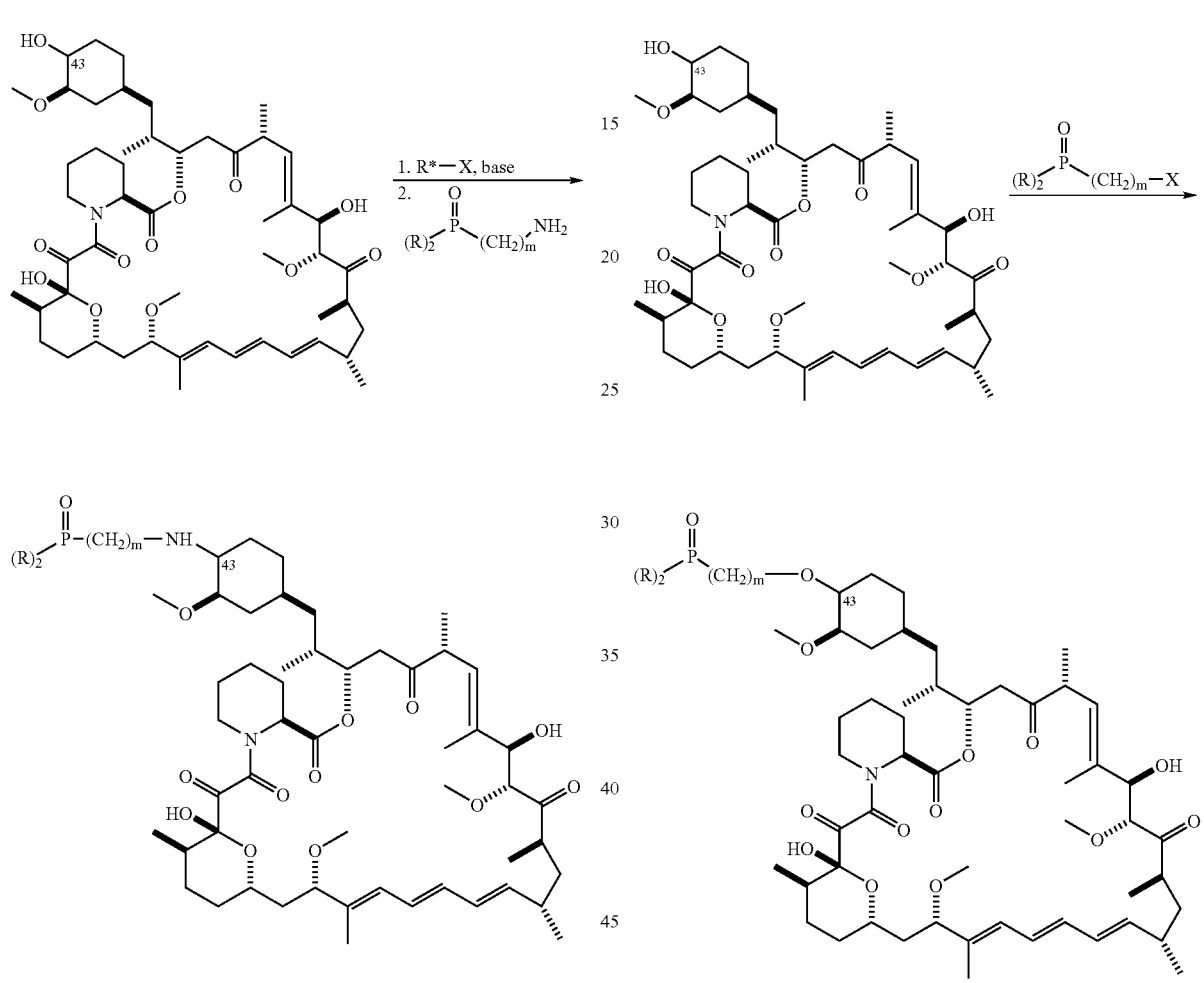

Amine-linked compounds of the sort shown above may be prepared by adaptation of the methods of Cavalla, D. et. al. Tet. Lett., 1983, 24, 295–298; Grinfield, A. et al, WO 98/09972 and Or, Y. S. et al U.S. Pat. No. 5,583,139 using the depicted reagents where X is halogen or anhydride for example, R*X generates a C-43 R*O-moiety which acts as a leaving group, m is a number from 1 to 10, and each occurrence of R is a substituted or unsubstituted aliphatic, aliphatic-O—, aryl, aryloxy, heteroaryl, heteroaryloxy, etc. moiety.

Ethers of the sort shown above may be prepared by adaptation of the methods of Cottens, S et al, PCT International. Appln. Publication No. WO 94/09010 and Cheng, D. et al, WO 98/09970 using the depicted reagent (and base) where X is a leaving group, m is a number from 1 to 10, and each occurrence of R is a substituted or unsubstituted aliphatic, aliphatic-O—, aryl, aryloxy, heteroaryl, heteroaryloxy, etc. moiety.

Example 17
Preparation of Phosphorus-containing C-43 Rapamycin Alkyl Thio-linked Derivatives
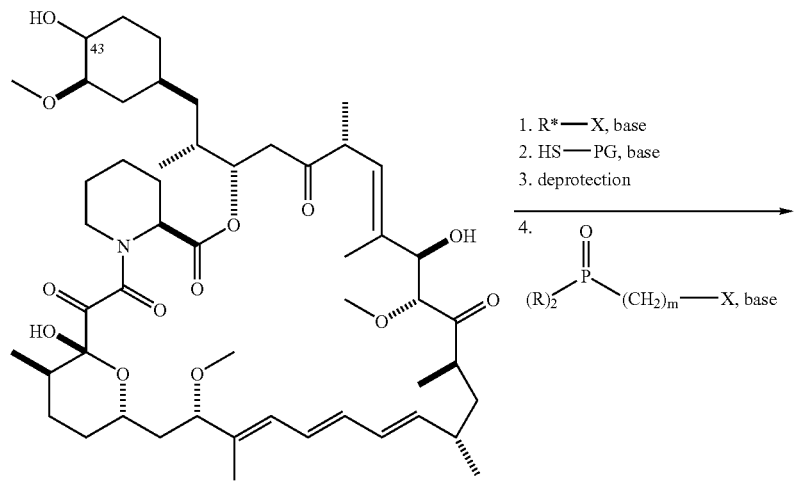
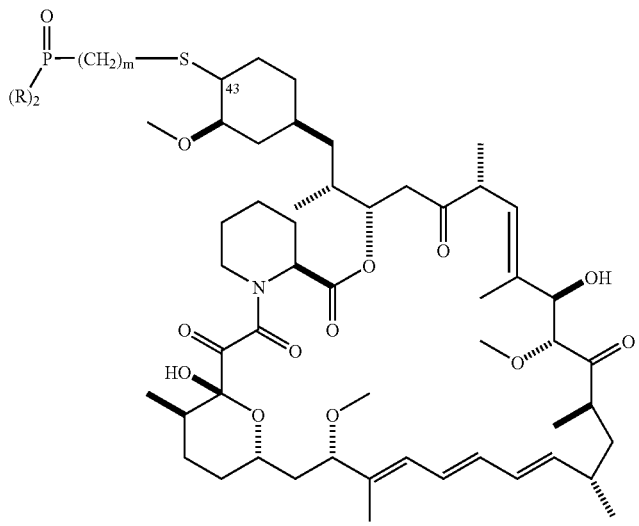

Thio-ethers of the sort shown above may be prepared by adaptation of the methods of Grinfield et al, PCT International. Appln. Publication No. WO 98/09972 using the depicted reagent reagents where X is halogen or anhydride for example, R*X generates a C-43 R*O-moiety which acts as a leaving group, m is a number from 1 to 10, PG is a thiol protecting group, and each occurrence of R is a substituted or unsubstituted aliphatic, aliphatic-O—, aryl, aryloxy, heteroaryl, heteroaryloxy, etc. moiety.

Example 18

Preparation of Additional Phosphorus-containinq C-43 Rapamycin Thio-linked Derivatives

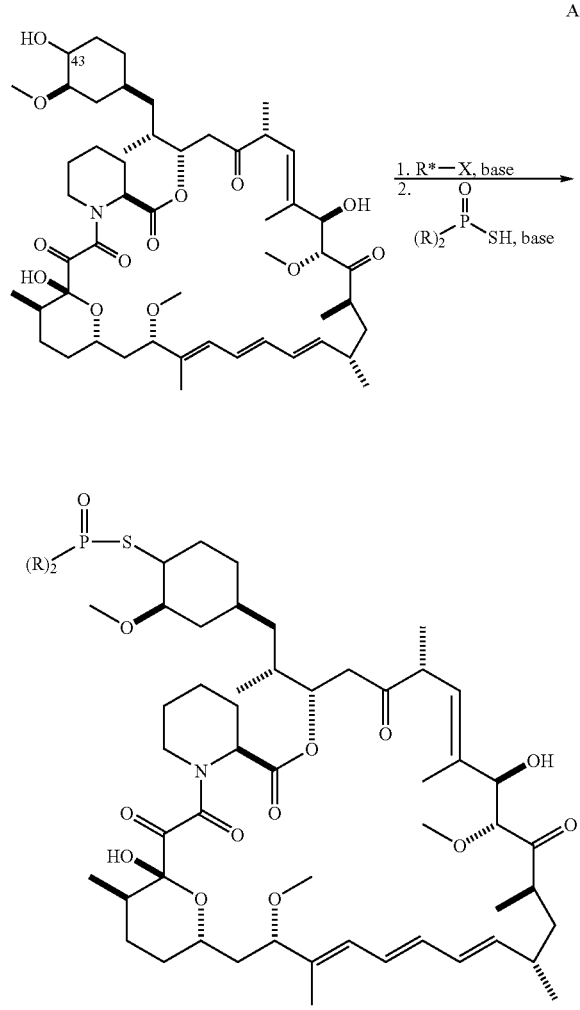

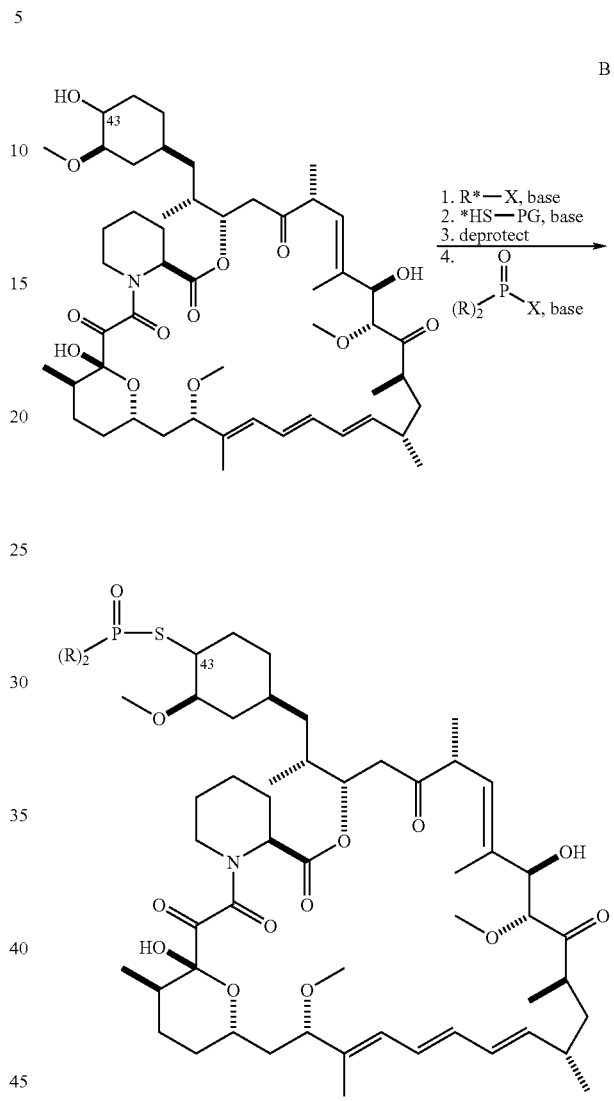

Thio-compounds of the sort shown above may be prepared by adaptation of the methods of Yuan et al, *Synthesis*, 1989, 1, 48–50 (Route A) or Grinfield et al, PCT International. Appln. Publication No. WO 98/09972 and Masson S et al, *Bull Soc Chim Fr*, 1996, 133, 951–964 (Route B) using the depicted reagent reagents where X is halogen or anhydride for example, R*X generates a C-43 R*O-moiety which acts as a leaving group, m is a number from 1 to 10, and each occurrence of R is a substituted or unsubstituted aliphatic, aliphatic-O—, aryl, aryloxy, heteroaryl, heteroaryloxy, etc. moiety.

Example 19
Preparation of Phosphorus-containing C-43 Rapamycin Amino-linked Derivatives
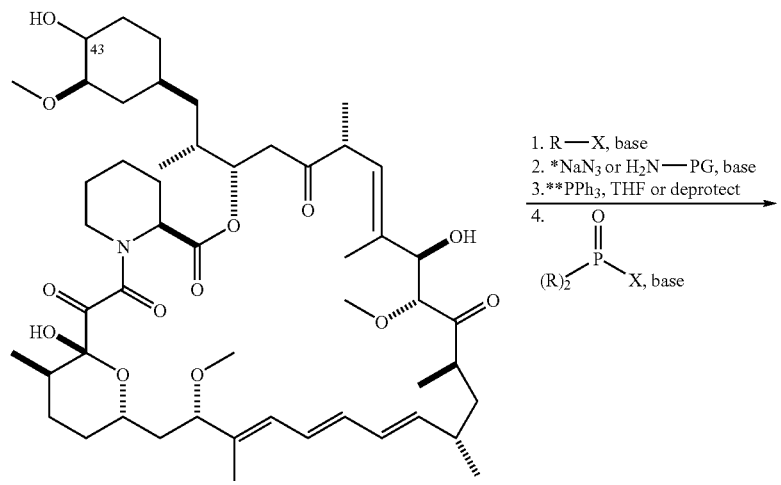
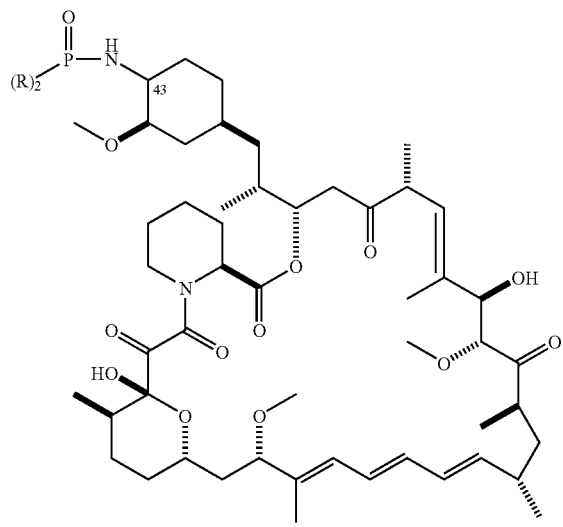

Compounds of the sort shown above may be prepared by adaptation of the methods of Grinfield et al, PCT International. Appln. Publication No. WO 98/09972; Bravo, F et al, *Tetrahedron: Assymetry*, 2001, 12, 1635–1643; and Wang M, et al, *J Org Chem*, 1995, 60, 7364–7365 using the depicted reagents, where X is halogen or anhydride for example, R*X generates a C-43 R*O-moiety which acts as a leaving group, m is a number from 1 to 10, PG is a protecting group and each occurrence of R is a substituted or unsubstituted aliphatic, aliphatic-O—, aryl, aryloxy, heteroaryl, heteroaryloxy, etc. moiety.

Example 20

Preparation of Phosphorus-containing C43 Rapamycin Mixed Ester Derivatives

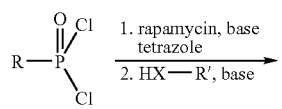

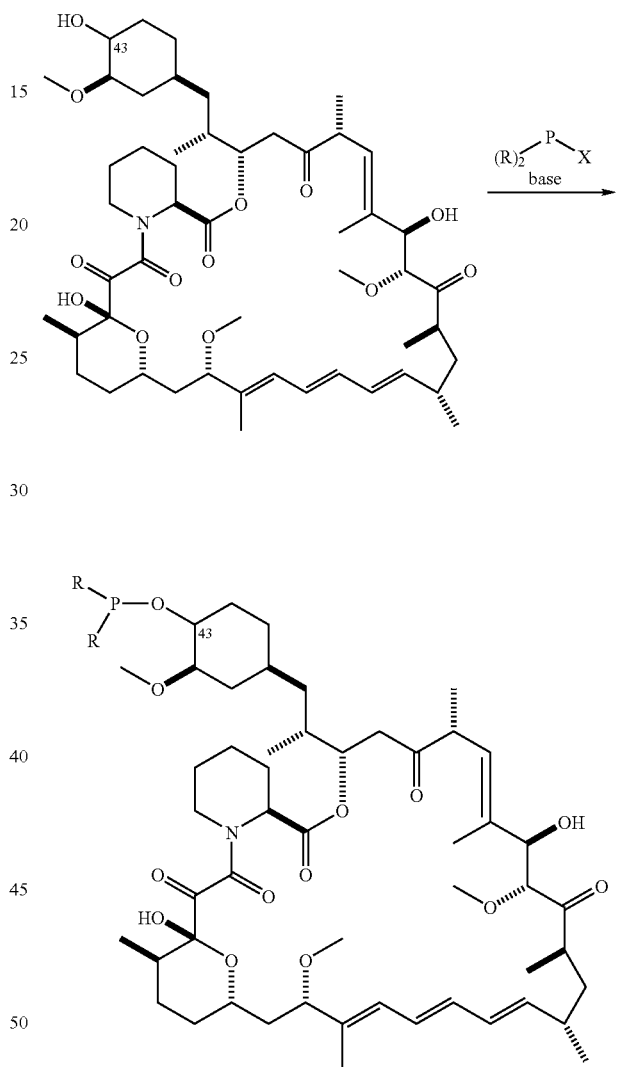

Compounds of the sort shown above may be prepared by adaptation of the methods of Zhao, K. et al, *Tetrahedron*, 1993, 49, 363–368 using the depicted reagents, where X is a NH, O or S and each occurrence of R and R' is a substituted or unsubstituted aliphatic, heteroaliphatic, aryl, or heteroaryl moiety (or if X is NH, R' may be H).

Example 21

Additional O—P-linked Compounds

Compounds of the sort shown above may be prepared by adaptation of the methods of McCallum, J. S. et al. *Synthesis*, 1993, 8, 819–823, and Nifantyev, E. E. et al. *J. Organomet. Chem.*, 1997, 529, 171–176 using the depicted reagents, where X is a leaving group.

Example 22

Additional Compounds

Preparation of Phosphorus-containing C-43 Rapamycin Ether-linked Derivatives (see Examples 1, 2, 3, 5, 11, 17–20 for Coupling Conditiond and R Group Designations)

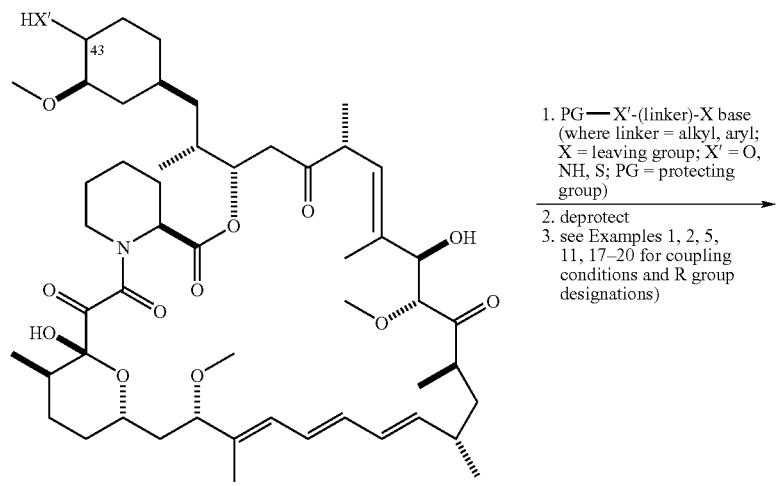

1. PG—X'-(linker)-X base
   (where linker = alkyl, aryl;
   X = leaving group; X' = O,
   NH, S; PG = protecting
   group)
2. deprotect
3. see Examples 1, 2, 5,
   11, 17–20 for coupling
   conditions and R group
   designations)

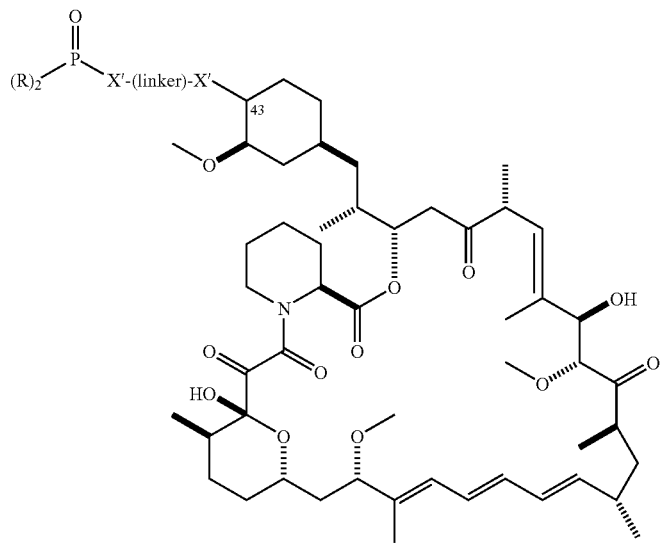

(Cottens, S. et. al. PCT Int. Appl. [1994] WO 94/09010 and Cheng, D. et. al. PCT Int. Appl. [1998] WO 98/09970)

Example 23

Preparation of Phosphorus-linked C-43 Rapamycin PEG Esters

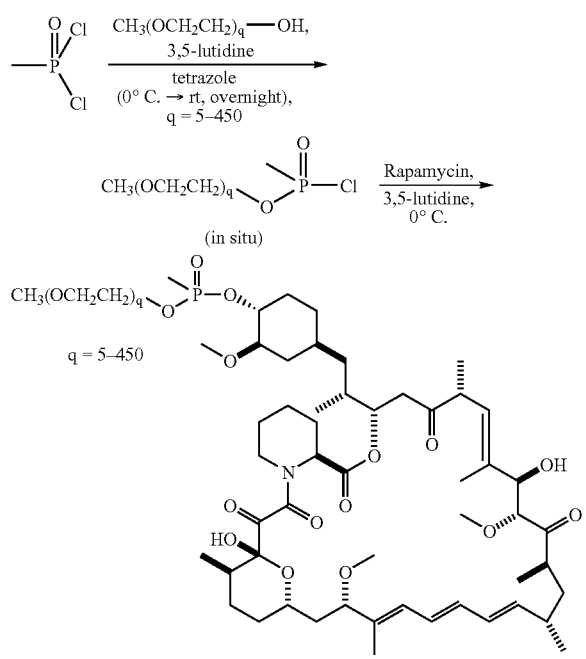

Example 24

Purification

The compounds of the foregoing illustrative Examples may be purified using silica gel flash chromatography to remove possible impurities such as residual reactants (including residual rapamycin or rapalog starting material) and undesired byproducts. Suitable flash chromatography systems include commercially available prepacked cartridge systems, such as those of BIOTAGE, Inc. (PO Box 8006), Charlottesville, Va. 22906-8006). Cartridges may be obtained containing ~30–70 µM particle size, 60 Å pore size silica. A typical protocol is provided below for using such flash chromatography systems for purifying compounds of this invention Crude product is dissolved in a minimum amount of an appropriate solvent (e.g. dichloromethane, "DCM") and loaded onto a FLASH Biotage cartridge. Nonpolar impurities are eluted with DCM, followed by elution of the product with a solvent system such as 0.5:10:3:3 MeOH/DCM/EtOAc/hexanes. A final wash of the column is performed, e.g., with a 1:10:3:3 MeOH/DCM/EtOAc/hexanes solvent system. The collected fractions may be analyzed by TLC, normal-, and reverse-phase HPLC. Pure product fractions from the two or more elution runs are identified by normal phase HPLC then combined and concentrated in vacuo. To improve overall yield of purified product, impure fractions may be repurified on a separate FLASH Biotage system using the same elution solvents and purity criteria for combination. The multiple purified product pools are individually subjected to multiple solvent exchanges, e.g., with acetone (typically 4 to 6 times) and then combined using the same solvent (e.g., acetone) as the transfer solvent. Prior to combining, the pools may be assayed to confirm acceptable purity. Additional solvent exchanges (typically 2) may be performed with the same solvent (acetone, in this example) on the combined product batch, which is then dried in vacuo to constant weight at ambient temperature to provide material that may be sampled if desired for QC analysis.

Example 25

Compound Loaded on Vascular Stent

A stainless steel Duraflex.™. stent, having dimensions of 3.0 mm×14 mm is sprayed with a solution of 25 mg/ml a compound of any of Examples 1–12 in a 100% ethanol, acetone or ethyl acetate solvent. The stent is dried and the solvent is evaporated leaving the compound on a stent surface. A 75:25 PLLA/PCL copolymer (sold commercially by Polysciences) is prepared in 1,4 Dioxane (sold commercially by Aldrich Chemicals). The compound-loaded stent is loaded on a mandrel rotating at 200 rpm and a spray gun (sold commercially by Binks Manufacturing) dispenses the copolymer solution in a fine spray on to the compound-loaded stent as it rotates for a 10–30 second period. The stent is then placed in a oven at 25–35° C. up to 24 hours to complete evaporation of the solvent.

Example 26

Increased Loading of Compound on Vascular Stent

Stainless steel Duraflex stent (3.0×13 mm) is laser cut from a SS tube. The surface area for loading the drug is increased by increasing the surface roughness of the stent. The surface area and the volume of the stent can be further increased by creating 10 nm wide and 5 nm deep grooves along the links of the stent strut. The grooves are created in areas which experience low stress during expansion so that the stent radial strength is not compromised. A compound of any of Examples 1–12 can then be loaded on the stent and in the groove by dipping or spraying the stent in a solution of the compound prepared in low surface tension solvent such as dichloromethane, isopropyl alcohol, acetone, ethyl acetate, ethanol, or methanol. The stent is then dried and the compound resides on the stent surface and in the grooves, which serve as a drug reservoir. Parylene is then deposited on the stent to serve as a rate limiting barrier. The compound elutes from the stent over a period of time in the range from 1 day to 45 days.

Example 27

A compound of any of Examples 1–12 is dissolved in ethyl acetate, then sprayed on the stent, and left to dry evaporating the solvent with the compound remaining on the stent surface. A matrix or barrier (silicone, polytetrafluoroethylene, PARYLAST™, parylene) is sprayed or deposited on the stent encapsulating the compound. The amount of the compound varies from 100 micrograms to 2 milligrams, with release rates from 1 day to 45 days.

Example 28

A matrix with compound coated on a stent, is prepared as described in Example 25, and then coated or sprayed with a top coat of a rate limiting barrier (and/or a matrix without a drug so to act as a rate limiting barrier). Alternatively, the compound may be coated on a stent via a rate limiting barrier, and then covered with a top coat (another barrier or matrix). Use of top coats provide further control of release rate, improved biocompatibility, and/or resistance to scratching and cracking upon stent delivery or expansion.

The invention claimed is:

1. A compound of the formula:

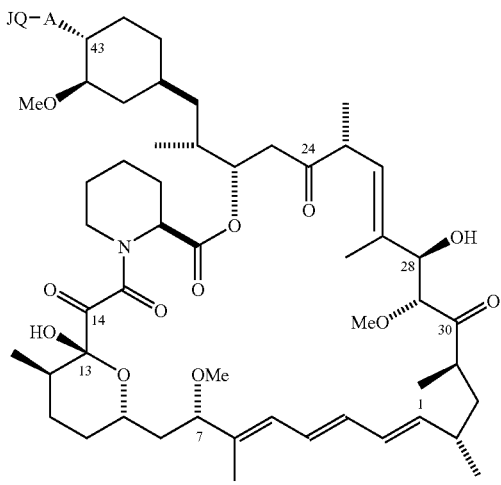

or a pharmaceutically acceptable salt thereof, wherein:
A is —O—, —S— or —NR$^2$— or is absent;
Q is absent or (if A is —O—, —S— or —NR$^2$—) Q may be —V—, —OV—, —SV—, or —NR$^2$V—, where V is an unsubstituted aliphatic or heteroaliphatic, an aryl, or a 5–14 membered heteroaryl moiety having 1–4 heteroatoms selected from nitrogen, oxygen, or sulfur, such that J is linked to the cyclohexyl ring directly, through A or through VA, OVA, SVA or NR$^2$VA;

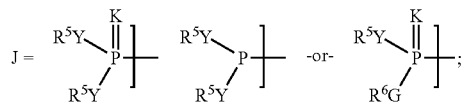

K is O or S;
each occurrence of Y is independently —O—, —S—, —NR$^2$—, or a bond;
each occurrence of R$^2$ and R$^5$ is independently H or an aliphatic, a heteroaliphatic, an aryl, or a 5–14 membered heteroaryl moiety having 1–4 heteroatoms selected from nitrogen, oxygen, or sulfur; and
each occurrence of R$^6$ is independently —PK(YR$^5$)(YR$^5$), —SO$_2$(YR$^5$) or —C(O)(YR$^5$); so long as any R$^2$ or R$^5$ moiety linked directly to P is not H;
wherein two R$^2$, R$^5$ and/or R$^6$ moieties may be chemically linked to one another to form a ring;
each occurrence of G is independently —O—, —S—, —NR$^2$— or (M)$_x$;
each occurrence of M is independently a substituted or unsubstituted methylene moiety, and any M—M moiety may be saturated or unsaturated;
each occurrence of x is independently an integer from 1–6;
wherein each aliphatic moiety contains 1–8 contiguous aliphatic carbon atoms, each heteroaliphatic moiety is an aliphatic moiety which contains an O, S, N, P or Si atom in place of one or more carbon atoms;
each of the foregoing aliphatic and heteroaliphatic moieties is independently linear or branched, or cyclic or acyclic, and unsubstituted or substituted with one or more groups selected from halogen, —YR$^2$, —Y—C(=O)R$^2$, —NR$^2$C(=O)R$^5$, —NR$^2$C(=O)NR$^5$, —NR$^2$C(=O)OR$^5$, —NR$^2$C(=NH)NR$^5$, —Y—C(=O)OR$^2$, —Y—C(=O)NR$^2$R$^5$, —Y—C(=NR$^2$)NR$^2$R$^5$, —COCOR$^2$, —COMCOR$^2$), J, —CN, —S(=O)R$^2$, —SO$_2$R$^2$, —SO$_2$NR$^2$R$^5$, —NO$_2$, —NR$^5$SO$_2$R$^2$—NR$^5$SO$_2$NR$^2$R, =O, =S, =NR$^2$, =NNR$^2$R$^5$, =NNHC(O)R$^2$, =NNHCO$_2$R$^2$, and =NNHSO$_2$R$^2$; and
each of the aryl, heteoraryl, acyl, aroyl or heteroaroyl moieties is independently unsubstituted or substituted with one or more groups selected from halogen, —YR$^2$, —Y—C(=O)R$^2$, —NR$^2$C(=O)R$^5$, —NR$^2$C(=O)NR$^5$, —NR$^2$C(=O)OR$^5$, —NR$^2$C(=NH)NR$^5$, —Y—C(=O)OR$^2$, —Y—C(=O)NR$^2$R$^5$, —Y—C(=NR$^2$)NR$^2$R$^5$, —COCOR$^2$, —COMCOR$^2$, J, —CN, —S(=O)R$^2$, —SO$_2$R$^2$, —SO$_2$NR$^2$R$^5$, —NO$_2$, —NR$^5$SO$_2$R$^2$ and —NR$^5$SO$_2$NR$^2$R;
with the proviso that: J-Q-A- is not (HO)$_2$(P=O)O— or (MeO)$_2$(P=O)O—.

2. A compound of the formula:

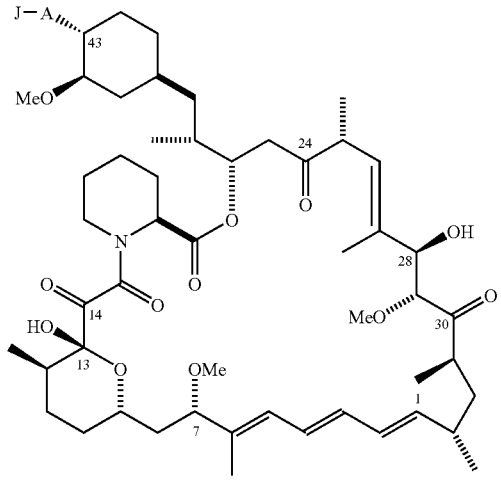

or a pharmaceutically acceptable salt thereof, wherein
A is —O—, —S— or —NR$^2$— or is absent;

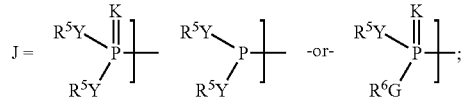

K is O or S;
each occurrence of Y is independently —O—, —S—, —NR$^2$—, or a bond;
each occurrence of R$^2$ and R$^5$ is independently H an aliphatic a heteroaliphatic, an aryl, or a 5–14 membered heteroaryl moiety having 1–4 heteroatoms selected from nitrogen, oxygen, or sulfur; and
each occurrence of R$^6$ is independently —PK(YR$^5$)(YR$^5$), —SO$_2$(YR$^5$) or —C(O)(YR$^5$); so long as any R$^2$ or R$^5$ moiety linked directly to P is not H;

wherein two R², R⁵ and/or R⁶ moieties may be chemically linked to one another to form a ring;

each occurrence of G is independently —O—, —S—, —NR²— or (M)$_x$;

each occurrence of M is independently a substituted or unsubstituted methylene moiety, and any M-M moiety may be saturated or unsaturated;

each occurrence of x is independently an integer from 1–6;

wherein each aliphatic moiety contains 1–8 contiguous aliphatic carbon atoms, each heteroaliphatic moiety is an aliphatic moiety which contains an O, S, N, P or Si atom in place of one or more carbon atoms;

each of the foregoing aliphatic and heteroaliphatic moieties is independently linear or branched, or cyclic or acyclic, and unsubstituted or substituted with one or more groups selected from halogen, —YR², —Y—C(=O)R², —NR²C(=O)R⁵, NR²C(=O)NR⁵, —NR²C(=O)OR⁵, —NR²C(=NH)NR⁵, —Y—C(=O)OR², —Y—C(=O)NR²R⁵, —Y—C(=NR²)NR²R⁵, —COCOR², —COMCOR²), J, —CN, —S(=O)R², —SO₂R², —SO₂NR²R⁵, —NO₂, —NR⁵SO₂R²— NR⁵SO₂NR²R, =O, =S, =NR², =NNR²R⁵, =NNHC(O)R², =NNHCO₂R², and =NNHSO₂R²; and each of the aryl, heteroaryl, acyl, aroyl or heteroaroyl moieties is independently unsubstituted or substituted with one or more groups selected from halogen, —YR², —Y—C(=O)R², —NR²C(=O)R⁵, —NR²C(=O)NR⁵, —NR²C(=O)OR⁵, —NR²C(=NH)NR⁵, —Y—C(=O)OR², —Y—C(=O)NR²R⁵, —Y—C(=NR²)NR²R⁵, —COCOR², —COMCOR², J, —CN, —S(=O)R², —SO₂R², —SO₂NR²R⁵, —NO₂, —NR⁵SO₂R² and —NR⁵SO₂NR²R;

with the proviso that (a) J-A- is not (HO)₂(P=O)O— or (MeO)₂(P=O)O—.

3. A compound of the formula:

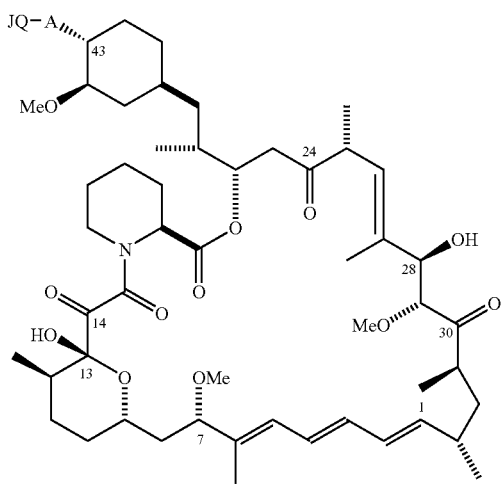

or a pharmaceutically acceptable salt thereof, wherein

J is chosen from

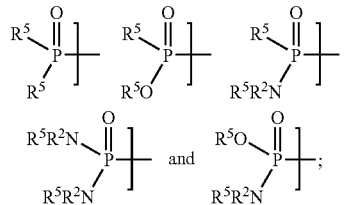

A is absent or is —O—, —S— or —NR²—;

Q is absent or (if A is —O—, —S— or —NR²—) Q may be —V—, —OV—, —SV—, or —NR²V—, where V is an unsubstituted aliphatic or heteroaliphatic, an aryl, or a 5–14 membered heteroaryl moiety having 1–4 heteroatoms selected from nitrogen, oxygen, or sulfur, such that J is linked to the cyclohexyl ring directly, through A or through VA, OVA, SVA or NR²VA;

each occurrence of Y is independently —O—, —S—, —NR²—, or a chemical bond;

each occurrence of R² and R⁵ is independently H or an aliphatic a heteroaliphatic, an aryl, or a 5–14 membered heteroaryl moiety having 1–4 heteroatoms selected from nitrogen, oxygen, or sulfur; so long as any R² or R⁵ moiety linked directly to P is not H;

wherein two R² and/or R⁵ moieties may be chemically linked to one another to form a ring;

wherein each aliphatic moiety contains 1–8 contiguous aliphatic carbon atoms, each heteroaliphatic moiety is an aliphatic moiety which contains an O, S, N, P or Si atom in place of one or more carbon atoms;

each of the foregoing aliphatic and heteroaliphatic moieties is independently linear or branched, or cyclic or acyclic, and unsubstituted or substituted with one or more groups selected from halogen, —YR², —Y—C(=O)R², —NR²C(=O)R⁵, —NR²C(=O)NR⁵, —NR²C(=O)OR⁵, —NR²C(=NH)NR⁵, —Y—C(=O)OR², —Y—C(=O)NR²R⁵, —Y—C(=NR²)NR²R⁵, —COCOR², —COMCOR²), J, —CN, —S(=O)R², —SO₂R², —SO₂NR²R⁵, —NO₂, —NR⁵SO₂R² —NR⁵SO₂NR²R, =O, =S, =NR², =NNR²R⁵, =NNHC(O)R², =NNHCO₂R², and =NNHSO₂R²; and each of the aryl, heteroaryl, acyl, aroyl or heteroaroyl moieties is independently unsubstituted or substituted with one or more groups selected from halogen, —YR², —Y—C(=O)R², —NR²C(=O)R⁵, —NR²C(=O)NR⁵, —NR²C(=O)OR⁵, —NR²C(=NH)NR⁵, —Y—C(=O)OR², —Y—C(=O)NR²R⁵, —Y—C(=NR²)NR²R⁵, —COCOR², —COMCOR², J, —CN, —S(=O)R², —SO₂R², —SO₂NR²R⁵, —NO₂, —NR⁵SO₂R² and —NR⁵SO₂NR²R;

in which each occurrence of R² and R⁵ is an independently chosen lower aliphatic or aryl moiety, which may be substituted or unsubstituted, except that in addition, —OR⁵ and —NR²R⁵, may be —OH and —NHR⁵.

4. A compound of the formula:

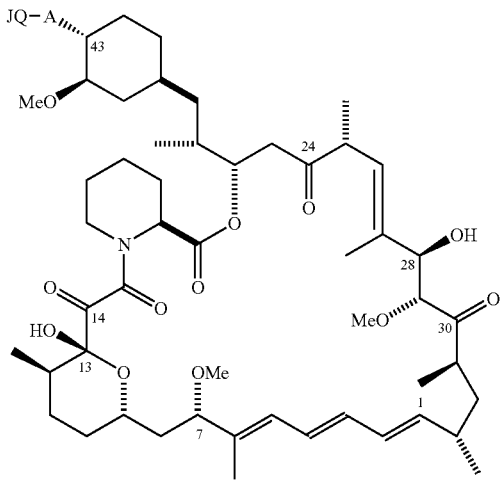

or a pharmaceutically acceptable salt thereof, wherein
J is chosen from:

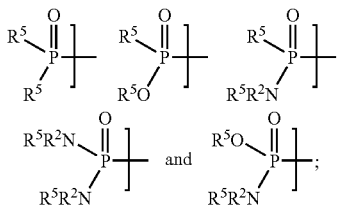

A is absent or is —O—, —S— or —NR²—;

Q is absent or (if A is —O—, —S— or —NR²—) Q may be —V—, —OV—, —SV—, or —NR²V—, where V is an aliphatic, a heteroaliphatic, an aryl, or a 5–14 membered heteroaryl moiety having 1–4 heteroatoms selected from nitrogen, oxygen, or sulfur, such that J is linked to the cyclohexyl ring directly, through A or through VA, OVA, SVA or NR²VA;

each occurrence of Y is independently —O—, —S—, —NR²—, or a chemical bond;

in which each occurrence of $R^2$ and $R^5$ is an independently chosen lower aliphatic or aryl moiety, which may be substituted or unsubstituted, except that in addition, —OR⁵ and —NR²R⁵, may be —OH and —NHR⁵;

wherein two $R^2$ and/or $R^5$ moieties may be chemically linked to one another to form a ring;

wherein each aliphatic moiety contains 1–8 continuous aliphatic carbon atoms, each heteroaliphatic moiety is an aliphatic moiety which contains an O, S, N, P or Si atom in place of one or more carbon atoms;

each of the foregoing aliphatic and heteroaliphatic moieties is independently linear or branched, or cyclic or acyclic, and unsubstituted or substituted with one or more groups selected from halogen, —YR², —Y—C(=O)R², —NR²C(=O)R⁵, —NR²C(=O)NR⁵, —NR⁵C(=O)OR⁵, —NR²C(=NH)NR⁵, —Y—C(=O)OR², —Y—C(=O)NR²R⁵, —Y—C(=NR²)NR²R⁵, —COCOR², —COMCOR²), J, —CN, —S(=O)R², —SO₂R², —SO₂NR²R⁵, —NO₂, —NR⁵SO₂R² —NR⁵SO₂NR²R, =O, =S, =NR², =NNR²R⁵, =NNHC(O)R², =NNHCO₂R², and =NNHSO₂R²; and each of the aryl, heteroaryl, acyl, aroyl or heteroaroyl moieties is independently unsubstituted or substituted with one or more groups selected from halogen, —YR², —Y—C(=O)R², —NR²C(=O)R⁵, —NR²C(=O)NR⁵, —NR²C(=O)OR⁵, —NR²C(=NH)NR⁵, —Y—C(=O)OR², —Y—C(=O)NR²R⁵, —Y—C(=NR²)NR²R⁵, —COCOR², —COMCOR², J, —CN, —S(=O)R², —SO₂R², —SO₂NR²R⁵, —NO₂, —NR⁵SO₂R² and —NR⁵SO₂NR²R;

with the proviso that if J-Q-A- is (R²Y)(Me)(P=O)O—, then (R²Y) contains 15 or fewer carbon atoms.

5. The compound of claim 1 in which each occurrence of $R^2$ and $R^5$ is an independently chosen C1–C6 alkyl group optionally bearing one or more halo, —OH, alkoxyl-, alkyloxyalkyloxy-, haloalkyl-, hydroxyalkoxyl-, hetrocyclic, aryl or heteroaryl substituents, except that in addition, —OR⁵ and —NR²R⁵, may be —OH and —NHR⁵, respectively.

6. The compound of claim 2 in which each occurrence of $R^2$ and $R^5$ is an independently chosen C1–C6 alkyl group optionally bearing one or more halo, —OH, alkoxyl-, alkyloxyalkyloxy-, haloalkyl-, hydroxyalkoxyl-, hetrocyclic, aryl or heteroaryl substituents, except that in addition, —OR⁵ and —NR²R⁵, may be —OH and —NHR⁵, respectively.

7. The compound of claim 3 in which each occurrence of $R^2$ and $R^5$ is an independently chosen C1–C6 alkyl group optionally bearing one or more halo, —OH, alkoxyl-, alkyloxyalkyloxy-, haloalkyl-, hydroxyalkoxyl-, hetrocyclic, aryl or heteroaryl substituents, except that in addition, —OR⁵ and —NR²R⁵, may be —OH and —NHR⁵, respectively.

8. The compound of claim 4 in which each occurrence of $R^2$ and $R^5$ is an independently chosen C1–C6 alkyl group optionally bearing one or more halo, —OH, alkoxyl-, alkyloxyalkyloxy-, haloalkyl-, hydroxyalkoxyl-, hetrocyclic, aryl or heteroaryl substituents, except that in addition, —OR⁵ and —NR²R⁵, may be —OH and —NHR⁵, respectively.

9. The compound of claim 5 in which each occurrence of $R^2$ and $R^5$ is independently chosen from methyl, ethyl, n-propyl, -i-propyl, n-butyl, 2-butyl, t-butyl, phenyl, or heteroaryl, each of which optionally bearing one or more halo, —OH, alkoxyl-, alkoxylalkoxyl-, haloalkyl-, hydroxyalkoxyl-, heterocyclic, aryl or heteroaryl substituents, and in addition, —OR⁵ and —NR²R⁵, may be —OH and —NHR⁵, respectively.

10. The compound of claim 6 in which each occurrence of $R^2$ and $R^5$ is independently chosen from methyl, ethyl, n-propyl, -i-propyl, n-butyl, 2-butyl, t-butyl, phenyl, or heteroaryl, each of which optionally bearing one or more halo, —OH, alkoxyl-, alkoxylalkoxyl-, haloalkyl-, hydroxyalkoxyl-, heterocyclic, aryl or heteroaryl substituents, and in addition, —OR⁵ and —NR²R⁵, may be —OH and —NHR⁵, respectively.

11. The compound of claim 7 in which each occurrence of $R^2$ and $R^5$ is independently chosen from methyl, ethyl, n-propyl, -i-propyl, n-butyl, 2-butyl, t-butyl, phenyl, or heteroaryl, each of which optionally bearing one or more halo, —OH, alkoxyl-, alkoxylalkoxyl-, haloalkyl-, hydroxyalkoxyl-, heterocyclic, aryl or heteroaryl substituents, and in addition, —OR⁵ and —NR²R⁵, may be —OH and —NHR⁵, respectively.

12. The compound of claim 8 in which each occurrence of $R^2$ and $R^5$ is independently chosen from methyl, ethyl, n-propyl, -i-propyl, n-butyl, 2-butyl, t-butyl, phenyl, or heteroaryl, each of which optionally bearing one or more halo, —OH, alkoxyl-, alkoxylalkoxyl-, haloalkyl-, hydroxyalkoxyl-, heterocyclic, aryl or heteroaryl substituents, and in addition, —$OR^5$ and —$NR^2R^5$, may be —OH and —$NHR^5$, respectively.

13. The compound of claim 1 wherein J is chosen from the following:

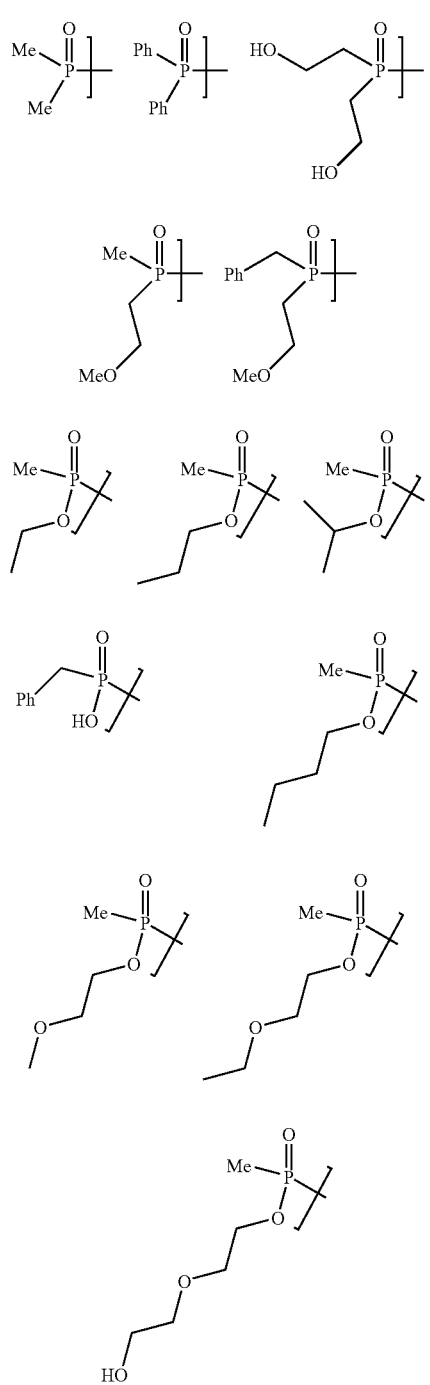

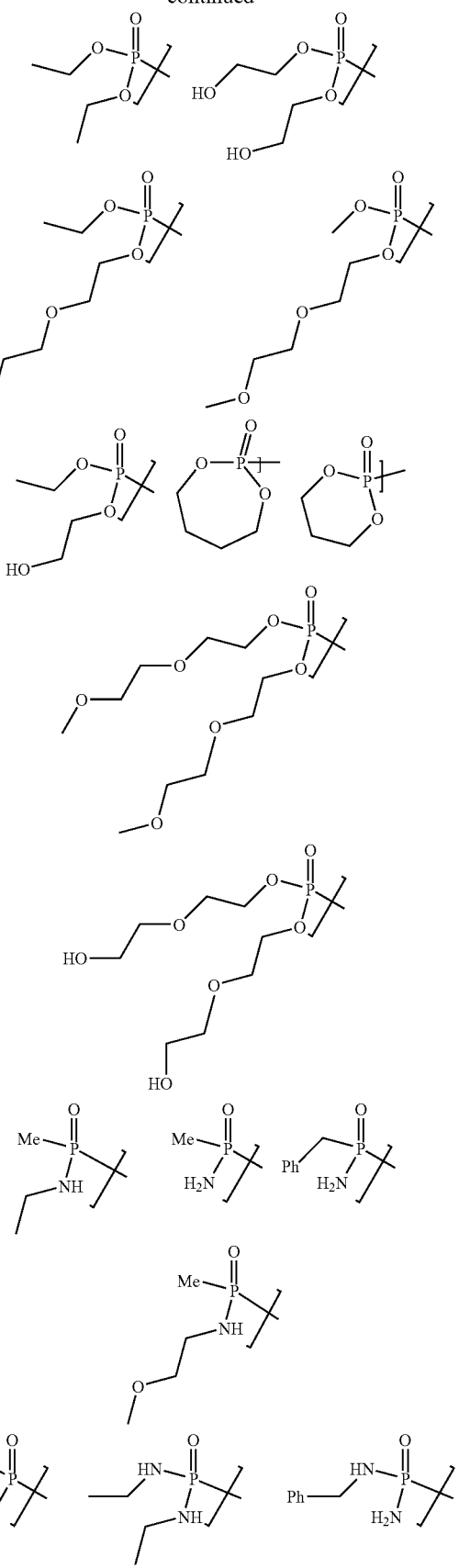

-continued

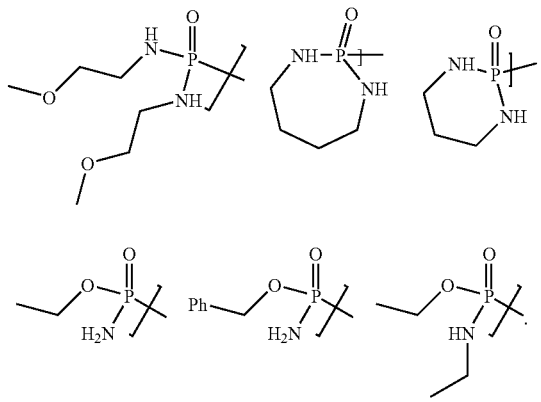

14. The compound of claim 1 in which QA is —O—, —OVO—, —NH—, —OVNH—, —S—, or —SVS—, where V is a lower aliphatic moiety.

15. The compound of claim 4 in which QA is —O—, —OVO—, —NH—, —OVNH—, —S—, or —SVS—, where V is a lower aliphatic moiety.

16. The compound of claim 5 in which QA is —O—, —OVO—, —NH—, —OVNH—, —S—, or —SVS—, where V is a lower aliphatic moiety.

17. The compound of claim 8 in which QA is —O—, —OVO—, —NH—, —OVNH—, —S—, or —SVS—, where V is a lower aliphatic moiety.

18. The compound of claim 9 in which QA is —O—, —OVO—, —NH—, —OVNH—, —S—, or —SVS—, where V is a lower aliphatic moiety.

19. The compound of claim 13 which comprises a moiety JQA- in which QA is —O—, —OVO—, —NH—, —OVNH—, —S—, or —SVS—, where V is a lower aliphatic moiety.

20. The compound of any of claims 1–19 in which JQA- or JA- comprises $(R^2Y)(Me)(P=O)O$— in which $R^2Y$ contains 15 or fewer carbon atoms.

21. The compound of claim 20 in which JQA- comprises $(R^2Y)(Me)(P=O)O$— in which $R^2Y$— contains 10 or fewer carbon atoms.

22. A rapamycin or 43-epi-rapamycin in which the hydroxyl group at position 43 is replaced by a group JQA-, wherein:

A is —O—, —S— or —NR$^2$— or is absent;

Q is absent or (if A is —O—, —S— or —NR$^2$—) Q may be —V—, —OV—, —SV—, or —NR$^2$V—, where V is an unsubstituted aliphatic or heteroaliphatic, an aryl, or a 5–14 membered heteroaryl moiety having 1–4 heteroatoms selected from nitrogen, oxygen, or sulfur, such that J is linked to the cyclohexyl ring directly, through A or through VA, OVA, SVA or NR$^2$VA;

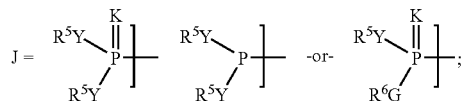

K is O or S;
each occurrence of Y is independently —O—, —S—, —NR$^2$—, or a bond;

each occurrence of $R^2$ and $R^5$ is independently H or an aliphatic, a heteroaliphatic, an aryl, or a 5–14 membered heteroaryl moiety having 1–4 heteroatoms selected from nitrogen, oxygen, or sulfur; and each occurrence of $R^6$ is independently —PK(YR$^5$)(YR$^5$), —SO$_2$(YR$^5$) or —C(O)(YR$^5$); so long as any $R^2$ or $R^5$ moiety linked directly to P is not H; wherein two $R^2$, $R^5$ and/or $R^6$ moieties may be chemically linked to one another to form a ring;

each occurrence of G is independently —O—, —S—, —NR$^2$— or (M)$_x$;

each occurrence of M is independently a substituted or unsubstituted methylene moiety, and any M-M moiety may be saturated or unsaturated;

each occurrence of x is independently an integer from 1–6;

wherein each aliphatic moiety contains 1–8 contiguous aliphatic carbon atoms, each heteroaliphatic moiety is an aliphatic moiety which contains an O, S, N, P or Si atom in place of one or more carbon atoms, each of the foregoing aliphatic and heteroaliphatic moieties is independently linear or branched, or cyclic or acyclic, and unsubstituted or substituted with one or more groups selected from halogen, —YR$^2$, —Y—C(=O)R$^2$, —NR$^2$C(=O)R$^5$, —NR$^3$C(=O)NR$^5$, —NR$^2$C(=O)OR$^5$, —NR$^2$C(=NH)NR$^5$, —Y—C(=O)OR$^2$, —Y—C(=O)NR$^2$R$^5$, —Y—C(=NR$^2$)NR$^2$R$^5$, —COCOR$^2$, —COMCOR$^2$), J, —CN, —S(=O)R$^2$, —SO$_2$R$^2$, —SO$_2$NR$^2$R$^5$, —NO$_2$, —NR$^5$SO$_2$R$^2$ —NR$^5$SO$_2$NR$^2$R, =O—, =S, =NR$^2$, =NNR$^2$R$^5$, =NNHC(O)R$^2$, =NNHCO$_2$R$^2$, and =NNHSO$_2$R$^2$, and each of the aryl, heteoraryl, acyl, aroyl or heteroaroyl moieties is independently unsubstituted or substituted with one or more groups selected from halogen, —YR$^2$, —Y—C(=O)R$^2$, —NR$^2$C(=O)R$^5$, —NR$^2$C(=O)NR$^5$, —NR$^2$C(=O)OR$^5$, —NR$^2$C(=NH)NR$^5$, —Y—C(=O)OR$^2$, —Y—C(=O)NR$^2$R$^5$, —Y—C(=NR$^2$)NR$^2$R$^5$, —COCOR$^2$, —COMCOR$^2$, J, —CN, —S(=O)R$^2$, —SO$_2$R$^2$, —SO$_2$NR$^2$R$^5$, —NO$_2$, —NR$^5$SO$_2$R$^2$ and —NR$^5$SO$_2$NR$^2$R;

with one or more of the following additional features:

(a) epimerization at position 28, or replacement of the position 28 hydroxyl group (in either sterochemical orientation) with halo, —OR$^2$ or —OC(=O)AR$^2$;

(b) replacement of the ketone at position 24 with a substituted or unsubstituted oxime, or with a hydroxyl group or derivative thereof of the formula —OR$^2$ or —OC(=O)AR$^2$;

(c) replacement of the ketone at position 24 with a substituted or unsubstituted oxime, or with a hydroxyl group or derivative thereof of the formula —OR$^2$ or —OC(=O)AR$^2$;

(d) epimerization of the —OMe at position 7 and/or replacement of the —OMe with a moiety selected from H, halo, —R$^4$, —OR$^4$, —SR$^4$, —OC(O)R$^4$, —OC(O)NR$^A$R$^B$, —NR$^A$R$^B$, —NR$^B$C(O)R$^4$, —NR$^B$C(O)OR$^4$, —NR$^B$SO$_2$R$^4$ or —NR$^B$SO$_2$NR$^A$R$^{B_1}$; where R$^A$ is R$^2$ and where R$^B$ is —OH or R$^2$; and (e) elimination of the —OMe at position 7 yielding the tetra-ene moiety:

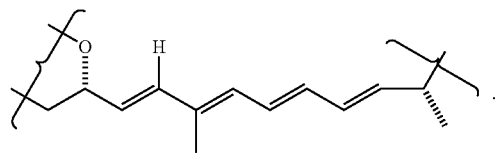

23. The compound of claim 22 in which each occurrence of $R^2$ and $R^5$ is an independently chosen C1–C6 alkyl group optionally bearing one or more halo, —OH, alkoxyl-, alkyloxyalkyloxy-, haloalkyl-, hydroxyalkoxyl-, hetrocyclic, aryl or heteroaryl substituents, except that in addition, —OR$^5$ and —NR$^2$R$^5$ may be —OH and —NHR$^5$, respectively.

24. The compound of claim 23 in which each occurrence of $R^2$ and $R^5$ is independently chosen from methyl, ethyl, n-propyl, -i-propyl, n-butyl, 2-butyl, t-butyl, phenyl, or heteroaryl, each of which optionally bearing one or more halo, —OH, alkoxyl-, alkoxylalkoxyl-, haloalkyl-, hydroxyalkoxyl-, heterocyclic, aryl or heteroaryl substituents, and in addition, —OR$^5$ and —NR$^2$R$^5$ may be —OH and —NHR$^5$, respectively.

25. The compound of claim 22 in which QA is —OVO—, —OVNH— or —SVS—, where V is a lower aliphatic moiety.

26. The compound of any of claims 22–25 wherein J is chosen from the following:

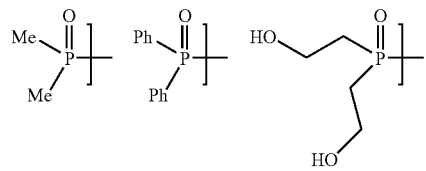

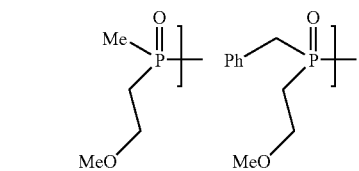

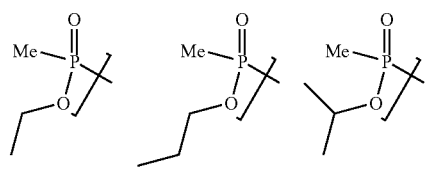

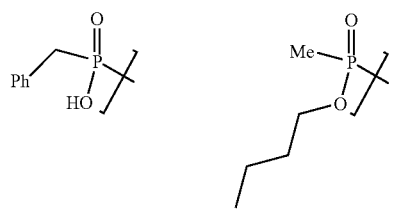

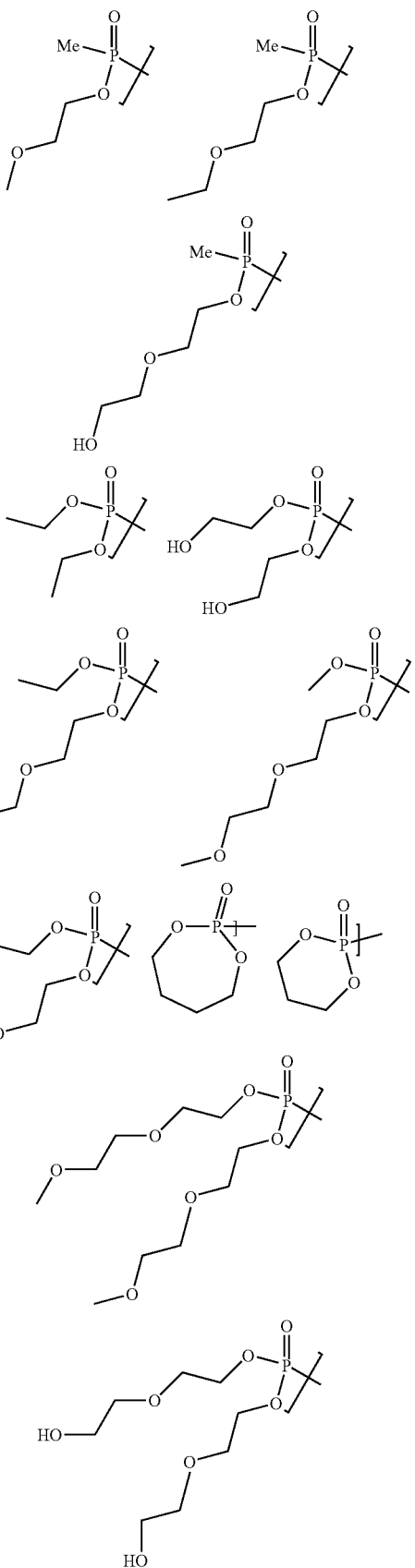

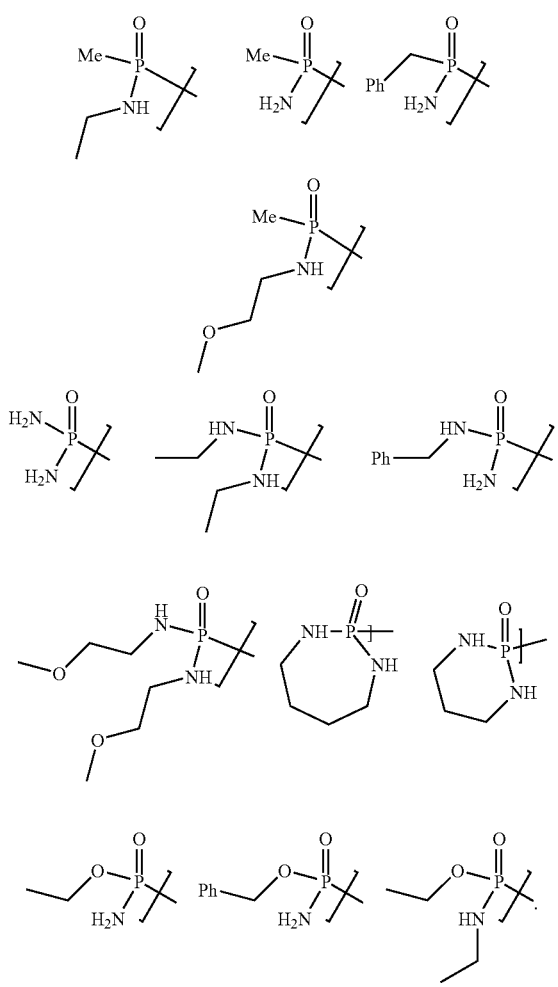

27. A compound of the formula:

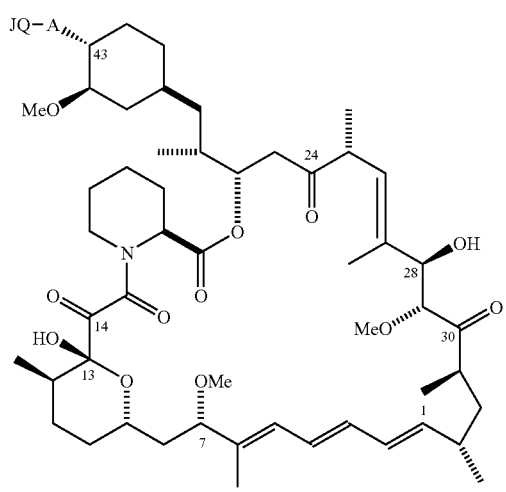

wherein
J is one of the following:

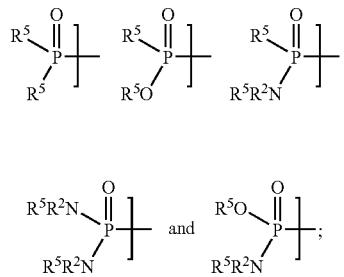

A is —O—, —S— or —NR²— or is a covalent bond;

Q is a covalent bond or, if A is —O—, —S— or —NR²—, Q may be —V—, —OV—, —SV—, or —NR²V—, where V is an aliphatic, a heteroaliphatic, an aryl, or a 5–14 membered heteroaryl moiety having 1–4 heteroatoms selected from nitrogen, oxygen, or sulfur, such that J is linked to the cyclohexyl ring directly, through A or through VA, OVA, SVA or NR²VA;

each occurrence of R² and R⁵ is independently a substituted or unsubstituted $C_{1-6}$ aliphatic or aryl moiety or —OR⁵ and —NR²R⁵ may be —OH and —NHR⁵, respectively;

wherein each aliphatic moiety (other than R² and R⁵) contains 1–8 contiguous aliphatic carbon atoms, each heteroaliphatic moiety is an aliphatic moiety which contains an O, S, N, P or Si atom in place of one or more carbon atoms; each of the foregoing aliphatic and heteroaliphatic moieties is independently linear or branched, or cyclic or acyclic, and substituted or unsubstituted, and each of the aryl, heteoaryl, acyl, aroyl or heteroaroyl moieties is independently substituted or unsubstituted;

wherein substituents for aliphatic and hetero aliphatic moieties (including non-aromatic heterocyclic moieties), and for an unsaturated carbon atom of an aryl or heteroaryl moiety, may be halogen, —YR², —Y—C(=O)R², —YC(=O)OR², —YC(=O)NR²R⁵, —YC(NR²)NR²R⁵, —COCOR², —COMCOR²), J, —CN, —S(=O)R², —SO₂R², —SO₂NR²R⁵, —NO₂, —NR⁵SO₂R² or —NR⁵SO₂NR²R⁵ (where each occurrence of Y is independently O, S, NR₂ or a covalent bond) and in addition (in the case of a saturated carbon atom) may also be =O, =S, =NR², =NNR²R⁵, =NNHC(O)R², =NNHCO₂R² or =NNHSO₂R²; and substituents on the nitrogen of an aromatic or non-aromatic heterocyclic ring may be —R², —NR²R⁵, —C(=O)R², —C(=O)OR², —C(=O)NR²R⁵, —C(=NR²)NR²R⁵, —COCOR², —COMCOR², —CN, —NR⁵SO₂R² or —NR⁵SO₂NR²R⁵.

28. A compound of the formula

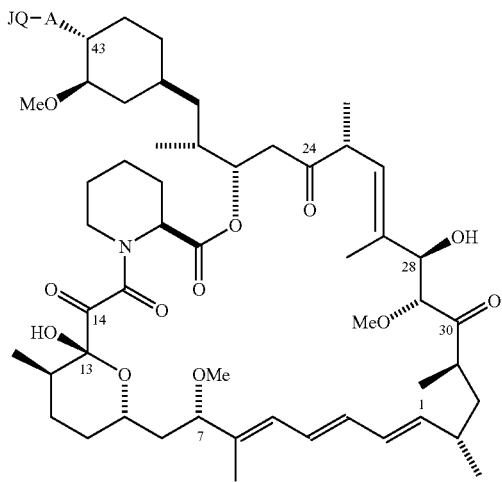

where J is selected from: —P(O)Me$_2$, —P(O)Et$_2$, —P(O)Ph$_2$, —P(O)(OMe)(Me), —P(O)(OEt)(Me), —P(O)(OnPr)(Me), —P(O)(OiPr)(Me), —P(O)(OnBu)(Me), —P(O)(Me)(OCH$_2$CH$_2$OMe), —P(O)(Me)(OCH$_2$CH$_2$OEt), —P(O)(Me)(OCH$_2$CH$_2$OCH$_2$CH$_2$OH), —P(O)(OMe)(Et), —P(O)(CH$_2$CH$_2$OH)$_2$, —P(O)(OEt)$_2$, —P(O)(NH$_2$)$_2$, and —P(O)(OH)—CH$_2$—PO(OH)$_2$.

29. The compound of claim 28 in which J is —P(O)Me$_2$, —P(O)Et$_2$, or —P(O)Ph$_2$.

30. A composition comprising (a) a compound of any of claims 1 through 19, 22 through 25, or 27 through 29, and (b) a pharmaceutically acceptable vehicle, optionally containing (c) one or more pharmaceutically acceptable excipients.

31. A composition suitable for oral administration to a mammal, the composition comprising (a) a compound of any of claims 1 through 19, 22 through 25, or 27 through 29, and (b) a pharmaceutically acceptable vehicle, optionally containing (c) one or more pharmaceutically acceptable excipients.

32. A composition suitable for parenteral administration to a mammal, the composition comprising (a) a compound of any of claims 1 through 19, 22 through 25, or 27 through 29, and (b) a pharmaceutically acceptable vehicle, optionally containing (c) one or more pharmaceutically acceptable excipients.

33. A method for suppressing the immune response of a subject by administering to the subject an immunosuppressive amount of a composition of claim 30.

34. A method for treating or suppressing the rejection of transplanted tissues in a recipient, which method comprises administering to said recipient an effective amount of a composition of claim 30.

35. A method for treating graft vs. host disease, lupus, rheumatoid arthritis, diabetes mellitus, myasthenia gravis, multiple sclerosis, psoriasis, dermatitis, eczema, seborrhea, inflammatory bowel disease, pulmonary inflammation, ocular uveitis; adult T-cell leukemia/lymphoma; fungal infections; hyperproliferative restenosis; graft vascular atherosclerosis; cerebral vascular disease, coronary artery disease, cerebrovascular disease, arteriosclerosis, atherosclerosis, nonatheromatous arteriosclerosis, or vascular wall damage from cellular events leading toward immune mediated vascular damage, stroke or multiinfarct dementia in a subject in need thereof, which method comprises administering to said subject a therapeutically effective amount of a composition of claim 30.

36. A method for treating cancer in a subject in need thereof, which comprises administering to the subject a treatment effective amount of a composition of claim 30, wherein said cancer is selected from glioblastoma; cancer of the prostate, breast, pancreas, lung or colon; bone sarcoma, soft tissue sarcoma, lymphoma or a leukemia.

* * * * *

UNITED STATES PATENT AND TRADEMARK OFFICE
CERTIFICATE OF CORRECTION

PATENT NO.        : 7,091,213 B2
APPLICATION NO.   : 10/862149
DATED             : August 15, 2006
INVENTOR(S)       : Metcalf, III et al.

It is certified that error appears in the above-identified patent and that said Letters Patent is hereby corrected as shown below:

Col. 107, line 1,

Claim 28 is replaced with the following:

28. A compound of the formula

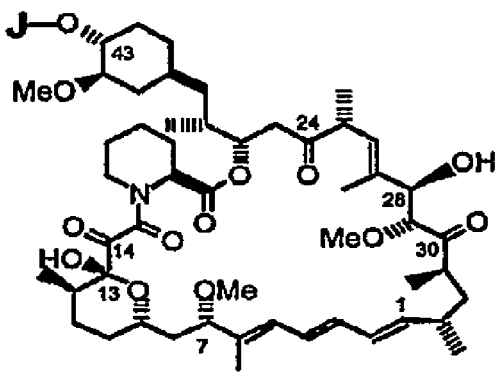

where J is selected from: $-P(O)Me_2$, $-P(O)Et_2$, $-P(O)Ph_2$, $-P(O)(OMe)(Me)$, $-P(O)(OEt)(Me)$, $-P(O)(OnPr)(Me)$, $-P(O)(OiPr)(Me)$, $-P(O)(OnBu)(Me)$, $-P(O)(Me)(OCH_2CH_2OMe)$, $-P(O)(Me)(OCH_2CH_2OEt)$, $-P(O)(Me)(OCH_2CH_2OCH_2CH_2OH)$, $-P(O)(OMe)(Et)$, $-P(O)(CH_2CH_2OH_2$, $-P(O)(OEt)_2$, $-P(O)(NH_2)_2$, and $-P(O)(OH)-CH_2-PO(OH)_2$, Signed and Sealed this Twentieth Day of March, 2007

JON W. DUDAS
*Director of the United States Patent and Trademark Office*